United States Patent
Diolez et al.

(10) Patent No.: US 11,484,529 B2
(45) Date of Patent: Nov. 1, 2022

(54) DESMETHYLANETHOLE TRITHIONE DERIVATIVES FOR THE TREATMENT OF DISEASES LINKED TO MITOCHONDRIAL REACTIVE OXYGEN SPECIES (ROS) PRODUCTION

(71) Applicants: OP2 Drugs, Pessac (FR); Centre Hospitalier Universitaire de Bordeaux, Talence (FR); Institut National de la Santé et de la Recherche Médicale (INSERM), Paris (FR); Université de Bordeaux, Bordeaux (FR)

(72) Inventors: Philippe Diolez, Pessac (FR); Frédéric Marin, Paris (FR); Olivier Petitjean, Senlis (FR)

(73) Assignees: OP2 Drugs, Pessac (FR); Centre Hospitalier Universitaire de Bordeaux, Talence (FR); Institut National de la Santé et de la Recherche Médicale (INSERM), Paris (FR); Université de Bordeaux, Bordeaux (FR)

( * ) Notice: Subject to any disclaimer, the term of this patent is extended or adjusted under 35 U.S.C. 154(b) by 222 days.

(21) Appl. No.: 16/491,617

(22) PCT Filed: Mar. 7, 2018

(86) PCT No.: PCT/EP2018/055651
§ 371 (c)(1),
(2) Date: Sep. 6, 2019

(87) PCT Pub. No.: WO2018/162581
PCT Pub. Date: Sep. 13, 2018

(65) Prior Publication Data
US 2021/0154175 A1    May 27, 2021

Related U.S. Application Data

(60) Provisional application No. 62/467,874, filed on Mar. 7, 2017.

(30) Foreign Application Priority Data

Mar. 7, 2017 (EP) .................................... 17159691

(51) Int. Cl.
| | |
|---|---|
| *A61K 31/428* | (2006.01) |
| *A61P 3/10* | (2006.01) |
| *A61K 31/385* | (2006.01) |
| *A61K 31/404* | (2006.01) |
| *A61K 31/423* | (2006.01) |
| *C07D 417/04* | (2006.01) |
| *C07D 413/04* | (2006.01) |
| *C07D 409/04* | (2006.01) |

(52) U.S. Cl.
CPC .......... *A61K 31/428* (2013.01); *A61K 31/385* (2013.01); *A61K 31/404* (2013.01); *A61K 31/423* (2013.01); *A61P 3/10* (2018.01); *C07D 409/04* (2013.01); *C07D 413/04* (2013.01); *C07D 417/04* (2013.01)

(58) Field of Classification Search
CPC .. A61K 31/428; A61K 31/385; A61K 31/404; A61K 31/423
See application file for complete search history.

(56) References Cited

FOREIGN PATENT DOCUMENTS

| | | |
|---|---|---|
| CN | 1385156 A | 12/2002 |
| CN | 102961375 A | 3/2013 |
| EP | 2889294 A1 | 7/2015 |
| WO | 1998027970 A2 | 7/1998 |
| WO | 2001009118 A2 | 2/2001 |
| WO | 2003028715 A2 | 4/2003 |
| WO | 2003066058 A1 | 8/2003 |

(Continued)

OTHER PUBLICATIONS

Balaban et al., Cell. Feb. 25, 2005;120(4):483-95.

(Continued)

*Primary Examiner* — Alicia L Otton
(74) *Attorney, Agent, or Firm* — Panitch Schwarze Belisario & Nadel LLP; Erin M. Dunston

(57) ABSTRACT

The present invention relates to desmethylanethole trithione (AOX) and derivatives thereof, especially derivatives of formula (I), for the prevention and treatment of diseases whose initiation and/or evolution relates to the production and effects of reactive oxygen species (ROS) of mitochondrial origin,

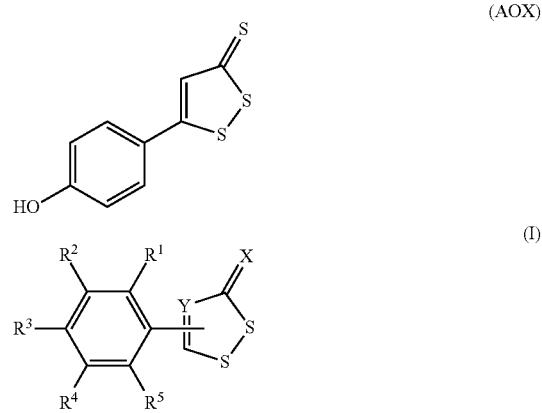

18 Claims, 24 Drawing Sheets

(56) References Cited

FOREIGN PATENT DOCUMENTS

| WO | 2003068219 A1 | 8/2003 |
|---|---|---|
| WO | 2006089861 | 8/2006 |
| WO | 2008106640 A1 | 9/2008 |

OTHER PUBLICATIONS

Betarbet et al., Nat Neurosci. Dec. 2000;3(12):1301-6.
Bjelakovic et al., JAMA. Feb. 28, 2007;297(8):842-57.
Brown et al., Bioorg Med Chem Lett. Dec. 15, 2014;24(24):5829-5831.
Cardinal et al., Endocrinology. Feb. 2015;156(2):411-8.
Cardinal et al., Mol Metab. Aug. 1, 2014;3(7):705-16.
Freund-Michel et al., Ther Adv Respir Dis. Jun. 2013;7(3):175-200.
Garlid et al., Am J Physiol Heart Circ Physiol. Jul. 2006;291(1):H152-60.
Giustarini et al., Biochem Pharmacol. May 15, 2014;89(2):246-54.
Goncalves et al., J Biol Chem. Jan. 2, 2015;290(1):209-27.
Goodman et al., J Natl Cancer Inst. Dec. 1, 2004;96(23):1743-50.
Gouspillou et al., Aging Cell. Feb. 2014;13(1):39-48.
Granger et al., Redox Biol. Dec. 2015;6:524-551.
Kaneto et al., Mediators Inflamm. 2010;2010:453892.
Lambert et al., Aging Cell. Feb. 2010;9(1):78-91.
Lambert et al., Aging Cell. Oct. 2007;6(5):607-18.
Langston et al., Science. Feb. 25, 1983;219(4587):979-80.
Muñoz et al., Parkinsons Dis. 2016;2016:7049108.
Nagayasu et al., Br J Cancer. May 1998;77(9):1371-7.
Nita et al., Oxid Med Cell Longev. 2016;2016:3164734.
Orr et al., Free Radic Biol Med. Dec. 2013;65:1047-1059.
Polster et al., Methods Enzymol. 2014;547:225-50.
Porporato et al., Cell Rep. Aug. 7, 2014;8(3):754-66.
Quinlan et al., Redox Biol. May 23, 2013;1:304-12.
Quinlan et al., J Biol Chem. Sep. 9, 2011;286(36):31361-72.
Sarvazyan, Am J Physiol. Nov. 1996;271(5 Pt 2):H2079-85.
Spadoni et al., Arthritis Rheumatol. Jun. 2015;67(6):1611-22.
Valcovici et al., Arch Med Sci. Apr. 1, 2016;12(2):428-35.
Viana et al., Eur J Med Chem Chim Ther. 1986;21(2):123-30.
Vichai et al., Nat Protoc. 2006;1(3):1112-6.
Zhang et al., J Cardiovasc Pharmacol. May 2008;51(5):443-9.
Zhao et al., Proc Natl Acad Sci U S A. Apr. 19, 2005;102(16):5727-32.
C H Switzer et al., "Dithiolethione compounds inhibit Akt signaling in human breast and lung cancer cells by increasing PP2A activity", Oncogene, Oct. 29, 2009, vol. 28, No. 43, pp. 3837-3846.
S Matsuo et al., "Anetholtrithion stabilizes body weight fluctuation caused by excessive water drinking in a patient with schizophrenia: a case report", The Journal of Clinical Psychiatry, Oct. 1999, vol. 60, No. 10, pp. 706.
P M Dansette et al., "Sulfur containing compounds as antioxidants". Advances in Experimental Medicine and Biology, 1990, vol. 264, pp. 209-215.
Zhi Jian Song et al., "Hydrogen sulfide donors in research and drug development". MedChemComm. Apr. 22, 2014, 2014, vol. 5, No. 5, pp. 557-570.
James F Toole et al., "Lowering homocysteine in patients with ischemic stroke to prevent recurrent stroke, myocardial infarction, and death: the Vitamin Intervention for Stroke Prevention (VISP) randomized controlled trial". JAMA. Feb. 4, 2004, vol. 291, No. 5, pp. 565-575.

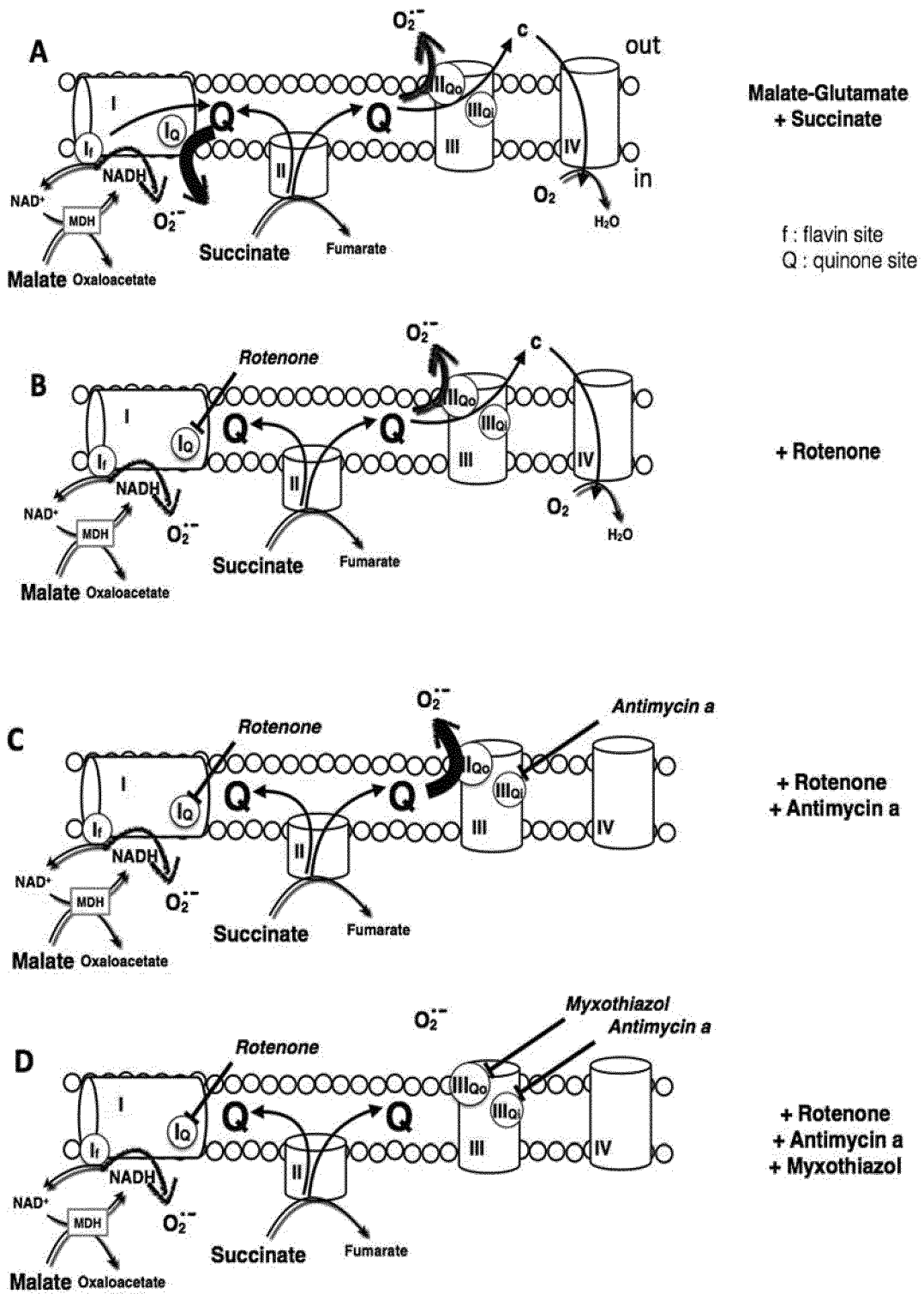
FIG. 2A-D

DESMETHYLANETHOLE TRITHIONE DERIVATIVES FOR THE TREATMENT OF DISEASES LINKED TO MITOCHONDRIAL REACTIVE OXYGEN SPECIES (ROS) PRODUCTION

CROSS-REFERENCE TO RELATED APPLICATIONS

This application is a U.S. National Stage patent application pursuant to 35 U.S.C. § 371 of International Patent Application PCT/EP2018/055651, filed on Mar. 7, 2018, and published as WO 2018/162581 on Sep. 13, 2018, which claims priority to European Patent Application 17159691.9, filed on Mar. 7, 2017, and U.S. Provisional Patent Application No. 62/467,874, filed on Mar. 7, 2017, all of which are incorporated herein by reference in their entireties for all purposes.

FIELD OF INVENTION

The present invention relates to desmethylanethole trithione (AOX) and derivatives thereof, especially derivatives of formula (I) as disclosed in the claims, for the prevention and treatment of diseases whose initiation and/or evolution relates to the production and effects of reactive oxygen species (ROS) of mitochondrial origin.

BACKGROUND OF INVENTION

Mitochondrion is at the heart of the now widely acknowledged "free radical theory of ageing" and thus involved in the pathogenesis of nearly all ageing-associated diseases, including cardiovascular disease, neurodegenerative diseases (Parkinson's disease, Alzheimer's disease and the like), cancer and diabetes, as well as tissue dysfunctions of ischemic origin. This theory states that the accumulation of damages caused by reactive oxygen species (ROS) impacts numerous cellular functions, in particular mitochondrial functions, which are essential for energy supply and optimal cellular functioning.

Mitochondria thus appear as the primary targets of ROS since optimal cellular functioning is crucial for providing the energy for a cell to repair itself. Interestingly, mitochondria are the major source of reactive oxygen species (ROS) and are thus particularly targeted by oxidative damage. Consequently, mitochondrial self-production of ROS causes oxidative damage that contributes to mitochondrial dysfunction and cell death.

Various antioxidants have been tested with regard to the physiological and pathological roles of ROS. Antioxidant research has provided numerous natural and designed molecules that modulate ROS with various selectivity against the different origins of ROS, being physiological (cellular signalling) or pathological. However, although ROS have been related to numerous diseases, and antioxidants have shown promises in many preclinical experiments, nearly all clinical trials of antioxidant-based therapeutics have shown limited efficacy (Orr et al, 2013. *Free Radio. Biol. Med.* 65:1047-59).

In addition, several recent studies have also demonstrated that too much reduction of ROS in cells is deleterious and it appears that an adequate balance of ROS production is necessary for cell functioning (Goodman et al., 2004. *J. Natl. Cancer Inst.* 96(23): 1743-50; Bjelakovic et al., 2007. *JAMA.* 297(8):842-57). As a consequence, there is a growing interest in the selective inhibition of ROS production by mitochondria that would not affect cellular signalling by cytosolic ROS production.

As mitochondrial oxidative damage contributes to a wide range of human diseases, antioxidants designed to be accumulated by mitochondria in vivo have been developed. The most extensively studied of these mitochondria-targeting antioxidants is MitoQ, which contains an antioxidant quinone moiety covalently attached to a lipophilic triphenylphosphonium cation. MitoQ has now been used in a range of in vivo studies in rats and mice and in two phase II human trials. Conditions of high ROS production are now better characterized. It appears that ROS may be produced at multiple sites of the respiratory chain in mitochondria (Quinlan et al., 2013. *Redox Biol.* 1:304-12). Maximal superoxide/$H_2O_2$ production occurs under conditions of high reduction of electron transporters, mainly quinones, and high values of mitochondrial membrane potential. Paradoxically, these conditions are satisfied when mitochondrial oxidative phosphorylation is low (low muscle contraction) or under low oxygen conditions (hypoxia).

The Applicant demonstrates here that AOX (desmethylanethole trithione) does not act as a classical unspecific antioxidant molecule but more interestingly as a direct selective inhibitor of the production of oxygen radicals (ROS) predominantly at site $I_Q$ of complex I of the mitochondrial respiratory chain, the main mitochondrial site of ROS production and the main responsible site for mitochondrial dysfunctions.

Therefore, the present invention relates to AOX and bio-isostere derivatives thereof to treat and/or prevent free oxygen radicals-related diseases.

SUMMARY

The present invention relates to a compound of formula (I)

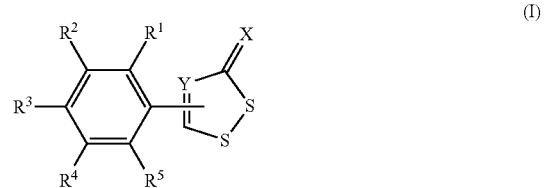

or a pharmaceutically acceptable tautomer, salt or solvate thereof wherein X, Y, $R^1$, $R^2$, $R^3$, $R^4$, $R^9$ and $R^6$ are as defined below;

for use as inhibitor of production of reactive oxygen species (ROS) in the treatment and/or prevention of free oxygen radicals-related diseases.

In one embodiment, the compound for use of the invention is selected from 5-(4-hydroxyphenyl)-3H-1,2-dithiole-3-thione; 5-(4-hydroxyphenyl)-3H-1,2-dithiol-3-one; 5-(4-hydroxyphenyl)-3H-1,2-dithiol-3-one oxime; 5-(4-hydroxyphenyl)-3H-1,2,4-dithiazole-3-thione; 4-(4-hydroxyphenyl)-3H-1,2-dithiole-3-thione; 5-(2-hydroxybenzo[d]oxazol-5-yl)-3H-1,2-dithiole-3-thione; 5-(2-hydroxybenzo[d]thiazol-6-yl)-3H-1,2-dithiole-3-thione; 5-(benzofuran-5-yl)-3H-1,2-dithiole-3-thione; and methyl 5-(3-thioxo-3H-1,2-dithiol-5-yl)-1H-indole-1-carboxylate.

In one embodiment, the compound for use of the invention is 5-(4-hydroxyphenyl)-3H-1,2-dithiole-3-thione (AOX).

In one embodiment, the compound for use of the invention is a compound of formula (II) or (III)

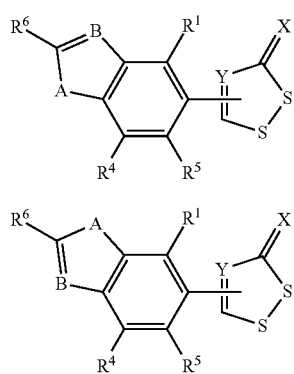

or a pharmaceutically acceptable tautomer, salt or solvate thereof, wherein X, Y, $R^1$, $R^4$, $R^5$, $R^6$, A and B are as defined below.

In one embodiment, the compound of the invention inhibits mitochondrial production of ROS. In one embodiment, the compound of the invention inhibits mitochondrial production of ROS at site $I_Q$ of complex I of mitochondria.

In one embodiment, free oxygen radicals-related diseases are selected from the group comprising cardiovascular diseases, aging diseases, auto-immune diseases, progeroid syndromes, Parkinsonian syndromes, neurological diseases, ischemic and reperfusion injuries, infectious diseases, muscles diseases, lung, kidney and liver diseases.

In one embodiment, cardiovascular diseases are selected from the group comprising myocardial infarction, cardiac toxicity (including, cardiac toxicity of anthracyclines, cardiac toxicity of anti-cancer drugs, cardiac toxicity of quinolones and cardiac toxicity of antiviral drugs, preferably, cardiac toxicity of anthracyclines), pulmonary arterial hypertension, heart failure, cardiopulmonary diseases, ischemia, heart attack, stroke, thrombosis and embolism.

In one embodiment, the compound of the invention is for preventing metastasis.

The present invention also relates to a compound of formula (I')

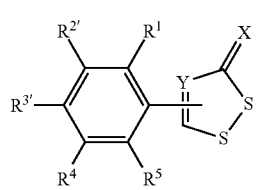

or a pharmaceutically acceptable tautomer, salt or solvate thereof, wherein X, Y, $R^1$, $R^2$, $R^3$, $R^4$, $R^5$ and $R^6$ are as defined below.

In one embodiment, the compound of the invention is of formula (IIa), (IIb), (IIIa) or (IIIb) as defined below, or a pharmaceutically acceptable tautomer, salt or solvate thereof.

In one embodiment, the compound of the invention is of formula (IIa-1), (IIa-2), (IIia-1) or (IIIa-2) as defined below, or a pharmaceutically acceptable tautomer, salt or solvate thereof.

In one embodiment, the compound of the invention is of formula (IIa-1a), (IIa-1b), (IIa-1c), (IIa-1d), (IIa-1e), (IIa-2a), (IIa-2b), (IIa-2c), (IIa-2d), (IIa-2e), (IIIa-1a), (IIIa-1b), (IIIa-1c), (IIIa-1d), (IIIa-1e), (IIIa-2a), (IIIa-2b), (IIIa-2c), (IIIa-2d) or (IIIa-2e) as defined below, or a pharmaceutically acceptable tautomer, salt or solvate thereof.

In one embodiment, the compound of the invention is of formula (IIb-1), (IIb-2), (IIb-3), (IIb-4), (IIb-5), (IIIb-1), (IIIb-2), (IIIb-3), (IIIb-4) or (IIIb-5) as defined below, or a pharmaceutically acceptable tautomer, salt or solvate thereof.

The present invention also relates to a pharmaceutical composition comprising the compound of the invention, or a pharmaceutically acceptable tautomer, salt or solvate thereof, and at least one pharmaceutically acceptable excipient.

The present invention also relates to a medicament comprising the compound of the invention or a pharmaceutically acceptable tautomer, salt or solvate thereof.

The present invention also relates to a process for manufacturing a compound of Formula (IIa-1) as defined below, or a pharmaceutically acceptable tautomer, salt or solvate thereof, characterized in that it comprises:

a) cyclizing a compound of formula (C)

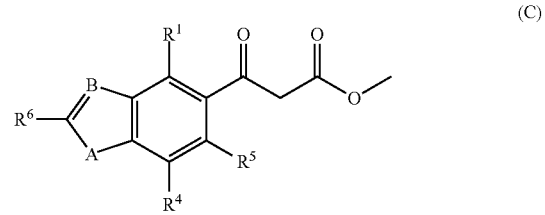

wherein A, B, $R^1$, $R^4$, $R^5$ and $R^6$ are as defined below;
with a sulfur-based reagent, in the presence of a siloxane;
to obtain a compound of formula (IIa-1')

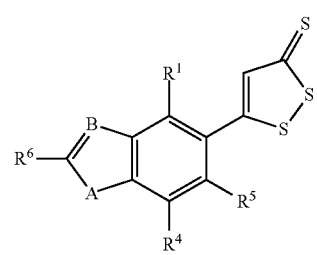

or a pharmaceutically acceptable tautomer, salt or solvate thereof, wherein A, B, $R^1$, $R^4$, $R^5$ and $R^6$ are as defined below;

and optionally:
b1) compound of formula (IIa-1') can react with an oxidant; preferably the oxidant is the mercury acetate Hg(OAc)$_2$; to obtain a compound of formula (IIa-1")

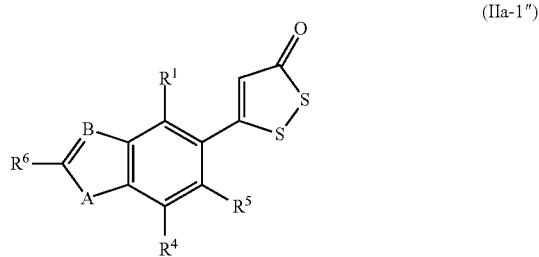

(IIa-1")

or a pharmaceutically acceptable tautomer, salt or solvate thereof, wherein A, B, R$^1$, R$^4$, R$^5$ and R$^6$ are as defined below;
or
b2) compound of formula (IIa-1') can react with hydroxylamine NH$_2$OH—HCl; in the presence of a base; preferably, the base is sodium acetate (AcONa); to obtain a compound of formula (IIa-1''')

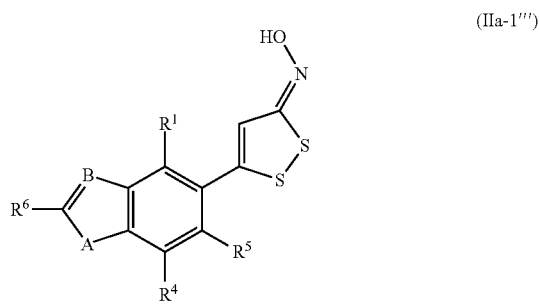

(IIa-1''')

or a pharmaceutically acceptable tautomer, salt or solvate thereof, wherein A, B, R$^1$, R$^4$, R$^5$ and R$^6$ are as defined below.

Definitions

In the present invention, the following terms have the following meanings: The term "about", preceding a figure, means plus or less 10% of the value of said figure.

The term "alkoxy" as used herein by itself or as part of another substituent refers to a group —O-alkyl wherein alkyl is as herein defined.

The term "alkyl" as used herein by itself or as part of another substituent refers to a hydrocarbyl radical of formula $C_nH_{2n+1}$ wherein n is a number greater than or equal to 1. Generally, alkyl groups of this invention comprise from 1 to 8 carbon atoms, preferably from 1 to 6 carbon atoms, more preferably from 1 to 4 carbon atoms, more preferably from 1 to 3 carbon atoms. Alkyl groups may be linear or branched. Suitable alkyl groups include methyl, ethyl, propyl, butyl, pentyl, hexyl, heptyl and octyl.

The term "alkylamino" as used herein by itself or as part of another substituent refers to a group —NH-alkyl wherein alkyl is as herein defined.

The term "alkyloxycarbonyl" as used herein by itself or as part of another substituent refers to a group —C(=O)—O-alkyl, wherein alkyl is as herein defined. A preferred alkyloxycarbonyl group is methyloxycarbonyl.

The term "alkylsulfonyl" as used herein by itself or as part of another substituent refers to a group —SO$_2$-alkyl wherein alkyl is as herein defined.

The term "amino" as used herein refers to a group —NH$_2$.

The term "aminoalkyl" as used herein by itself or as part of another substituent refers to a group -alkyl-NH$_2$ wherein alkyl is as herein defined.

The term "aminosulfonyl" as used herein by itself or as part of another substituent refers to a group —SO$_2$—NH$_2$.

The term "aryl" as used herein by itself or as part of another substituent refers to a polyunsaturated, aromatic hydrocarbyl group having a single ring (i.e., phenyl) or multiple aromatic rings fused together (e.g., naphtyl), typically containing 5 to 12 atoms; preferably 6 to 10. Non-limiting examples of aryl comprise phenyl, naphthalenyl.

The term "bio-isosteres" as used herein refers to compounds or groups that possess near-equal molecular shapes and volumes, approximately the same distribution of electrons, and which exhibit similar physical properties and similar biological activities.

The term "carboxy" as used herein refers to a group —COOH.

The term "carboxyalkyl" as used herein by itself or as part of another substituent refers to a group -alkyl-COOH wherein alkyl is as herein defined.

The term "halo" or "halogen" means fluoro, chloro, bromo, or iodo.

The term "haloalkyl" itself or as part of another substituent, refers to an alkyl radical as herein defined wherein one or more hydrogens are replaced with a halogen as herein defined. Non-limiting examples of haloalkyl include fluoromethyl, difluoromethyl and trifluoromethyl.

The term "heteroaryl" as used herein by itself or as part of another substituent refers to an aryl group as herein defined wherein at least one carbon atom is replaced with a heteroatom. In other words, it refers to 5 to 12 carbon-atom aromatic single rings or ring systems containing 2 rings which are fused together, typically containing 5 to 6 atoms; in which one or more carbon atoms is replaced by oxygen, nitrogen and/or sulfur atoms where the nitrogen and sulfur heteroatoms may optionally be oxidized and the nitrogen heteroatoms may optionally be quaternized. Non-limiting examples of such heteroaryl, include: oxazolyl, thiazolyl, imidazolyl, furanyl and pyrrolyl.

The terms "IC$_{50}$" or "half maximal inhibitory concentration" represent the concentration of an inhibitor that is required for 50% inhibition in vitro. It is comparable to an "EC$_{50}$" or "half maximal effective concentration" for agonist drugs. "EC$_{50}$" also represents the plasma concentration required for obtaining 50% of a maximum effect in vivo.

The term "nitrooxyalkyl" as used herein by itself or as part of another substituent refers to a group -alkyl-ONO$_2$ wherein alkyl is as herein defined.

The expression "pharmaceutically acceptable excipient" refers to an excipient that does not produce an adverse, allergic or other untoward reaction when administered to an animal, preferably a human. It includes any and all solvents, dispersion media, coatings, antibacterial and antifungal agents, isotonic and absorption delaying agents and the like. For human administration, preparations should meet sterility, pyrogenicity, general safety and purity standards as required by regulatory offices, such as, e.g., FDA Office or EMA.

The term "ROS", as used herein, refers to reactive oxygen species. ROS are chemically reactive chemical species containing oxygen. Examples include, but are not limited to, peroxides ($[O-O]^{2-}$ and R—O—O—R, such as $H_2O_2$), superoxide ($O_2.^-$), hydroxyl radical (.OH) and singlet oxygen ($^1O_2$). In cells, ROS are produced as a byproduct of the metabolism of oxygen; however, environmental stress can lead to an increased ROS production by cells, termed "oxidative stress", leading to significant damage to cell structures. Several distinct sites of ROS production have been identified to date, among which mitochondria (and in particular, sites $I_Q$, $I_F$, $III_{QO}$, SDH and mGPDH of the mitochondrial respiratory chain), microsomes (e.g., cytochrome P450 and diamine oxidase), peroxisomes and some enzymes in the plasma membrane (e.g., NADPH oxidase and lipooxygenase). Depending on the location within the cell where ROS are released and stored, one may further distinguish between "cytosolic ROS" and "mitochondrial ROS". For example, complex I of the mitochondrial respiratory chain (sites $I_Q$ and $I_F$) and site SDH of the mitochondrial complex II produce and release ROS toward the mitochondrial lumen which are therefore considered as "mitochondrial ROS"; whereas complex III of the mitochondrial respiratory chain (site $III_{QO}$) and site mGPDH produce and release ROS toward the cell cytoplasm which are considered as "cytosolic ROS".

The term "salt" of the compounds of the invention is used herein to describe the acid addition and base salts thereof. Suitable acid addition salts are formed from acids which form non-toxic salts. Non-limiting examples include the acetate, trifluoroacetate, adipate, aspartate, benzoate, besylate, bicarbonate/carbonate, bisulphate/sulphate, borate, tetrafluoroborate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts. Suitable base salts are formed from bases which form non-toxic salts. Non-limiting examples include the aluminium, arginine, benzathine, calcium, choline, diethylamine, diolamine, glycine, lysine, magnesium, meglumine, olamine, potassium, sodium, tromethamine, 2-(diethylamino)ethanol, ethanolamine, morpholine, 4-(2-hydroxyethyl)morpholine and zinc salts. Hemisalts of acids and bases may also be formed, for example, hemisulphate and hemicalcium salts. Preferred, pharmaceutically acceptable salts include hydrochloride/chloride, hydrobromide/bromide, bisulphate/sulphate, nitrate, citrate, and acetate.

The term "site $I_Q$", as used herein, refers to the ubiquinone binding site of the NADH:ubiquinone oxidoreductase (also known as mitochondrial complex I). Site $I_Q$ produces ROS which are released inside the mitochondrial lumen.

The term "site $I_F$", as used herein, refers to the flavin binding site of mitochondrial complex I. Site $I_F$ produces ROS which are released inside the mitochondrial lumen.

The term "site $III_{QO}$", as used herein, refers to the ubiquinone binding site of the cytochrome bc1 complex (also known as mitochondrial complex II). Site $III_{QO}$ produces ROS which are released toward the cell cytoplasm.

The term "site SDH", as used herein, refers to succinate dehydrogenase (also known as mitochondrial complex II). Site SDH produces ROS which are released inside the mitochondrial lumen.

The term "site mGPDH", as used herein, refers to glycerol 3-phosphate dehydrogenase. Site mGPDH produces ROS which are released toward the cell cytoplasm.

The term "solvate" is used herein to describe a compound in this invention that contains stoichiometric or sub-stoichiometric amounts of one or more pharmaceutically acceptable solvent molecule such as ethanol or water. The term "hydrate" refers to when the said solvent is water.

The term "subject" refers to an animal, including a human. In the sense of the present invention, a subject may be a patient, i.e., a person receiving medical attention, undergoing or having underwent a medical treatment, or monitored for the development of a disease. In one embodiment, the subject is a male. In another embodiment, the subject is a female.

The term "tautomer" refers to organic compounds that are interconvertible by a chemical reaction called tautomerization. Said chemical reaction involves the migration of a hydrogen atom or proton, accompanied by a switch of a single bond and adjacent double bond.

The expression "therapeutically effective amount" means level or amount of agent that is aimed at, without causing significant negative or adverse side effects to the target, (1) delaying or preventing the onset of a disease, disorder, or condition related to free oxygen radicals; (2) slowing down or stopping the progression, aggravation, or deterioration of one or more symptoms of the disease, disorder, or condition related to free oxygen radicals; (3) bringing about ameliorations of the symptoms of the disease, disorder, or condition related to free oxygen radicals; (4) reducing the severity or incidence of the disease, disorder, or condition related to free oxygen radicals; or (5) curing the disease, disorder, or condition related to free oxygen radicals. A therapeutically effective amount may be administered prior to the onset of the disease, disorder, or condition related to free oxygen radicals, for a prophylactic or preventive action. Alternatively or additionally, the therapeutically effective amount may be administered after initiation of the disease, disorder, or condition related to free oxygen radicals, for a therapeutic action.

The terms "treating", "treatment" or "alleviation" refer to both therapeutic treatment and prophylactic or preventative measures; wherein the object is to prevent or slow down the targeted pathologic condition or disease. Those in need of treatment include those already with the disease as well as those prone to have the disease or those in whom the disease is to be prevented. A subject or mammal is successfully "treated" for a disease or affection or condition if, after receiving the treatment according to the present invention, the subject or mammal shows observable and/or measurable reduction in or absence of one or more of the following: reduction ROS production; and/or relief to some extent, for one or more of the symptoms associated with the specific disease or condition; reduced morbidity and mortality, and improvement in quality of life issues. The above parameters for assessing successful treatment and improvement in the disease are readily measurable by routine procedures familiar to a physician.

DETAILED DESCRIPTION

One object of the present invention is a method for treating and/or preventing; or for the treatment and/or prevention of free oxygen radicals-related diseases in a subject in need thereof comprising the administration of an effective amount of an inhibitor of mitochondrial production of reactive oxygen species (ROS).

Another object of the present invention is an inhibitor of mitochondrial production of reactive oxygen species (ROS) for treating and/or preventing; or for use in treating and/or preventing free oxygen radicals-related diseases, wherein said inhibitor inhibits mitochondrial production of ROS.

In one embodiment, the inhibitor of the invention does not affect physiological (cytosolic) ROS production. In one embodiment, the physiological (cytosolic) ROS production is not modulated by more than 5% (increase or decrease) in presence of the inhibitor of the invention. In one embodiment, the physiological (cytosolic) ROS production is not modulated by more than 2%, 4%, 6%, 8%, 10%, 12%, 14%, 16%, 18%, 20%, 25%, 30%, 35%, 40%, 45%, 50% (increase or decrease) in presence of the inhibitor of the invention.

The term "does not affect" as used herein refers to an absence of effect of the inhibitor of the invention measured by technics known to the skilled artisan for determining the level of ROS production.

In another embodiment, the inhibitor of the invention is not an inhibitor of cytosolic ROS production.

In one embodiment, the inhibitor of the invention does not affect physiological (cytosolic) ROS production at at least one site selected from $III_{QO}$ and mGPDH.

In one embodiment, the inhibitor of the invention does not decrease physiological (cytosolic) ROS production from at least one site selected from $III_{QO}$ and mGPDH by greater than 2%, 4%, 6%, 8%, 10%, 12%, 14%, 16%, 18%, 20%, 25%, 30%, 35%, 40%, 45%, 50% or more.

In a preferred embodiment, the inhibitor of the invention does not decrease physiological (cytosolic) ROS production from site $III_{QO}$ of complex III of the mitochondrial respiratory chain.

Cytosolic ROS production is determined by the difference between total cellular ROS production and internal mitochondrial ROS production. Alternatively, cytosolic ROS production can be determined in an in vitro assay of NAD(P)H oxidase ROS production.

In another embodiment, the inhibitor of the invention acts upstream from ROS production.

Tests to detect cytosolic ROS production are well-known in the state of the art and to the skilled artisan.

Examples of such tests include, but are not limited to:

(1) Measurement of Global Cellular ROS Production:

5-(and-6)-chloromethyl-2',7'-dichlorodihydrofluorescein diacetate, acetyl ester (CM-H$_2$DCFDA) and/or H$_2$DCFDA are indicators for cytosolic reactive oxygen species (ROS) in cells. CM-H$_2$DCFDA passively diffuses into cells, where its acetate groups are cleaved by intracellular esterases and its thiol-reactive chloromethyl group reacts with intracellular glutathione and other thiols. Subsequent oxidation yields a fluorescent adduct that is trapped inside the cell, thus facilitating long-term studies (Zhang et al., 2008. *J. Cardiovasc. Pharmacol.* 51(5):443-9; Sarvazyan, 1996. *Am. J. Physiol.* 271(5 Pt 2):H2079-2085).

(2) Measurement of Mitochondrial ROS Production in Cells:

Measuring intracellular ROS in intact cells and assigning the origin to mitochondria are far more difficult. In recent years, the proton-motive force crucial to mitochondrial function has been exploited to target a variety of compounds to the highly negative mitochondrial matrix using the lipophilic triphenylphosphonium cation TPP$^+$ as a "delivery" conjugate. Among these, MitoSOX Red, also called mitohydroethidine or mito-dihydroethidium, is prevalently used for mitochondrial ROS estimation. The TPP$^+$ moiety of MitoSOX enables the manifold accumulation of ROS-sensitive hydroethidine in the mitochondrial matrix and the oxidation of hydroethidine by superoxide gives rise to a specific fluorescent oxidation product, 2-hydroxyethidium (Zhao et al., 2005. *Proc. Natl. Acad. Sci. USA.* 102(16): 5727-5732; Polster et al., 2014. *Methods Enzymol.* 547:225-250).

In one embodiment, the inhibitor of the invention is a selective inhibitor of mitochondrial production of reactive oxygen species (ROS).

In one embodiment, the inhibitor of the invention is a selective inhibitor of mitochondrial production of ROS at at least one site selected from $I_Q$, $I_F$ and SDH.

In one embodiment, a selective inhibitor of mitochondrial production according to the present invention decrease mitochondrial ROS production from at least one site selected from $I_Q$, $I_F$ and SDH by greater than 2%, 4%, 6%, 8%, 10%, 12%, 14%, 16%, 18%, 20%, 25%, 30%, 35%, 40%, 45%, 50% or more, while affecting mitochondrial ROS production from the remaining sites of ROS production by less than 50%, 45%, 40%, 35%, 30%, 25%, 20%, 18%, 16%, 14%, 12%, 10%, 8%, 6%, 4%, 2% or less.

In one embodiment, inhibitors that are selective inhibitors of mitochondrial ROS production from a single site of mitochondrial ROS production decrease ROS production from one of the ROS production site $I_Q$, $I_F$ or SDH by greater than 18%, while affecting ROS production from the remaining sites of ROS production by less than 10%.

In a preferred embodiment, the inhibitor of the invention is a selective inhibitor of mitochondrial production of ROS at site $I_Q$ and/or $I_F$ of complex I of the mitochondrial respiratory chain.

Complex I of the mitochondrial respiratory chain can generate ROS from two distinct sites: the ubiquinone binding site and the flavin mononucleotide site.

Ubiquinone Binding Site of Complex I ($I_Q$):

To specifically analyze ROS production from $I_Q$, 5 mM succinate may be used as the substrate to supply electrons to the respiratory chain. $I_Q$ ROS production is exceptionally sensitive to changes in the proton motive force (PMF) across the mitochondrial inner membrane (PMF=$\Delta\Psi m + \Delta pH$). Therefore, a conservative threshold for the $\Delta\Psi m$ assay when evaluating selectivity of hits in the $I_Q$ ROS assay may be utilized.

Electron leak from site $I_Q$ is best characterized during reverse transport from a reduced Q-pool to matrix NAD$^+$ via CI in the presence of a strong PMF. Experimentally, conditions that favor $I_Q$ ROS production are considered far removed from physiology leading many to dismiss its relevance despite its capacity for high rates. However, even when provided with lower concentrations of both glutamate (to feed electrons forward through CI) and succinate (to feed electrons in reverse), respiring mitochondria still produce significant levels of rotenone-sensitive ROS (i.e., $I_Q$ ROS). Further, comparative analyses show an inverse relationship between maximal ROS production from site $I_Q$ (but not site $I_F$) and maximum life span across diverse vertebrate species (Lambert et al., 2007. *Aging Cell.* 6(5):607-18; Lambert et al., 2010. *Aging Cell.* 9(1):78-91). Therefore, selective modulators of $I_Q$ ROS would offer unique opportunities to probe the putative role of mitochondrial ROS production in normal and pathological processes.

Flavin Binding Site of Complex I ($I_F$):

To specifically analyze ROS production from $I_F$, the substrate solution to supply electrons to the respiratory chain may comprise 5 mM glutamate, 5 mM malate and 4 μM rotenone. Site $I_F$ produces ROS at a rate proportional to the reduction state of the NADH pool in the mitochondrial matrix (Treberg et al., 2011. *J. Biol. Chem.* 286(36):31361-

72). Blockade of site $I_Q$ with the pesticide rotenone can increase ROS production from site $I_F$ by preventing oxidation of the flavin. Maximal ROS production from the flavin binding site of complex I (site $I_F$) is relatively low compared to sites $I_Q$ and $III_{QO}$ and this may lead to higher variability in this assay and subsequently a higher false positive rate of hit calling in the original screen.

Inhibition of complex I activity by rotenone and the neurotoxin MPP+ has been linked to parkinsonism in both rodents and humans, suggesting a link between dysfunctional complex I, ROS production, and neurodegeneration. Compounds that are capable of inhibiting ROS production from complex I may therefore be useful in therapy.

In another embodiment, the inhibitor or selective inhibitor of the invention is a selective inhibitor of mitochondrial production of reactive oxygen species (ROS) production at site $I_Q$ of complex I of the mitochondrial respiratory chain.

The term "selective inhibitor" as used herein can refer to a compound capable of inhibiting ROS production at site $I_Q$ of complex I, while having minimal effects on ROS production from the remaining sites and on mitochondrial membrane potential (ΔΨm) and oxidative phosphorylation. For example, on isolated mitochondria, in the presence of rotenone (i.e., when ROS production at site $I_Q$ is inhibited) and antimycin A (i.e., when ROS are produced mainly by complex III), the $IC_{50}$ of the compound on the inhibition of ROS production is about 5, 6, 7, 8, 9, 10, 15, 20 times higher than in the absence of rotenone.

In one embodiment, the term "selective inhibitor" as used herein can also refer, exclusively or inclusively with any one of the definitions given herein, to a compound capable of inhibiting mitochondrial ROS production at site $I_Q$ of complex I with an $IC_{50}$ ranging from about 0.1 μM to about 20 μM, preferably of about 10 μM. In one embodiment, the term "selective inhibitor" as used herein can also refer, exclusively or inclusively with any one of the definitions given herein, to a compound capable of inhibiting mitochondrial ROS production at site $I_Q$ of complex I with an $IC_{50}$ of about 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20 μM. In another embodiment, said compound does not significantly inhibit cytosolic ROS production in an in vitro assay of NAD(P)H oxidase ROS production.

The term "selective inhibitor" as used herein can also refer, exclusively or inclusively with any one of the definitions given herein, to a compound capable of inhibiting ROS production at site $I_Q$ of complex I, while having minimal effects on ROS production from the remaining sites and on mitochondrial membrane potential (ΔΨm) and oxidative phosphorylation. For example, on isolated mitochondria, in the presence of rotenone (i.e., when ROS production at site $I_Q$ is inhibited), the $IC_{50}$ of the compound on the inhibition of ROS production is about 5, 6, 7, 8, 9, 10, 15, 20 times higher or more than in the presence of antimycin A (i.e., added after rotenone, therefore when ROS are produced mainly by complex III).

Tests to specifically detect ROS produced at site $I_Q$ of complex I of the mitochondrial respiratory chain on isolated mitochondria from various tissues are well-known to the skilled artisan.

High-throughput assays for the identification of inhibitors of ROS production at defined sites in isolated mitochondria without also altering energy production are also described. The assays identify site-specific modulators of ROS production while also revealing less specific effectors like broad-acting antioxidants and various inhibitors of mitochondrial bioenergetics. Accordingly, inhibitors that discriminate between unwanted electron leak onto oxygen (ROS production) at specific sites within the electron transport chain without altering the normal energy-coupled electron and proton fluxes across the inner mitochondrial membrane may be identified. Assays adapt standard fluorescence-based assays of mitochondrial ROS production using the dye Amplex UltraRed (Invitrogen) and ΔΨm using the potentiometric dye TMRM (Invitrogen) to a high throughput microplate format. A core set of five ROS and one ΔΨm assays for robust detection of functional modulation in freshly isolated skeletal muscle mitochondria are provided. Five major sites of ROS production (site $I_Q$, $I_F$, $III_{QO}$, SDH and mGPDH) may be targeted separately by varying the substrates and inhibitors added to a common assay mixture. A counter-screen to monitor ΔΨm may be run in parallel to eliminate compounds that are likely general inhibitors or uncouplers of normal mitochondrial energy production.

In another embodiment, inhibitors are tested at 2.5 μM in duplicate against all assays. Endpoint fluorescence is normalized to DMSO and known mitochondrial inhibitor control wells included on each plate. Positive hits in each ROS assay may be initially filtered by applying a threshold of preferably 15% or more preferably 18% or even more preferably 20% or more reduction in that assay. Each ROS assay may be employed as a counter-screen against the others while also eliminating compounds that altered ΔΨm in the TMRM-based counter-screen. Therefore, filtered hits may be subsequently assessed to eliminate those that altered the other ROS assays by more than e.g., 20% or 18% or 15% or ΔΨm by more than, preferably 10% or more preferably 5% or even more preferably 4%.

In another embodiment, the inhibitor of the invention does not affect significantly oxidative phosphorylation directly on mitochondria, preferably oxidative phosphorylation is modulated by less than 10, 9, 8, 7, 6, 5%.

Free oxygen radicals-related diseases relate to oxidative stress imbalances and mitochondrial dysfunction. In particular, diseases related to mitochondrial dysfunctions are induced by mitochondrial ROS production.

Free oxygen radicals-related diseases include, but are not limited to, cardiovascular diseases, aging diseases, autoimmune diseases, progeroid syndromes, Parkinsonian syndromes, neurological diseases, ischemic and reperfusion injuries, infectious diseases, muscles diseases, lung, kidney and liver diseases.

Free oxygen radicals-related cardiovascular diseases include, but are not limited to, hypertension, cardiac toxicity (including, cardiac toxicity of anthracyclines, cardiac toxicity of anti-cancer drugs, cardiac toxicity of quinolones and cardiac toxicity of antiviral drugs), heart failure regardless of origin, ischemia, myocardial infarction, heart attack, stroke, atherosclerosis, cardiac fibrillation, hypertension, thrombosis and embolism, allergic/inflammatory conditions such as bronchial asthma, rheumatoid arthritis, inflammatory Bowel disease, type II diabetes, diabetes mellitus and deafness (DAD, also known as Ballinger-Wallace syndrome), inflammatory diseases, rheumatic fever, pulmonary arterial hypertension, syndromic cardiomyopathies (such as, Barth syndrome, Costello syndrome, Friedreich ataxia, LEOPARD syndrome, Noonan syndromes, cardiofaciocutaneous syndrome, cardioencephalomyopathy and Alstrom syndrome), innate immune responses and cardiopulmonary diseases such as chronic obstructive pulmonary disease, pulmonary embolism, pericarditis, coarctation of aorta, tetralogy of Fallot, aortic stenosis, mitral stenosis, aortic regurgitation, mitral regurgitation, pneumoconiosis, bronchiectasis, cardiomyopathies and/or endothelial nitroglycerin tolerance.

Free oxygen radicals-related aging diseases include, but are not limited to, age-related macular degeneration (AMD), skin ageing, UV damage to the skin, thinning, sagging, wrinkling, the appearance of age spots, broken blood vessels and areas of dryness, seborrhoeic keratosis, solar keratoses, Kindler Syndrome, Bowen's disease, skin cancer, arthritis, ankylosing spondylitis, inflammatory polyarthropathies, knee arthritis, epidemic polyarthritis, psoriatic arthritis, cataract, deafness, cancer, metastasis, metastasis processes prevention, liver diseases, transplantation, neoplasms and toxicity of anti-neoplastic or immunosuppressive agents and chemicals, osteoporosis, poikiloderma, acrogeria, hereditary sclerosing poikiloderma, dyskeratosis congenita, xeroderma pigmentosum, Bloom's syndrome, Fanconi anemia, Cockayne syndrome and pollution-induced diseases.

Free oxygen radicals-related autoimmune diseases include, but are not limited to, multiple sclerosis, rheumatoid arthritis, systemic lupus erythematosis, type I diabetes mellitus, Crohn's disease; myasthenia gravis, Grave's disease, scleroderma, Sjogren's syndrome, ulcerative colitis, primary biliary cirrhosis, autoimmune hepatitis, Hashimoto's thyroiditis, ankylosing spondylitis, psoriasis.

The autoimmune disease can be an autoimmune disease related to blood disorders such as autoimmune hemolytic anemia, pernicious anemia and autoimmune thrombocytopenia.

The autoimmune disease can also be temporal arteritis, anti-phospholipid syndrome, vasculitides such as Wegener's granulomatosis and Behcet's disease.

Other autoimmune diseases include polymyositis, dermatomyositis, spondyloarthropathies such as ankylosing spondylitis, anti-phospholipid syndrome and polymyocysitis.

Free oxygen radicals-related progeroid syndromes include, but are not limited to, progeria, Bloom syndrome, Cockayne syndrome, De Barsy syndrome, dyskeratosis congenita, restrictive dermopathy, Rothmund-Thomson syndrome, trichothiodystrophy, Werner syndrome, Wiedemann-Rautenstrauch syndrome and xeroderma pigmentosum.

Free oxygen radicals-related parkinsonian syndromes include, but are not limited to, Parkinson's disease (PD), progressive supranuclear palsy, multiple system atrophy, corticobasal degeneration or Lewy body dementia, toxin-induced Parkinsonism, and an early-onset variant of PD such as an autosomal recessive PARK6-linked Parkinsonism or an autosomal recessive PINK1-linked Parkinsonism.

Free oxygen radicals-related neurologic diseases include, but are not limited to, dementia, Alzheimer's disease, Parkinson's disease and ageing, Huntington's disease, Friedreich's Ataxia, Wilson's disease, Leigh syndrome, Kearns-Sayre syndrome, Leber hereditary optic neuropathy, cognitive disorders, mood disorders, movement disorders, tardive dyskinesia, brain injury, apoptosis, dementia, epilepsy, epileptic dementia, presenile dementia, post traumatic dementia, senile dementia, vascular dementia, HIV-1-associated dementia, post-stroke dementia, schizophrenia, Down's syndrome, motor neuron disease, amyloidosis, amyloid associated with type II diabetes, Creutzfelt-Jakob disease, necrotic cell death, Gerstmann-Straussler syndrome, kuru and animal scrapie, amyloid associated with long-term hemodialysis, senile cardiac amyloid and familial amyloidotic polyneuropathy, cerebropathy, neurospanchnic disorders, memory loss, aluminum intoxication, reducing the level of iron in the cells of living subjects, reducing free transition metal ion levels in mammals, patients having toxic amounts of metal in the body or in certain body compartments, multiple sclerosis, amyotrophic lateral sclerosis, akinetopsia, alcohol-related dementia, primary age-related tauopathy, anomic aphasia, anosognosia, apraxia, apraxia of speech, auditory verbal agnosia, frontotemporal dementia, frontotemporal lobar degeneration, logopenic progressive aphasia, neurofibrillary tangle, phonagnosia, Pick's disease, primary progressive aphasia, progressive nonfluent aphasia, semantic dementia, steroid dementia syndrome, visuospatial dysgnosia, ototoxic secondary effects of aminoglycosides and cocaine toxicity.

Free oxygen radicals-related ischemic and reperfusion injury include, but are not limited to, stroke, brain ischemia, brainstem stroke syndrome, carotid endarterectomy, cerebellar stroke syndrome, cerebral achromatopsia, cerebral hemorrhage, cerebral infarction, cerebral venous sinus thrombosis, intraparenchymal hemorrhage, intracranial hemorrhage, lacunar stroke, lateral medullary syndrome, lateral pontine syndrome, partial anterior circulation infarct, posterior circulation infarct, silent stroke, stroke Association, stroke belt, stroke recovery, transient ischemic attack, Watershed stroke, Weber's syndrome, obesity, organ preservation for transplantation, ischemia and reperfusion injury.

Free oxygen radicals-related infectious diseases include, but are not limited to, hepatitis C, sepsis, infectious myopathies and septic shock.

Free oxygen radicals-related muscles diseases include, but are not limited to, myopathies, mitochondrial myopathies, facioscapulohumeral muscular dystrophy, facioscapulohumeral muscular dystrophy type 1, facioscapulohumeral muscular dystrophy type 2, Ryanodine Receptor 1 (RYR1) related myopathy, selenoprotein 1 (SEPN1)-related myopathy Kearns-Sayre syndrome, cardiomyopathies, movement disorder, immobilization-induced muscle atrophy, skeletal muscle burn injury and Dupuytren's contracture.

Free oxygen radicals-related lung, kidney and liver diseases include, but are not limited to, cystic fibrosis, asthma, pollution-induced diseases, cardio-pulmonary diseases, pulmonary arterial hypertension, chronic obstructive pulmonary disease, pulmonary embolism, pneumoconiosis, bronchiectasis, bronchial asthma, ventilator-induced diaphragm dysfunction, lung cancer, alcohol fatty liver disease, fatty liver disease, diabetes, kidney preservation ex vivo, liver inflammation in hepatitis C, kidney damage in type I diabetes and cirrhosis.

In one embodiment, diseases to be treated in particular in the present invention are age-related macular degeneration, Parkinson's disease, Alzheimer's disease, ischemic and reperfusion injury, pulmonary arterial hypertension, scleroderma, atherosclerosis, heart failure, myocardial infarction, arthritis, pulmonary toxicity, cardiopulmonary diseases, inflammatory diseases, cancer, metastasis, cardiac toxicity (including, cardiac toxicity of anthracyclines, cardiac toxicity of anti-cancer drugs, cardiac toxicity of quinolones and cardiac toxicity of antiviral drugs), heart failure regardless of origin, ischemia, heart attack, stroke, thrombosis and embolism, asthma, allergic/inflammatory conditions, bronchial asthma, rheumatoid arthritis, Inflammatory Bowel Disease, Huntington's disease, cognitive disorders, Progeria, progeroid syndromes, epileptic dementia, presenile dementia, post traumatic dementia, senile dementia, vascular dementia, HIV-1-associated dementia, post-stroke dementia, Down's syndrome, motor neuron disease, amyloidosis, amyloid associated with type 11 diabetes, Creutzfelt-Jakob disease, necrotic cell death, Gerstmann-Straussler syndrome, kuru and animal scrapie, amyloid associated with long-term hemodialysis, senile cardiac amyloid and Familial Amyloidotic Polyneuropathy, cerebropathy, neurospanchnic disorders, memory loss, aluminum intoxication, reducing the level of iron in the cells of living subjects, reducing free transition metal ion levels in mammals, patients having toxic amounts of metal in the body or in certain body compartments, multiple sclerosis, amyotrophic lateral sclerosis, cataract, diabetes, cancer, liver diseases, skin ageing, transplantation, ototoxic secondary effects of aminoglycosides, neoplasms and toxicity of anti-neoplastic or immunosuppressive agents and chemicals, innate immune responses, and, Friedreich's Ataxia.

In one embodiment, diseases to be treated in particular in the present invention are free oxygen-radicals related cardiovascular diseases selected from the group comprising myocardial infarction, cardiac toxicity (including, cardiac toxicity of anthracyclines, cardiac toxicity of anti-cancer drugs, cardiac toxicity of quinolones and cardiac toxicity of antiviral drugs, preferably, cardiac toxicity of anthracyclines), pulmonary arterial hypertension, heart failure, cardiopulmonary diseases, ischemia, heart attack, stroke, thrombosis and embolism.

In one embodiment, diseases to be treated in particular in the present invention are aging disease, AMD, skin aging, cardiovascular diseases such as, e.g., cardiac toxicity of anthracyclines, progeria and progeroid syndromes, Parkinson's disease, Alzheimer's disease, Friedreich's Ataxia, ischemia reperfusion, cardio-pulmonary diseases, asthma, cancer, metastasis and/or pollution-induced diseases.

In one embodiment, a disease to be particularly prevented and/or treated in the present invention is cardiac toxicity, preferably cardiac toxicity of anthracyclines. A mechanism responsible for anthracyclines toxicity refers to ROS production and site-specific DNA damage. Oxidative stress induction plays indeed a role in cardiac toxicity of anthracyclines by inducing DNA damage, sarcomere damage, mitochondrial dysfunction and loss of pro-survival signaling, mediating both death and survival of cardiomyocytes (Valcovici et al., 2016. *Arch. Med. Sci.* 12(2):428-435).

In one embodiment, a disease to be particularly prevented and/or treated in the present invention is pulmonary hypertension. Indeed, the deleterious effect of agents promoting ROS generation on pulmonary vasculature has been shown, and conversely, the beneficial effect of antioxidant agents in animal models of pulmonary hypertension. ROS production has thus been directly linked to pulmonary vascular remodeling, endothelial dysfunction, altered vasoconstrictive responses, inflammation and modifications of the extracellular matrix, all important features of pulmonary hypertension pathophysiology (Freund-Michel et al., 2013. *Ther. Adv. Respir. Dis.* 7(3):175-200).

In one embodiment, a disease to be particularly prevented and/or treated in the present invention is ischemic and reperfusion injury. Indeed, excess production of ROS is a critical factor in the genesis of reperfusion injury (Granger et al., 2015. *Redox Biol.* 6:524-51).

In one embodiment, a disease to be particularly prevented and/or treated in the present invention is diabetes. Indeed, chronic hyperglycemia and subsequent augmentation of reactive oxygen species (ROS) deteriorate cell function and increase insulin resistance which leads to the aggravation of type 2 diabetes (Kaneto et al. 2010. *Mediators Inflamm.*, 2010:453892), but also of other types of diabetes, such as MODY (Maturity Onset Diabetes of the Young).

In one embodiment, a disease to be particularly prevented and/or treated in the present invention is Parkinson disease. Indeed, mitochondrial dysfunction and oxidative damage, which results in increased production of ROS, are conditions often found in damaged brain areas of Parkinson's disease (Muñoz et al., 2016. *Parkinsons Dis.* 2016:7049108).

In one embodiment, a disease to be particularly prevented and/or treated in the present invention is macular degeneration. Indeed, excessive ROS production and accumulation together with the oxidative stress, in particular in retinal pigment epithelium cells, plays a role in macular degeneration pathogenesis. ROS levels increase in the aging retina, leading to the oxidative stress and result in damage of photoreceptors, retinal pigment epithelium cells, and choriocapillaris in apoptosis process (Nita et al., 2016. *Oxid. Med. Cell. Longev.* 2016:3164734).

In one embodiment, a disease to be particularly prevented and/or treated in the present invention is scleroderma. Indeed, NADPH oxidase, an important source of ROS, has been shown to be upregulated in scleroderma fibroblasts, resulting in large accumulations of ROS, which in turn plays a critical role in cell activation and DNA damage (Spadoni et al., 2015. *Arthritis Rheumatol.* 67(6):1611-22).

In one embodiment, a disease to be particularly prevented and/or treated in the present invention is metastasis. Indeed, ROS production is involved in mechanisms of tumor growth and metastasis: tumor cell migration, invasion, clonogenicity, metastatic take, and spontaneous metastasis are promoted by the natural selection of a mitochondrial phenotype associated with ROS production and aberrant TCA cycle activity, a mechanism named "metastatic mitochondrial switch" (Porporato et al., 2014. *Cell Reports.* 8(3):754-766). ROS hyper production also promotes angiogenesis and reciprocally inhibitors of ROS production are antiangiogenic products.

According to one embodiment, the inhibitor or selective inhibitor of the invention is AOX or a derivative thereof.

AOX corresponds to desmethylanethole trithione, also named 5-(4-hydroxyphenyl)-3H-1,2-dithiole-3-thione:

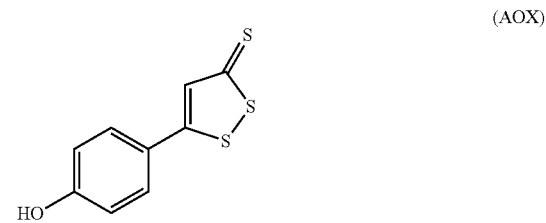 [SMILES: Oc1ccc(-c2cc(=S)ss2)cc1]

(AOX)

According to one embodiment, the derivatives of AOX are bio-isosteres thereof, preferably phenol bio-isosteres thereof.

In one embodiment, phenol bio-isosteres are for example the following groups, tautomers and optionally substituted derivatives thereof:

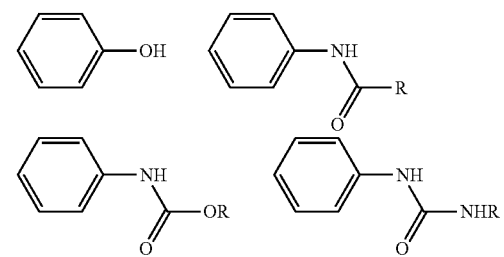

-continued

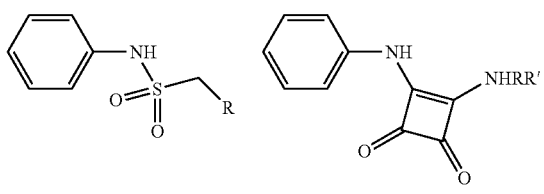

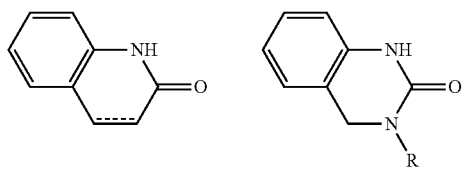

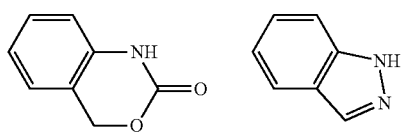

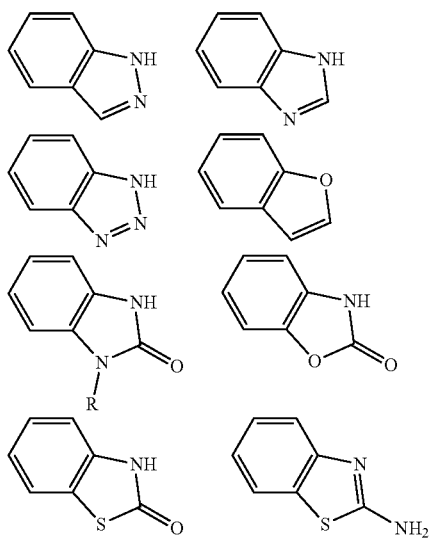

In a specific embodiment, preferred phenol bio-isosteres of the invention are those below, tautomers and optionally substituted derivatives thereof:

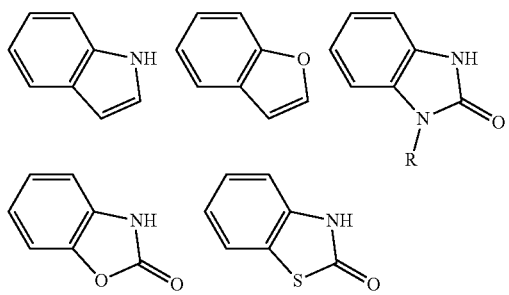

According to a preferred embodiment, the inhibitors of the invention are thus compounds of formula (I)

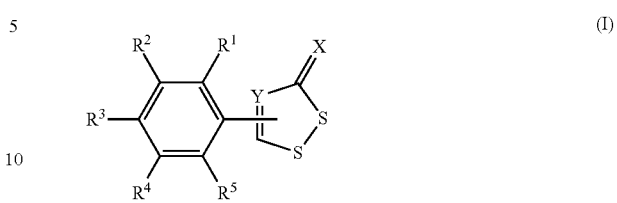

(I)

or a pharmaceutically acceptable tautomer, salt or solvate thereof wherein:
X represents S, O or NHOH; preferably X is S or O; more preferably, X is S;
Y represents CH, C or N; preferably Y is CH or N; more preferably Y is CH;
$R^1$, $R^2$, $R^4$ and $R^5$ each independently represent hydrogen, hydroxy, halo, amino, alkylsulfonyl, aminosulfonyl, cyano, nitro, carboxy, aryl, alkoxy, haloalkyl, alkylamino, aminoalkyl, nitrooxyalkyl or carboxyalkyl;
$R^3$ is hydroxy; or $R^3$ and $R^2$ together with the carbon atoms to which they are attached form a 5-membered heteroaryl moiety wherein —$R^3$—$R^2$— represents -A-$CR^6$=B— or —B=$CR^6$-A—; wherein:
A represents O, S or $NR^7$; wherein $R^7$ represents hydrogen, C1-C8 alkyl or alkyloxycarbonyl;
B represents CH or N; and
$R^6$ represents hydrogen, hydroxy, halo, amino, alkylsulfonyl, aminosulfonyl, cyano, nitro, carboxy, aryl, alkoxy, haloalkyl, alkylamino, aminoalkyl, nitrooxyalkyl or carboxyalkyl.

According to a preferred embodiment, in formula (I):
X represents S, O or NHOH; preferably X is S;
Y represents CH, C or N; preferably Y is CH;
$R^1$, $R^2$, $R^4$ and $R^5$ each independently represent hydrogen, hydroxy, halo, amino, alkylsulfonyl, aminosulfonyl, cyano, nitro, carboxy, aryl, alkoxy, haloalkyl, alkylamino, aminoalkyl, nitrooxyalkyl or carboxyalkyl; preferably $R^1$, $R^2$, $R^4$ and $R^5$ represent hydrogen;
$R^3$ is hydroxy; or $R^3$ and $R^2$ together with the carbon atoms to which they are attached form a 5-membered heteroaryl moiety wherein —$R^3$—$R^2$— represents -A-$CR^6$=B—; wherein
A represents O, S or $NR^7$; wherein $R^7$ represents hydrogen or C1-C8 alkyl group;
B represents CH or N; and
$R^6$ represents hydrogen, hydroxy, halo, amino, alkylsulfonyl, aminosulfonyl, cyano, nitro, carboxy, aryl, alkoxy, haloalkyl, alkylamino, aminoalkyl, nitrooxyalkyl or carboxyalkyl;

According to a preferred embodiment, X represents S. According to another preferred embodiment, X represents O. According to a preferred embodiment, Y represents CH. According to another preferred embodiment, Y represents N.
According to a preferred embodiment, $R^3$ and $R^2$ together with the carbon atoms to which they are attached form a 5-membered heteroaryl moiety, wherein —$R^3$—$R^2$— represents -A-$CR^6$=B—; wherein:
A represents O, S or $NR^7$; wherein $R^7$ represents hydrogen, C1-C8 alkyl or alkyloxycarbonyl; preferably $R^7$ represents hydrogen or alkyloxycarbonyl;
B represents CH or N; and
$R^6$ represents hydrogen, hydroxy, halo, amino, alkylsulfonyl, aminosulfonyl, cyano, nitro, carboxy, aryl, alkoxy, haloalkyl, alkylamino, aminoalkyl, nitrooxyalkyl or carboxyalkyl; preferably $R^6$ represents hydrogen or hydroxyl.

More preferably, —R³—R²— represents —O—C(OH)=N— or —N(COOMe)-CH=CH—, more preferably —R³—R²— represents —O—C(OH)=N—.

According to another preferred embodiment, R³ and R² together with the carbon atoms to which they are attached form a 5-membered heteroaryl moiety wherein —R³—R²- represents —B=CR⁶-A—; wherein
  A represents O, S or NR⁷; wherein R represents hydrogen, C1-C8 alkyl or alkyloxycarbonyl; preferably R⁷ represents hydrogen or alkyloxycarbonyl;
  B represents CH or N; and
  R⁶ represents hydrogen, hydroxy, halo, amino, alkylsulfonyl, aminosulfonyl, cyano, nitro, carboxy, aryl, alkoxy, haloalkyl, alkylamino, aminoalkyl, nitrooxyalkyl or carboxyalkyl; preferably R⁶ represents hydrogen or hydroxyl.

More preferably, —R³—R²— represents —N=C(OH)—S—.

According to a preferred embodiment, the inhibitors of the invention are thus compounds of formula (I')

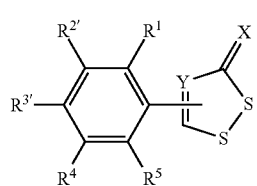

(I')

or a pharmaceutically acceptable tautomer, salt or solvate thereof wherein:
  X represents S, O or NHOH; preferably X is S or O; more preferably, X is S;
  Y represents CH, C or N; preferably Y is CH or N; more preferably Y is CH;
  R¹, R⁴ and R⁵ each independently represent hydrogen, hydroxy, halo, amino, alkylsulfonyl, aminosulfonyl, cyano, nitro, carboxy, aryl, alkoxy, haloalkyl, alkylamino, aminoalkyl, nitrooxyalkyl or carboxyalkyl;
  R²' and R³' together with the carbon atoms to which they are attached form a 5-membered heteroaryl moiety wherein —R³'—R²'— represents -A-CR⁶=B— or —B=CR⁶-A—; wherein:
    A represents O, S or NR⁷; wherein R⁷ represents hydrogen, C1-C8 alkyl or alkyloxycarbonyl;
    B represents CH or N; and
    R⁶ represents hydrogen, hydroxy, halo, amino, alkylsulfonyl, aminosulfonyl, cyano, nitro, carboxy, aryl, alkoxy, haloalkyl, alkylamino, aminoalkyl, nitrooxyalkyl or carboxyalkyl.

According to a preferred embodiment, the inhibitors of the invention are compounds formula (II)

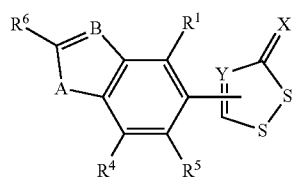

(II)

or a pharmaceutically acceptable tautomer, salt or solvate thereof, wherein X, Y, R¹, R⁴, R⁵, R⁶, A and B are as defined in formula (I).

According to one embodiment, in formula (II):
  X represents S, O or NHOH; preferably X is S;
  Y represents CH, C or N; preferably Y is CH;
  A represents O, S or NR⁷; wherein R⁷ represents hydrogen or C1-C8 alkyl group;
  B represent CH or N;
  R¹, R⁴ and R⁵ each independently represent hydrogen, hydroxy, halo, amino, alkylsulfonyl, aminosulfonyl, cyano, nitro, carboxy, aryl, alkoxy, haloalkyl, alkylamino, aminoalkyl, nitrooxyalkyl or carboxyalkyl;
  R⁶ represents hydrogen, hydroxy, halo, amino, alkylsulfonyl, aminosulfonyl, cyano, nitro, carboxy, aryl, alkoxy, haloalkyl, alkylamino, aminoalkyl, nitrooxyalkyl or carboxyalkyl.

According to a preferred embodiment, compounds of formula (II) are of formulae (IIa) or (IIb)

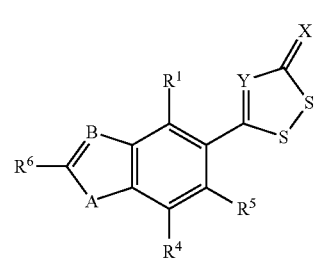

(IIa)

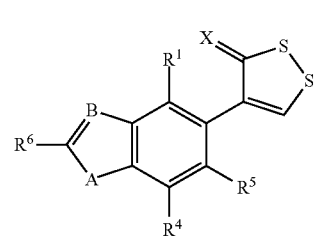

(IIb)

or a pharmaceutically acceptable tautomer, salt or solvate thereof, wherein X, Y, A, B, R¹, R⁴, R⁵ and R⁶ are as defined above.

In a preferred embodiment, the inhibitors of the invention are of formula (IIa).

According to a preferred embodiment, compounds of formula (IIa) are of formulae (IIa-1) or (IIa-2)

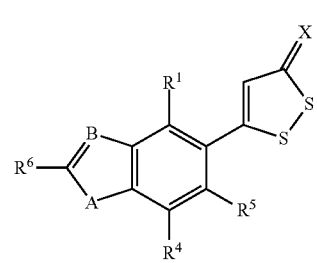

(IIa-1)

(IIa-2)

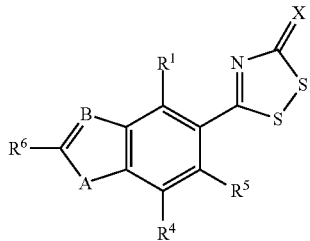

or a pharmaceutically acceptable tautomer, salt or solvate thereof, wherein X, A, B, $R^1$, $R^4$, $R^5$ and $R^6$ are as defined above.

In a preferred embodiment, the inhibitors of the invention are of formula (IIa-1). In another preferred embodiment, the inhibitors of the invention are of formula (IIa-2).

According to a preferred embodiment, compounds of formula (IIa-1) are of formulae (IIa-1'), (IIa-1") or (IIa-1''')

(IIa-1')

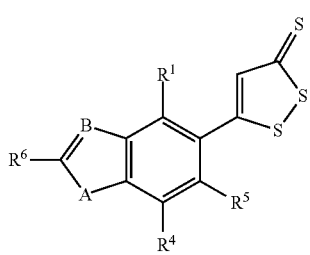

(IIa-1")

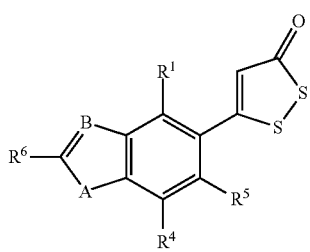

(IIa-1''')

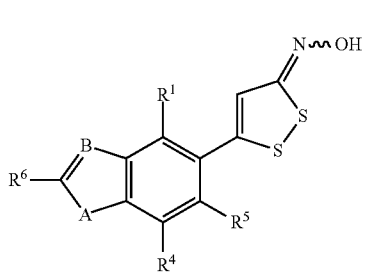

or a pharmaceutically acceptable tautomer, salt or solvate thereof, wherein A, B, $R^1$, $R^4$, $R^5$ and $R^6$ are as defined above.

In a preferred embodiment, the inhibitors of the invention are of formula (IIa-1') or (IIa-1"), more preferably of formula (IIa-1').

According to a preferred embodiment, compounds of formula (IIa-2) are of formulae (IIa-2'), (IIa-2") or (IIa-2''')

(IIa-2')

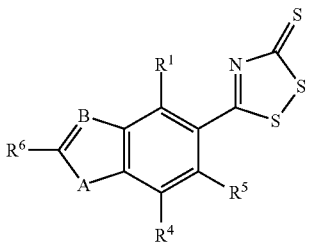

(IIa-2")

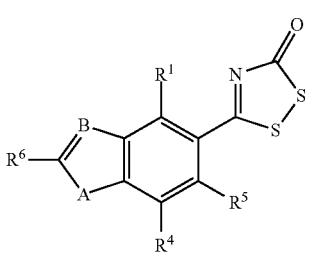

(IIa-2''')

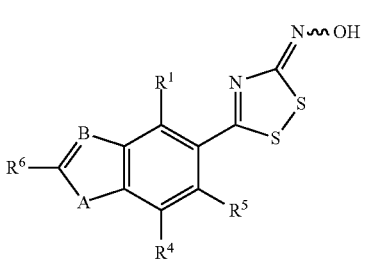

or a pharmaceutically acceptable tautomer, salt or solvate thereof, wherein A, B, $R^1$, $R^4$, $R^5$ and $R^6$ are as defined above.

In a preferred embodiment, the inhibitors of the invention are of formula (IIa-2') or (IIa-2").

According to a preferred embodiment, compounds of formula (IIa-1) and (IIa-2) are of formulae (IIa-1a), (IIa-1b), (IIa-1c), (IIa-1d), (IIa-1e), (IIa-2a), (IIa-2b), (IIa-2c), (IIa-2d) or (IIa-2e)

(IIa-1a)

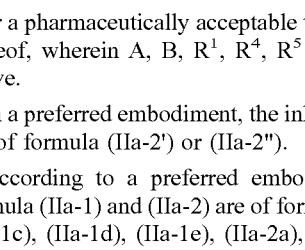

(IIa-11b)

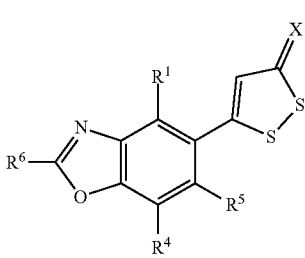

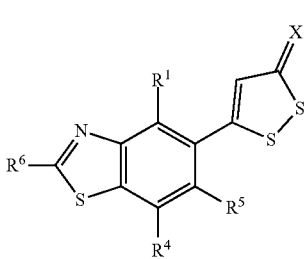

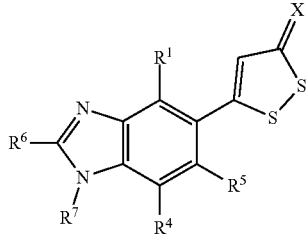
(IIa-1c)

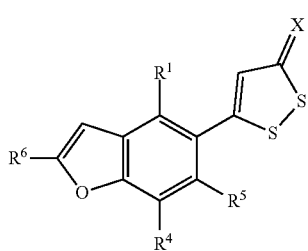
(IIa-1d)

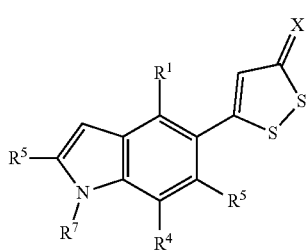
(IIa-1e)

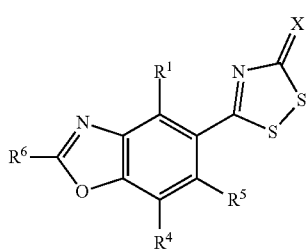
(IIa-2a)

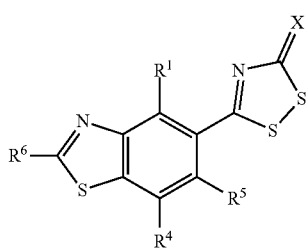
(IIa-2b)

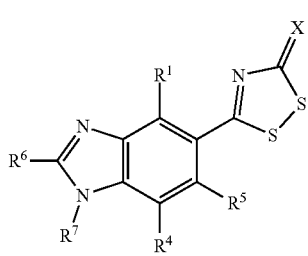
(IIa-2c)

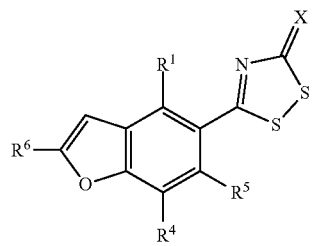
(IIa-2d)

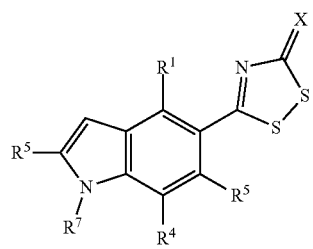
(IIa-2e)

or a pharmaceutically acceptable tautomer, salt or solvate thereof, wherein X, $R^1$, $R^4$, $R^5$, $R^6$ and $R^7$ are as defined above.

In a preferred embodiment, the inhibitors of the invention are of formula (IIa-1a), (IIa-1b), (IIa-1e), (IIa-2a), (IIa-2b) or (IIa-2e), more preferably of formula (IIa-1a) or (IIa-1e); more preferably of formula (IIa-1a).

According to a preferred embodiment, compounds of formula (IIb) are of formulae (IIb'), (IIb'') and (IIb''')

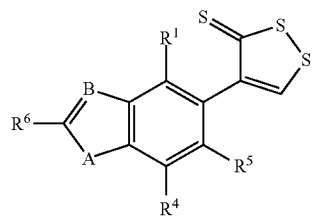
(IIb')

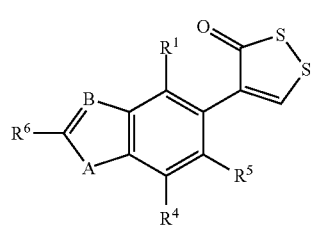
(IIb'')

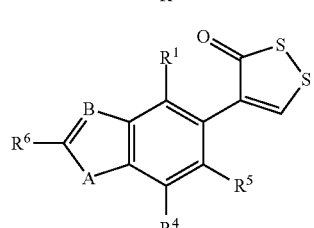
(IIb''')

or a pharmaceutically acceptable tautomer, salt or solvate thereof, wherein A, B, $R^1$, $R^4$, $R^5$ and $R^6$ are as defined above.

According to a preferred embodiment, compounds of formula (IIb) are of formulae (IIb-1), (IIb-2), (IIb-3), (IIb-4) or (IIb-5)

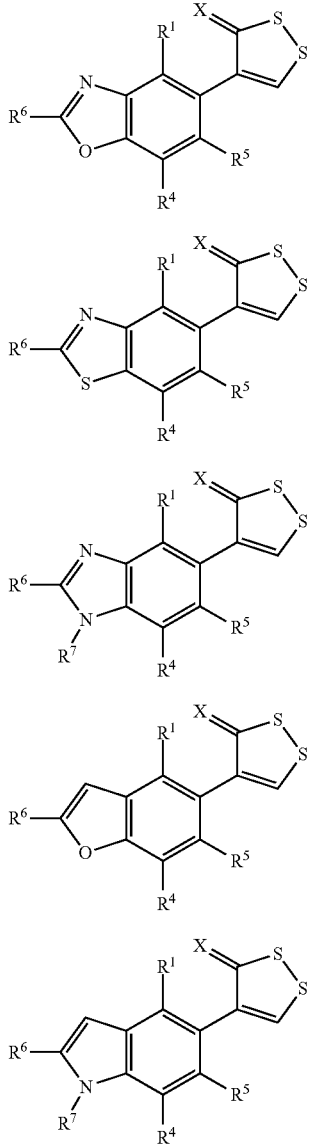

or a pharmaceutically acceptable tautomer, salt or solvate thereof, wherein X, $R^1$, $R^4$, $R^5$, $R^6$ and $R^7$ are as defined above.

According to a preferred embodiment, the inhibitors of the invention are compounds formula (III)

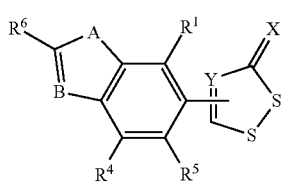

or a pharmaceutically acceptable tautomer, salt or solvate thereof, wherein X, Y, $R^1$, $R^4$, $R^5$, $R^6$, A and B are as defined in formula (I).

According to a preferred embodiment, compounds of formula (III) are of formulae (IIIa) or (IIb)

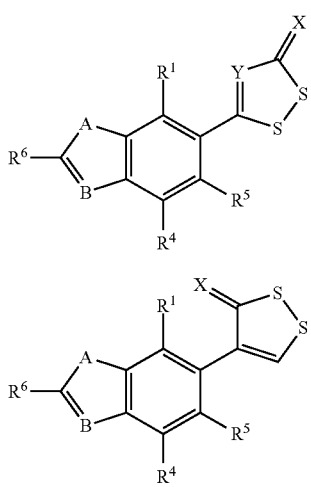

or a pharmaceutically acceptable tautomer, salt or solvate thereof, wherein X, Y, A, B, $R^1$, $R^4$, $R^5$ and $R^6$ are as defined above.

In a preferred embodiment, the inhibitors of the invention are of formula (IIIa).

According to a preferred embodiment, compounds of formula (IIIa) are of formulae (IIIa-1) or (IIIa-2)

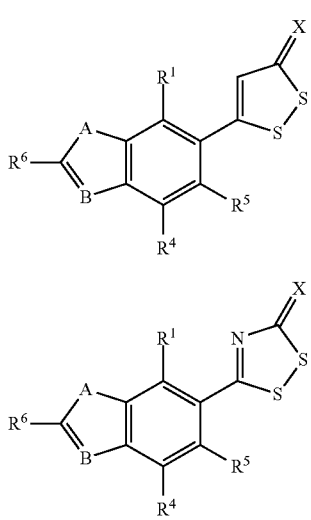

or a pharmaceutically acceptable tautomer, salt or solvate thereof, wherein X, A, B, $R^1$, $R^4$, $R^5$ and $R^6$ are as defined above.

In a preferred embodiment, the inhibitors of the invention are of formula (IIIa-1). In another preferred embodiment, the inhibitors of the invention are of formula (IIIa-2).

According to a preferred embodiment, compounds of formula (IIIa-1) are of formulae (IIIa-1'), (IIIa-1") or (IIIa-1''')

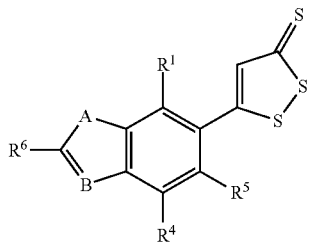
(IIa-1')

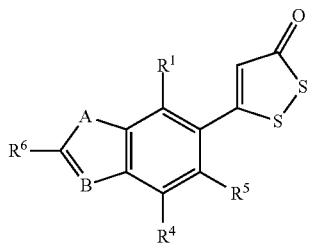
(IIa-1'')

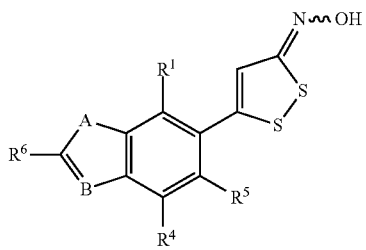
(IIa-1''')

or a pharmaceutically acceptable tautomer, salt or solvate thereof, wherein A, B, $R^1$, $R^4$, $R^5$ and $R^6$ are as defined above.

In a preferred embodiment, the inhibitors of the invention are of formula (IIIa-1') or (IIIa-1''), more preferably of formula (IIIa-1').

According to a preferred embodiment, compounds of formula (IIIa-2) are of formulae (IIIa-2'), (IIIa-2'') or (IIIa-2''')

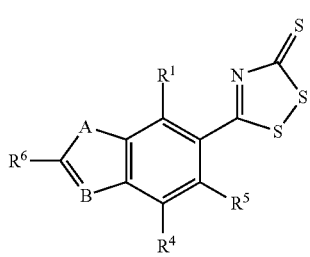
(IIa-2')

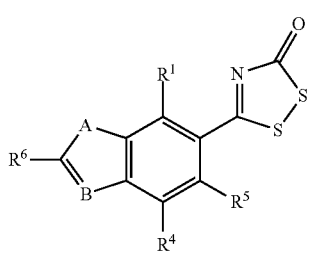
(IIa-2'')

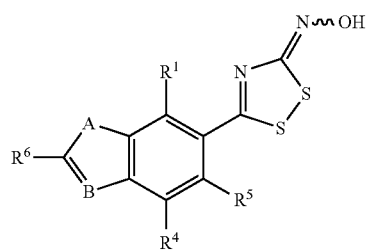
(IIa-2''')

or a pharmaceutically acceptable tautomer, salt or solvate thereof, wherein A, B, $R^1$, $R^4$, $R^5$ and $R^6$ are as defined above.

In a preferred embodiment, the inhibitors of the invention are of formula (IIIa-2') or (IIIa-2'').

According to a preferred embodiment, compounds of formula (IIIa-1) and (IIIa-2) are of formulae (IIIa-1a), (IIIa-1b), (IIIa-1c), (IIIa-1d), (IIIa-1e), (IIIa-2a), (IIIa-2b), (IIIa-2c), (IIIa-2d) or (IIIa-2e)

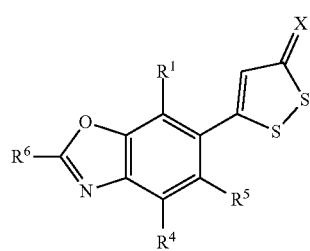
(IIIa-1a)

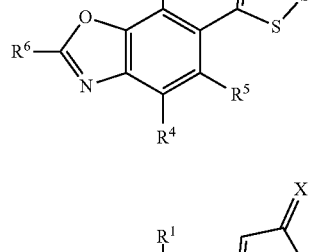
(IIIa-1b)

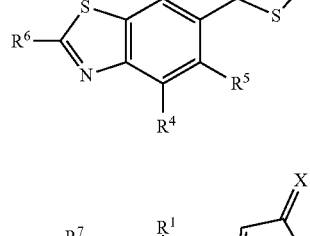
(IIIa-1c)

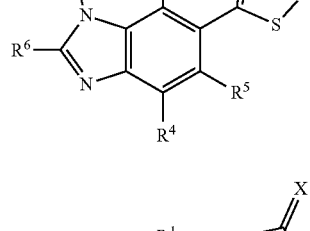
(IIIa-1d)

-continued (IIIa-1e)
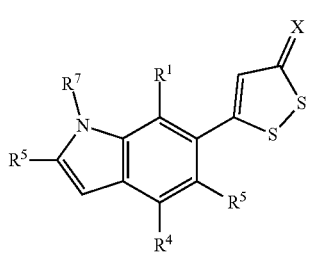

(IIIa-2a)
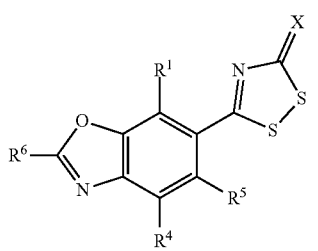

(IIIa-2b)
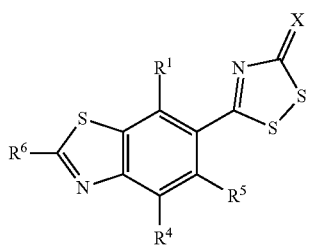

(IIIa-2c)
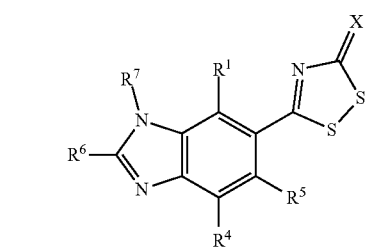

(IIIa-2d)
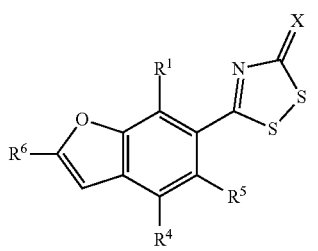

(IIIa-2e)
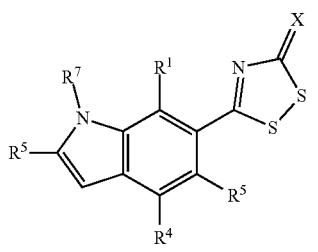

or a pharmaceutically acceptable tautomer, salt or solvate thereof, wherein X, $R^1$, $R^4$, $R^5$, $R^6$ and $R^7$ are as defined above.

In a preferred embodiment, the inhibitors of the invention are of formula (IIIa-1a), (IIIa-1b), (IIIa-1e), (IIIa-2a), (IIIa-2b) or (IIIa-2e), more preferably of formula (IIIa-1b).

According to a preferred embodiment, compounds of formula (IIIb) are of formulae (IIIb'), (IIIb") and (IIIb'")

(IIIb')
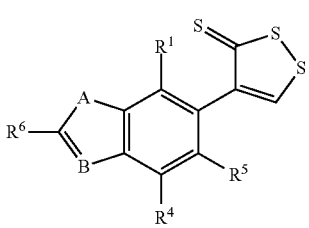

(IIIb")
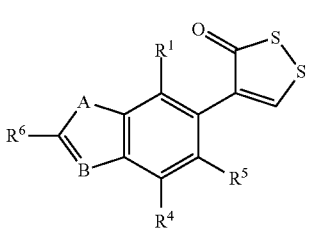

(IIIb'")
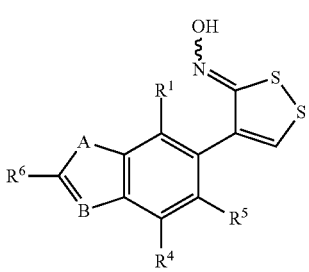

or a pharmaceutically acceptable tautomer, salt or solvate thereof, wherein A, B, $R^1$, $R^4$, $R^5$ and $R^6$ are as defined above.

According to a preferred embodiment, compounds of formula (IIIb) are of formulae (IIIb-1), (IIIb-2), (IIIb-3), (IIIb-4) or (IIIb-5)

(IIIb-1)
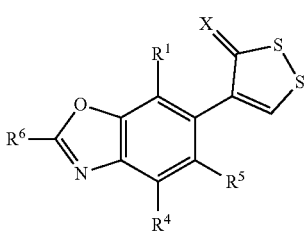

(IIIb-2)
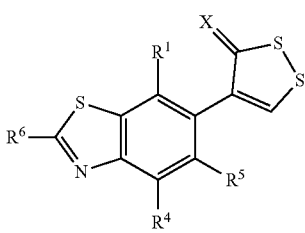

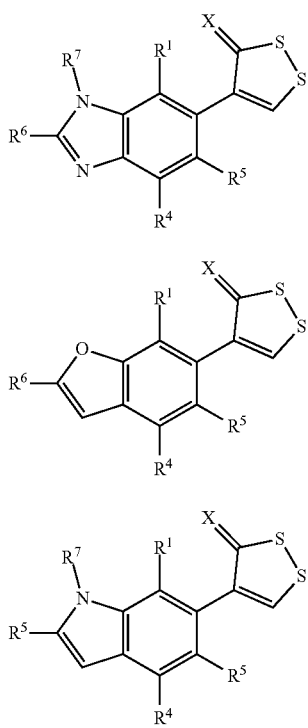

(IIIb-3)

(IIIb-4)

(IIIb-5)

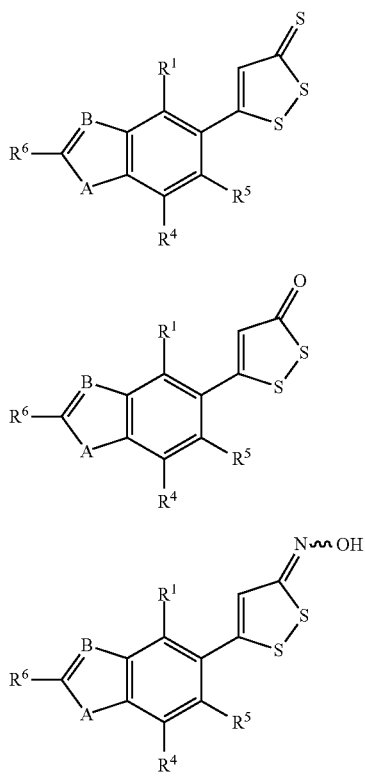

(IIa-1')

(IIa-1")

(IIa-1''')

or a pharmaceutically acceptable tautomer, salt or solvate thereof, wherein X, $R^1$, $R^4$, $R^5$, $R^6$ and $R^7$ are as defined above.

According to a specific embodiment, the inhibitors of the invention are selected from:

5-(4-hydroxyphenyl)-3H-1,2-dithiole-3-thione (AOX);

5-(4-hydroxyphenyl)-3H-1,2-dithiol-3-one (Cp1);

5-(4-hydroxyphenyl)-3H-1,2-dithiol-3-one oxime (Cp2);

5-(4-hydroxyphenyl)-3H-1,2,4-dithiazole-3-thione (Cp3);

4-(4-hydroxyphenyl)-3H-1,2-dithiole-3-thione (Cp4);

5-(2-hydroxybenzo[d]oxazol-5-yl)-3H-1,2-dithiole-3-thione (Cp5);

5-(2-hydroxybenzo[d]thiazol-6-yl)-3H-1,2-dithiole-3-thione (Cp6a);

5-(benzofuran-5-yl)-3H-1,2-dithiole-3-thione (Cp8); and methyl 5-(3-thioxo-3H-1,2-dithiol-5-yl)-1H-indole-1-carboxylate (Cp9a).

According to a preferred embodiment, the inhibitors of the invention are selected from AOX, Cp1, Cp3, Cp4, Cp5, Cp6a and Cp9a. According to a preferred embodiment, the inhibitors of the invention are selected from AOX, Cp1, Cp3, Cp5 and Cp6a. According to a preferred embodiment, the inhibitor of the invention is AOX. According to a preferred embodiment, the inhibitor of the invention is Cp1. According to a preferred embodiment, the inhibitor of the invention is Cp3. According to a preferred embodiment, the inhibitor of the invention is Cp5. According to a preferred embodiment, the inhibitor of the invention is Cp6a.

The invention also relates to a process for manufacturing compounds of formula (IIa-1), more specifically of formulae (IIa-1'), (IIa-1") and (IIa-1''') as defined above:

or a pharmaceutically acceptable tautomer, salt or solvate thereof, wherein A, B, $R^1$, $R^4$, $R^5$ and $R^6$ are as defined above;

said process comprising:

a) cyclizing a compound of formula (C)

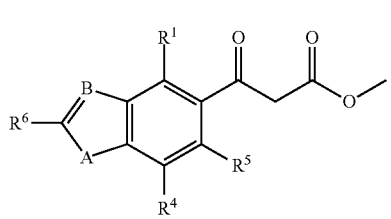

(C)

wherein A, B, $R^1$, $R^4$, $R^5$ and $R^6$ are as defined above; with a sulfur-based reagent; preferably, the sulfur-based reagent is $P_4S_{10}$; in the presence of a siloxane; preferably, the siloxane is the hexamethyldisiloxane ($Me_3SiOSiMe_3$, HMDO);

to obtain a compound of formula (IIa-1') as defined above; and optionally:

b1) compound of formula (IIa-1') can react with an oxidant; preferably the oxidant is the mercury acetate $Hg(OAc)_2$; to obtain a compound of formula (IIa-1") as defined above; or b2) compound of formula (IIa-1') can react with hydroxylamine $NH_2OH$—HCl; in the presence of a base; preferably, the base is sodium acetate (AcONa); to obtain a compound of formula (IIa-1''') as defined above.

According to one embodiment, the process for manufacturing compounds of formula (IIa-1) may comprise a preliminary step of manufacturing intermediate (C) comprising reacting an acid derivative of formula (A)

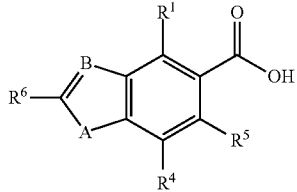

(A)

wherein A, B, $R^1$, $R^4$, $R^5$ and $R^6$ are as defined above;
with a 3-methoxy-3-oxopropanoic acid (B)

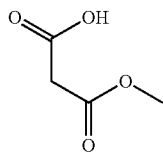

(B)

in the presence of magnesium chloride ($MgCl_2$), then diimidazolyl ketone, and then HCl; to obtain compound of formula (C).

According to one embodiment, the process for manufacturing compounds of formula (IIa-1) may comprise a preliminary step of manufacturing intermediate (C) comprising reacting an acid derivative of formula (A')

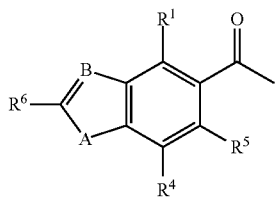

(A')

wherein A, B, $R^1$, $R^4$, $R^5$ and $R^6$ are as defined above;
with dimethylcarbonate in the presence of sodium hydride, to obtain compound of formula (C).

The invention also relates to a process for manufacturing a compound of formula (IIa-2), more specifically of formulae (IIa-2') and (IIa-2''')

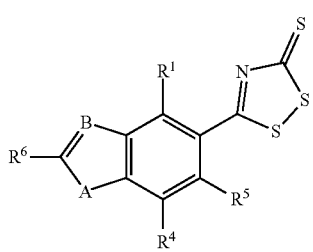

(IIa-2')

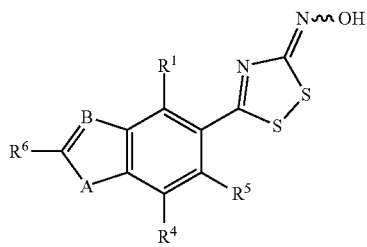

(IIa-2''')

or a pharmaceutically acceptable tautomer, salt or solvate thereof, wherein A, B, $R^1$, $R^4$, $R^5$ and $R^6$ are as defined above;
said process comprising cyclizing compound of formula (E)

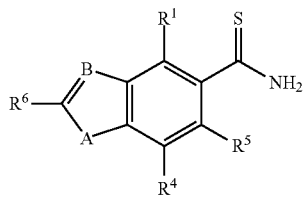

(E)

wherein A, B, $R^1$, $R^4$, $R^5$ and $R^6$ are as defined above;
with carbon disulfide ($CS_2$), in the presence of a base; preferably, the base is sodium hydride (NaH); to obtain a compound of formula (IIa-2') as defined above;
and optionally compound of formula (IIa-2') can react with hydroxylamine $NH_2OH$—HCl; in the presence of a base; preferably, the base is sodium acetate (AcONa); to obtain a compound of formula (IIa-2''') as defined above.

The invention also relates to a process for manufacturing a compound of formula (IIa-2'')

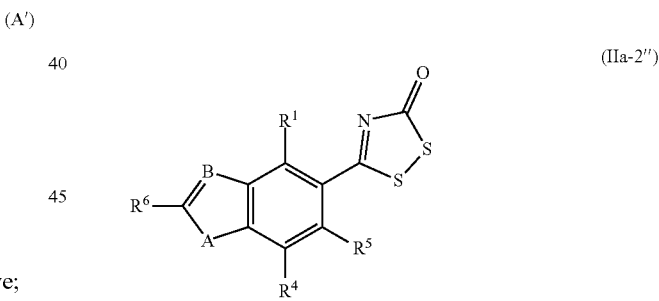

(IIa-2'')

or a pharmaceutically acceptable tautomer, salt or solvate thereof, wherein A, B, $R^1$, $R^4$, $R^5$ and $R^6$ are as defined above;
said process comprising reacting a compound of formula (E)

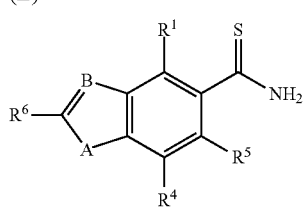

(E)

wherein A, B, $R^1$, $R^4$, $R^5$ and $R^6$ are as defined above;
with chlorocarbonylsulfenyl chloride, to obtain a compound of formula (IIa-2'').

According to one embodiment, intermediate (E) may be obtained by reacting amide derivative (D)

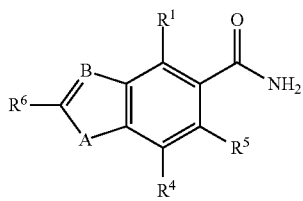

(D)

wherein A, B, $R^1$, $R^4$, $R^5$ and $R^6$ are as defined above;
with Lawesson's reagent, to obtain a compound of formula (E) as defined above.

According to one embodiment, amide intermediate (D) may be obtained by reacting acid derivative of formula (A)

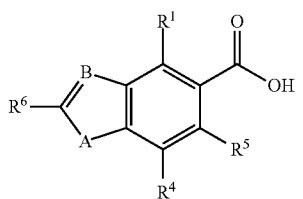

(A)

wherein A, B, $R^1$, $R^4$, $R^5$ and $R^6$ are as defined above;
with urea $CO(NH_2)_2$, in the presence of a base; preferably, the base is pyridine $(C_5H_5N)$; to obtain a compound of formula (D).

The invention also relates to a process for manufacturing compounds of formula (IIb), more specifically of formulae (IIb'), (IIb") and (IIb"')

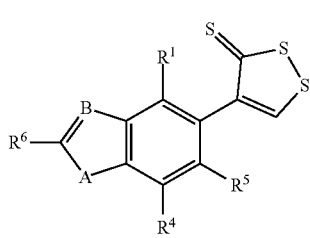

(IIb')

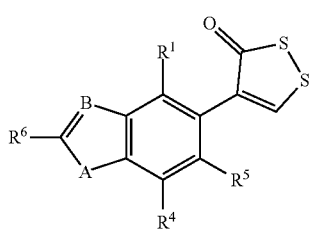

(IIb")

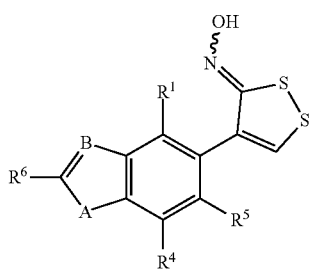

(IIb"')

or a pharmaceutically acceptable tautomer, salt or solvate thereof, wherein A, B, $R^1$, $R^4$, $R^5$ and $R^6$ are as defined above;

said process comprising:

a) cyclizing a compound of formula (G)

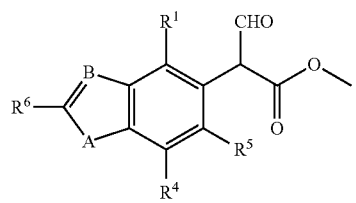

(G)

wherein A, B, $R^1$, $R^4$, $R^5$ and $R^6$ are as defined above;
with a sulfur-based reagent; preferably, the sulfur-based reagent is the octasulfur $S_8$; in the presence of the Lawesson reagent; to obtain a compound of formula (IIb') as defined above;

and optionally:

b1) compound of formula (IIb') can react with an oxidant; preferably the oxidant is the mercury acetate $Hg(OAc)_2$; to obtain a compound of formula (IIb") as defined above; or b2) compound of formula (IIb') can react with hydroxylamine $NH_2OH$—HCl; in the presence of a base; preferably, the base is sodium acetate (AcONa); to obtain a compound of formula (IIb"') as defined above.

According to one embodiment, the process for manufacturing compounds of formula (IIb) may comprise a preliminary step of manufacturing intermediate (G) comprising reacting an ester derivative of formula (F)

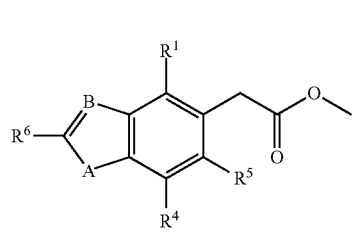

(F)

wherein A, B, $R^1$, $R^4$, $R^5$ and $R^6$ are as defined above;
with a Lewis acid; preferably, the Lewis acid is $TiCl_4$; in presence of base; preferably, the base is triethylamine ($Et_3N$); to obtain a compound of formula (G) as defined above.

The present invention also relates to a composition comprising or consisting of or consisting essentially of the inhibitor or selective inhibitor of the invention.

The present invention also relates to a composition for treating or for use in treating free oxygen radicals-related diseases in a subject in need thereof, comprising or consisting of or consisting essentially of the inhibitor as hereinabove described.

The present invention also relates to a composition for treating or for use in treating free oxygen radicals-related diseases, wherein said composition comprises or consists of or consists essentially of an inhibitor or selective inhibitor of mitochondrial production of ROS.

The present invention also relates to a pharmaceutical composition comprising or consisting of or consisting essentially of the inhibitor or selective inhibitor of the invention, in combination with at least one pharmaceutically acceptable excipient.

The present invention also relates to a pharmaceutical composition for treating or for use in treating free oxygen radicals-related diseases in a subject in need thereof, comprising or consisting of or consisting essentially of the inhibitor as hereinabove described in combination with at least one pharmaceutically acceptable excipient.

The present invention also relates to a pharmaceutical composition for treating or for use in treating free oxygen radicals-related diseases, wherein said pharmaceutical composition comprises or consists of or consists essentially of an inhibitor or selective inhibitor of mitochondrial production of ROS and at least one pharmaceutically acceptable excipient.

Suitable excipients include water, saline, Ringer's solution, dextrose solution, and solutions of ethanol, glucose, sucrose, dextran, mannose, mannitol, sorbitol, polyethylene glycol (PEG), phosphate, acetate, gelatin, collagen, Carbopol®, vegetable oils, and the like. One may additionally include suitable preservatives, stabilizers, antioxidants, antimicrobials, and buffering agents, such as, e.g., BHA, BHT, citric acid, ascorbic acid, tetracycline, and the like.

Other examples of pharmaceutically acceptable excipients that may be used in the composition of the invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene block polymers, polyethylene glycol and wool fat.

In addition some excipients may include, surfactants (e.g., hydroxypropylcellulose); suitable carriers, such as, e.g., solvents and dispersion media containing, e.g., water, ethanol, polyol (e.g., glycerol, propylene glycol, and liquid polyethylene glycol, and the like), suitable mixtures thereof, and vegetable oils, such as, e.g., peanut oil or sesame oil; isotonic agents, such as, e.g., sugars or sodium chloride; coating agents, such as, e.g., lecithin; agents delaying absorption, such as, e.g., aluminum monostearate and gelatin; preservatives, such as, e.g., benzalkonium chloride, benzethonium chloride, chlorobutanol, thimerosal and the like; buffers, such as, e.g., boric acid, sodium and potassium bicarbonate, sodium and potassium borates, sodium and potassium carbonate, sodium acetate, sodium biphosphate and the like; tonicity agents, such as, e.g., dextran 40, dextran 70, dextrose, glycerin, potassium chloride, propylene glycol, sodium chloride; antioxidants and stabilizers, such as, e.g., sodium bisulfite, sodium metabisulfite, sodium thiosulfite, thiourea and the like; nonionic wetting or clarifying agents, such as, e.g., polysorbate 80, polysorbate 20, poloxamer 282 and tyloxapol; viscosity modifying agents, such as, e.g., dextran 40, dextran 70, gelatin, glycerin, hydroxyethylcellulose, hydroxymethylpropylcellulose, lanolin, methylcellulose, petrolatum, polyethylene glycol, polyvinyl alcohol, polyvinylpyrrolidone, carboxymethylcellulose; and the like.

Other examples of pharmaceutically acceptable excipients are cyclodextrins (CDs) and derivatives thereof. Cyclodextrins may enable to improve solubilization and/or stabilization of the active principle. Preferably, the cyclodextrin is a beta-cyclodextrin. In an embodiment, the cyclodextrin is selected from SBE-cyclodextrin (SBE: sulfobutyl ether) and HP-cyclodextrin (HP: hydroxypropyl) or derivatives thereof. In an embodiment, the cyclodextrin is SBE-cyclodextrin, preferably SBE-beta-cyclodextrin. In an embodiment, the cyclodextrin is HP-cyclodextrin, preferably HP-beta-cyclodextrin.

The present invention also relates to a medicament comprising or consisting of or consisting essentially of the inhibitor or selective inhibitor of the invention.

The present invention also relates to a medicament for treating or for use in treating free oxygen radicals-related diseases in a subject in need thereof, comprising or consisting of or consisting essentially of the inhibitor as hereinabove described.

The present invention also relates to a medicament for treating or for use in treating free oxygen radicals-related diseases, wherein said medicament comprises or consists of or consists essentially of an inhibitor or selective inhibitor of mitochondrial production of ROS.

The present invention also relates to a cosmetic composition comprising the inhibitor of the invention.

The present invention also relates to a cosmeceutical composition comprising the inhibitor of the invention.

Another object of the invention is a conservation medium or preservation medium comprising or consisting of or consisting essentially of the inhibitor of the invention.

In one embodiment, the conservation medium is for the preservation of organs, biological tissues and/or living cells. In one embodiment, said organs include, but are not limited to, heart, liver, kidney, lung, pancreas, intestine, skin and cornea. In one embodiment, said organs are for transplantation, i.e., the transfer of any organ or body tissue from its site of origin to a recipient site. Specifically, in an allograft transplant procedure, the site of origin of the transplant is in a donor individual and the recipient site is in another, recipient individual.

In one embodiment, the conservation medium comprises the inhibitor of the invention at a concentration ranging 0.1 µM to 120 µM, i.e., at a concentration of about 0.1 µM, 0.5 µM, 1 µM, 2 µM, 3 µM, 4 µM, 5 µM, 10 µM, 15 µM, 20 µM, 30 µM, 40 µM, 50 µM, 75 µM, 100 µM or 120 µM.

In one embodiment, the composition, the pharmaceutical composition, the medicament, the cosmetic composition or the cosmeceutical composition of the invention is to be administered systemically or locally.

In one embodiment, the composition, the pharmaceutical composition, the medicament, the cosmetic composition or the cosmeceutical composition of the invention is to be administered orally, by injection, topically, nasally, buccally, rectally, vaginaly, intratracheally, by endoscopy, transmucosally, and by percutaneous administration.

In one embodiment, the composition, the pharmaceutical composition, the medicament, the cosmetic composition or the cosmeceutical composition of the invention is injected, preferably systemically injected. Examples of formulations adapted to systemic injections include, but are not limited to, liquid solutions or suspensions, solid forms suitable for solution in, or suspension in, liquid prior to injection. Examples of systemic injections include, but are not limited to, intravenous, subcutaneous, intramuscular, intradermal and intraperitoneal injection, and perfusion. In another embodiment, when injected, the composition, the pharmaceutical composition, the medicament, the cosmetic composition or the cosmeceutical composition of the invention is sterile. Methods for obtaining a sterile pharmaceutical composition include, but are not limited to, GMP synthesis (GMP stands for "Good manufacturing practice").

In another embodiment, the composition, the pharmaceutical composition, the medicament, the cosmetic composition or the cosmeceutical composition of the invention is orally administered. Examples of formulations adapted to oral administration include, but are not limited to, solid forms, liquid forms and gels. Examples of solid forms adapted to oral administration include, but are not limited to, pill, tablet, capsule, soft gelatine capsule, hard gelatine capsule, caplet, compressed tablet, cachet, wafer, sugar-coated pill, sugar coated tablet, or dispersing/or disintegrating tablet, powder, solid forms suitable for solution in, or suspension in, liquid prior to oral administration and effervescent tablet. Examples of liquid form adapted to oral administration include, but are not limited to, solutions, suspensions, drinkable solutions, elixirs, sealed phial, potion, drench, syrup and liquor.

In another embodiment, the composition, the pharmaceutical composition, the medicament, the cosmetic composition or the cosmeceutical composition of the invention is topically administered. Examples of formulations adapted to topical administration include, but are not limited to, sticks, lipsticks, waxes, creams, lotions, ointments, balms, gels, glosses, sunscreen preparations, cosmetics, masks, leave-on washes or cleansers, depilatory preparations and/or the like.

Topical administration characterizes the delivery, administration or application of the composition, the pharmaceutical composition, the medicament, the cosmetic composition or the cosmeceutical composition of the invention directly to the site of interest for a localized effect (generally onto one or more exposed or outer surfaces thereof, such as the outermost layer of the epidermis, which is exposed and visually observable), e.g., using hands, fingers or a wide variety of applicators (roll-up, roll-on or other stick container, tube container, cotton ball, powder puff, Q-tip, pump, brush, mat, cloth and/or the like). The application may be made, e.g., by laying, placing, rubbing, sweeping, pouring, spreading and/or massaging into, or onto, the skin, or by any other convenient or suitable method. Preferably, topical administration is effected without any significant absorption of components of the composition into the subject's blood stream (to avoid a systemic effect).

The composition, the composition, the pharmaceutical composition, the medicament, the cosmetic composition or the cosmeceutical composition of the invention of the invention can be mixed to form white, smooth, homogeneous, opaque cream or lotion with, e.g., benzyl alcohol 1% or 2% (w/w) as a preservative, emulsifying wax, glycerin, isopropyl palmitate, lactic acid, purified water and sorbitol solution. In addition, the compositions can contain polyethylene glycol 400 (PEG 400). They can be mixed to form ointments with, e.g., benzyl alcohol 2% (w/w) as preservative, white petrolatum, emulsifying wax and tenox II (butylated hydroxyanisole, propyl gallate, citric acid, propylene glycol). Woven pads or rolls of bandaging material, e.g., gauze, can be impregnated with the compositions in solution, lotion, cream, ointment or other such form can also be used for topical application.

In another embodiment, the composition, the pharmaceutical composition, the medicament, the cosmetic composition or the cosmeceutical composition of the invention can also be applied topically using a transdermal system, such as one of an acrylic-based polymer adhesive with a resinous crosslinking agent impregnated with the composition and laminated to an impermeable backing.

In one embodiment, the composition, the pharmaceutical composition, the medicament, the cosmetic composition or the cosmeceutical composition of the present invention can be administered as a transdermal patch, more particularly as a sustained-release transdermal patch. The transdermal patches can include any conventional form such as, e.g., adhesive matrix, polymeric matrix, reservoir patch, matrix or monolithic-type laminated structure, and are generally comprised of one or more backing layers, adhesives, penetration enhancers, an optional rate controlling membrane and a release liner which is removed to expose the adhesives prior to application. Polymeric matrix patches also comprise a polymeric-matrix forming material. Suitable transdermal patches are described in more detail in, e.g., U.S. Pat. Nos. 5,262,165, 5,948,433, 6,010,715 and 6,071,531, the disclosure of each of which are incorporated herein in their entirety.

Examples of formulations adapted to transdermal administration include, but are not limited to, ointment, paste, cream, film, balm, patch, such as, e.g., transdermal patch, gel, liposomal forms and the like.

In one embodiment, the transdermal composition is an ointment, paste, cream; film, balm, patch, such as, e.g., transdermal patch, gel, liposomal forms or the like.

In one embodiment of the invention, the ointment is an oleaginous ointment; an emulsified ointment such as, e.g., oil-in-water or a water-in-oil ointment; or a water-soluble ointment, preferably is an oleaginous ointment.

In one embodiment of the invention, the oleaginous ointment uses bases such as, e.g., plant and animal oils; plant and animal fats; waxes; vaseline, such as, e.g., white vaseline or vaseline oil; and paraffin such as, e.g., liquid paraffin or paraffin oil.

In one embodiment of the invention, the transdermal composition further comprises one or more excipients. Suitable pharmaceutically acceptable excipients are well-known from the skilled person. Examples of suitable excipients include, but are not limited to, carriers, emulsifying agents, stiffening agents, rheology modifiers or thickeners, surfactants, emollients, preservatives, humectants, buffering agents, solvents, moisturizing agents and stabilizers.

In another embodiment, a particular administration route may be intraocularly. In another embodiment, the administration route may be a topical ocular administration, such as, e.g., the administration of eye drops or by bathing the eye in an ophthalmic solution comprising the inhibitor of the invention.

The ophthalmic solution refers to sterile liquid, semi-solid or solid preparations intended for administration upon the eyeball and/or to the conjunctiva, or for insertion in the conjunctival sac or for administration into the posterior segment of the eye. As used herein, the term "posterior segment of the eye" refers to the back two third of the eye, comprising the anterior hyaloids membrane and the structures behind it (vitreous humor, retina, choroid, optic nerve). In particular, an ophthalmic composition may be administered into the vitreous, e.g., by intravitreous injection. Examples of ophthalmic compositions include, but are not limited to, eye drops, eye lotions, powders for eye drops and powders for eye lotions, and compositions to be injected into the conjunctival sac or into the vitreous.

Examples of carriers include, but are not limited to, water; buffered saline; petroleum jelly (Vaseline, also known as white soft paraffin); petrolatum; oils, such as, e.g., mineral oil, vegetable oil, animal oil, paraffin oil, castor oil or vaseline oil; organic and inorganic waxes, such as, e.g., microcrystalline, paraffin, bees wax and ozocerite wax;

natural polymers, such as, e.g., xanthanes, gelatin, cellulose, collagen, starch, or gum arabic; synthetic polymers; alcohols; polyols; and the like. In one embodiment of the invention, the carrier is a base cream, comprising an emulsifying agent, an oil-phase ingredient and a water phase ingredient.

Examples of well-known ointment or lotion base excipients include, but are not limited to, Vaseline, Plastibase™ (which is a base prepared with polyethylene (average molecular weight of about 21000 Da) and liquid paraffin) and ESMA-P™ (made of microcrystalline wax).

Examples of emulsifying agents include, but are not limited to, cetyl alcohol, cetostearyl alcohol, stearyl alcohol, carboxypolymethylene, polycarbophil, polyethylene glycol and derivatives thereof, polyoxyethylene and derivatives thereof, such as, e.g., polysorbate 20 or polysorbate 80, alone or in combination with fatty alcohols such as, e.g., cetyl alcohol, stearyl alcohol and cetostearyl alcohol, and sorbitan esters, such as, e.g., sorbitan fatty acid ester.

Examples of oil-phase ingredient include, but are not limited to, Vaseline, such as, e.g., white Vaseline, yellow Vaseline or Vaseline oil, paraffin such as, e.g., liquid paraffin or paraffin oil, dimethicone and mixtures thereof.

Examples of water-phase ingredients include, but are not limited to, water, glycerol and propyleneglycol.

Examples of stiffening agents include, but are not limited to, stearyl alcohol, cetostearyl alcohol, and cetyl alcohol.

Examples of rheology modifiers or thickeners include, but are not limited to, carbomers such as, e.g., Carbopol®, and polyoxyethylene tallow amines such as, e.g., Ethomeen®.

Examples of surfactants include, but are not limited to, anionic, cationic, amphoteric, and nonionic surfactants, such as, e.g., sodium lauryl sulfate, cetostearyl alcohol, cetyl alcohol, magnesium lauryl sulfate, a wax, or a combination thereof.

Examples of emollients include, but are not limited to, white or yellow petrolatum (white or yellow vaseline), liquid petrolatum (liquid vaseline), paraffin, or aquaphor.

Examples of preservatives include, but are not limited to, antimicrobial preservatives such as, e.g., nipagin (methyl hydroxybenzoate), nipasol (hydroxybenzoate), butylparaben, ethylparaben, methylparaben, propyl paraben potassium, propyl paraben sodium, parahydroxybenzoate esters, sorbic acid, potassium sorbate, benzoic acid, parabens, chlorobutanol, phenol, thimerosal, sodium benzoate and benzyl alcohol.

Examples of humectants include, but are not limited to, propylene glycol and propylene glycol alginate.

Examples of buffering agents include, but are not limited to, sodium hydroxide, citric acid and potassium hydroxide.

Examples of solvents include, but are not limited to, water, isopropanol, benzyl alcohol, and propylene glycol.

Examples of moisturizing agents include, but are not limited to, glycerin, mineral oil, polyoxyethylene hardened castor oil and Vaseline, propylene glycol, paraffins, waxes, such as, e.g., bees wax, polyethylene glycols or mixtures thereof, such as, e.g., macrogol (macrogol is a mixture of polyethylene glycols of different molecular weights), stearyl alcohol, benzyl alcohol, parahydrobenzoate esters (parabens), gelled hydrocarbon, citric acid, squalene, lanolins, glycerin, polyoxyethylene hardened castor oil, sorbitan fatty ester, glycerin fatty ester, animal and vegetable fats, oils, starch, tragacanth, cellulose derivatives, silicones, bentonites, silicic acid, talc, zinc oxide and mixtures thereof.

Examples of stabilizers include, but are not limited to, carbohydrates such as, e.g., sucrose, lactose and trehalose, sugar alcohols such as, e.g., mannitol and sorbitol, amino acids such as, e.g., histidine, glycine, phenylalanine and arginine.

In one embodiment of the invention, the composition, the pharmaceutical composition, the medicament, the cosmetic composition or the cosmeceutical composition of the invention may be used in conjunction with delivery systems that facilitate delivery of the agents to the central nervous system. For example, various blood brain barrier (BBB) permeability enhancers may be used to transiently and reversibly increase the permeability of the blood brain barrier to a treatment agent. Such BBB permeability enhancers include but are not limited to leukotrienes, bradykinin agonists, histamine, tight junction disruptors (e.g., zonulin, zot), hyperosmotic solutions (e.g., mannitol), cytoskeletal contracting agents, and short chain alkylglycerols (e.g., 1-O-pentylglycerol). Oral, sublingual, parenteral, implantation, nasal and inhalational routes can provide delivery of the active agent to the central nervous system. In some embodiments, the compounds of the present invention may be administered to the central nervous system with minimal effects on the peripheral nervous system.

The blood-brain barrier (BBB) is a physical barrier and system of cellular transport mechanisms between the blood vessels in the central nervous system (CNS) and most areas of the CNS itself. The BBB maintains homeostasis by restricting the entry of potentially harmful chemicals from the blood, and by allowing the entry of essential nutrients. However, the BBB can pose a formidable barrier to delivery of pharmacological agents to the CNS for treatment of disorders or maintaining or enhancing normal and desirable brain functions, such as cognition, learning, and memory.

In one embodiment, the inhibitor, the composition, the pharmaceutical composition, the medicament, the cosmetic composition or the cosmeceutical composition is administered in a sustained-release form. In another embodiment, the composition, the pharmaceutical composition or the medicament comprises a delivery system that controls the release of the modulator.

In one embodiment, the inhibitor, the composition, the pharmaceutical composition, the medicament, the cosmetic composition or the cosmeceutical composition of the invention is administered at a dose determined by the skilled artisan and personally adapted to each subject.

It will be understood that the total daily usage of the inhibitor, the composition, the pharmaceutical composition, the medicament, the cosmetic composition or the cosmeceutical composition of the present invention will be decided by the attending physician within the scope of sound medical judgment. The specific therapeutically effective amount for any particular patient will depend upon a variety of factors including the disease being treated and the severity of the disease; the specific composition employed, the age, body weight, general health, sex and diet of the subject; the time of administration, route of administration, the duration of the treatment; drugs used in combination or coincidental with the inhibitor, the composition, the pharmaceutical composition, the medicament, the cosmetic composition or the cosmeceutical composition of the invention; and like factors well-known in the medical arts. For example, it is well within the skill of the art to start doses of a therapeutic compound at levels lower than those required to achieve the desired therapeutic effect and to gradually increase the dosage until the desired effect is achieved; but, at the opposite, it can be equally useful to start with a loading dose, a manner to reach steady-state plasma concentration more quickly, and then to follow with a maintenance dose calculated to exactly compensate the effect of the elimination process.

In one embodiment, a therapeutically effective amount of the inhibitor, the composition, the pharmaceutical composition, the medicament, the cosmetic composition or the cosmeceutical composition of the invention is administered at least once a day, twice a day, at least three times a day.

In another embodiment, a therapeutically effective amount of the inhibitor, the composition, the pharmaceutical composition, the medicament, the cosmetic composition or the cosmeceutical composition of the invention is administered every two, three, four, five, six days.

In another embodiment, a therapeutically effective amount of the inhibitor, the composition, the pharmaceutical composition, the medicament, the cosmetic composition or the cosmeceutical composition of the invention is administered twice a week, every week, every two weeks, once a month.

In one embodiment of the invention, the daily amount of the inhibitor, the composition, the pharmaceutical composition, the medicament, the cosmetic composition or the cosmeceutical composition to be administered to a subject ranges from about 1 μg/day to about 100 mg/day, from about 1 μg/day to about 50 mg/day, from about 1 μg/day to about 10 mg/day, from about 1 μg/day to about 9 mg/day, from about 1 μg/day to about 8 mg/day, from about 1 μg/day to about 7 mg/day, from about 1 μg/day to about 6 mg/day, from about 1 μg/day to about 5 mg/day, from about 1 μg/day to about 4 mg/day, from about 1 μg/day to about 3 mg/day, from about 1 μg/day to about 2 mg/day, from about 1 μg/day to about 1 mg/day, from about 1 μg/day to about 100 μg/day.

In one embodiment of the invention, the daily amount of the inhibitor, the composition, the pharmaceutical composition, the medicament, the cosmetic composition or the cosmeceutical composition to be administered to a subject ranges from about 1 μg/day to about 10 mg/day, from about 5 μg/day to about 10 mg/day, from about 10 μg/day to about 7.5 mg/day, from about 10 μg/day to about 5 mg/day, from about 10 μg/day to about 2.5 mg/day, from about 10 μg/day to about 2 mg/day, from about 10 μg/day to about 1 mg/day, from about 10 μg/day to about 0.75 mg/day, from about 10 μg/day to about 0.5 mg/day, from about 10 μg/day to about 0.25 mg/day.

In one embodiment of the invention, the daily amount of the inhibitor, the composition, the pharmaceutical composition, the medicament, the cosmetic composition or the cosmeceutical composition to be administered to a subject ranges from about 0.1 mg/day to about 2000 mg/day, from about 0.1 mg/day to about 1500 mg/day, from about 0.1 mg/day to about 1000 mg/day, from about 0.1 mg/day to about 500 mg/day, from about 0.1 mg/day to about 200 mg/day, from about 0.5 mg/day to about 2000 mg/day, from about 0.5 mg/day to about 1500 mg/day, from about 0.5 mg/day to about 1000 mg/day, from about 0.5 mg/day to about 500 mg/day, from about 0.5 mg/day to about 200 mg/day, from about 1 mg/day to about 2000 mg/day, from about 1 mg/day to about 1500 mg/day, from about 1 mg/day to about 1000 mg/day, from about 1 mg/day to about 500 mg/day, from about 1 mg/day to about 200 mg/day.

In one embodiment of the invention, the daily amount of the inhibitor, the composition, the pharmaceutical composition, the medicament, the cosmetic composition or the cosmeceutical composition to be administered to a subject is about 1 μg/day, about 2 μg/day, about 4 μg/day, about 6 μg/day, about 8 μg/day, about 10 μg/day, about 15 μg/day, about 20 μg/day, about 25 μg/day, about 30 μg/day, about 35 μg/day, about 40 μg/day, about 45 μg/day, about 50 μg/day, about 55 μg/day, about 60 μg/day, about 65 μg/day, about 70 μg/day, about 75 μg/day, about 80 μg/day, about 85 μg/day, about 90 μg/day, about 95 μg/day, about 100 μg/day, about 150 μg/day, about 200 μg/day, about 250 μg/day, about 300 μg/day, about 350 μg/day, about 400 μg/day, about 450 μg/day, about 500 μg/day.

In one embodiment of the invention, the daily amount of the inhibitor, the composition, the pharmaceutical composition, the medicament, the cosmetic composition or the cosmeceutical composition to be administered to a subject is about 0.1 mg/day, 0.2 mg/day, 0.3 mg/day, 0.4 mg/day, 0.5 mg/day, 0.6 mg/day, 0.7 mg/day, 0.8 mg/day, 0.9 mg/day, 1 mg/day, 2 mg/day, 4 mg/day, 6 mg/day, 8 mg/day, 10 mg/day, 15 mg/day, 20 mg/day, 25 mg/day, 30 mg/day, 35 mg/day, 40 mg/day, 45 mg/day, 50 mg/day, 75 mg/day, 100 mg/day, 125 mg/day, 150 mg/day, 175 mg/day, 200 mg/day, 300 mg/day, 400 mg/day, 500 mg/day, 600 mg/day, 700 mg/day, 800 mg/day, 900 mg/day, 1000 mg/day, 1200 mg/day, 1400 mg/day, 1600 mg/day, 1800 mg/day, 2000 mg/day.

In one embodiment of the invention, the daily amount of the inhibitor, the composition, the pharmaceutical composition, the medicament, the cosmetic composition or the cosmeceutical composition to be administered to a subject ranges from about 0.1 μg/kg/day to about 10 mg/kg/day, from about 0.1 μg/kg/day to about 5 mg/kg/day, from about 0.1 μg/kg/day to about 1 mg/kg/day, from about 0.1 μg/kg/day to about 0.9 mg/kg/day, from about 0.1 μg/kg/day to about 0.8 mg/kg/day, from about 0.1 μg/kg/day to about 0.7 mg/kg/day, from about 0.1 μg/kg/day to about 0.6 mg/kg/day, from about 0.1 μg/kg/day to about 0.5 mg/kg/day, from about 0.1 μg/kg/day to about 0.4 mg/kg/day, from about 0.1 μg/kg/day to about 0.3 mg/kg/day, from about 0.1 μg/kg/day to about 0.2 mg/kg/day, from about 0.1 μg/kg/day to about 0.1 mg/kg/day, from about 0.1 μg/kg/day to about 10 μg/kg/day.

In one embodiment of the invention, the daily amount of the inhibitor, the composition, the pharmaceutical composition, the medicament, the cosmetic composition or the cosmeceutical composition to be administered to a subject ranges from about 0.1 μg/kg/day to about 1 mg/kg/day, from about 0.5 μg/kg/day to about 1 mg/kg/day, from about 1 μg/kg/day to about 0.75 mg/kg/day, from about 1 μg/kg/day to about 0.5 mg/kg/day, from about 1 μg/kg/day to about 0.25 mg/kg/day, from about 1 μg/kg/day to about 0.2 mg/kg/day, from about 1 μg/kg/day to about 0.1 mg/kg/day, from about 1 μg/kg/day to about 0.075 mg/kg/day, from about 1 μg/kg/day to about 0.05 mg/kg/day, from about 1 μg/kg/day to about 0.025 mg/kg/day.

In one embodiment of the invention, the daily amount of the inhibitor, the composition, the pharmaceutical composition, the medicament, the cosmetic composition or the cosmeceutical composition to be administered to a subject ranges from about 0.01 mg/kg/day to about 20 mg/kg/day, from about 0.01 mg/kg/day to about 15 mg/kg/day, from about 0.01 mg/kg/day to about 12 mg/kg/day, from about 0.01 mg/kg/day to about 10 mg/kg/day, from about 0.01 mg/kg/day to about 9 mg/kg/day, from about 0.01 mg/kg/day to about 8 mg/kg/day, from about 0.01 mg/kg/day to about 7 mg/kg/day, from about 0.01 mg/kg/day to about 6 mg/kg/day, from about 0.01 mg/kg/day to about 5 mg/kg/day, from about 0.01 mg/kg/day to about 4 mg/kg/day, from about 0.01 mg/kg/day to about 3 mg/kg/day, from about 0.01 mg/kg/day to about 2 mg/kg/day, from about 0.01 mg/kg/day to about 1 mg/kg/day.

In one embodiment of the invention, the daily amount of the inhibitor, the composition, the pharmaceutical composition, the medicament, the cosmetic composition or the cosmeceutical composition to be administered to a subject is about 0.1 µg/kg/day, about 0.2 µg/kg/day, about 0.4 µg/kg/day, about 0.6 µg/kg/day, about 0.8 µg/kg/day, about 1 µg/kg/day, about 1.5 µg/kg/day, about 2.0 µg/kg/day, about 2.5 µg/kg/day, about 3.0 µg/kg/day, about 3.5 µg/kg/day, about 4.0 µg/kg/day, about 4.5 µg/kg/day, about 5.0 µg/kg/day, about 5.5 µg/kg/day, about 6.0 µg/kg/day, about 6.5 µg/kg/day, about 7.0 µg/kg/day, about 7.5 µg/kg/day, about 8.0 µg/kg/day, about 8.5 µg/kg/day, about 9.0 µg/kg/day, about 9.5 µg/kg/day, about 10.0 µg/kg/day, about 15.0 µg/kg/day, about 20.0 µg/kg/day, about 25.0 µg/kg/day, about 30.0 µg/kg/day, about 35.0 µg/kg/day, about 40.0 µg/kg/day, about 45.0 µg/kg/day, about 50.0 µg/kg/day.

In one embodiment of the invention, the daily amount of the inhibitor, the composition, the pharmaceutical composition, the medicament, the cosmetic composition or the cosmeceutical composition to be administered to a subject is about 0.01 mg/kg/day, about 0.02 mg/kg/day, about 0.03 mg/kg/day, about 0.04 mg/kg/day, about 0.05 mg/kg/day, about 0.06 mg/kg/day, about 0.07 mg/kg/day, about 0.08 mg/kg/day, about 0.09 mg/kg/day, about 0.1 mg/kg/day, about 0.2 mg/kg/day, about 0.3 mg/kg/day, about 0.4 mg/kg/day, about 0.5 mg/kg/day, about 0.6 mg/kg/day, about 0.7 mg/kg/day, about 0.8 mg/kg/day, about 0.9 mg/kg/day, about 1 mg/kg/day, about 1.5 mg/kg/day, about 2 mg/kg/day, about 2.5 mg/kg/day, about 3 mg/kg/day, about 3.5 mg/kg/day, about 4 mg/kg/day, about 4.5 mg/kg/day, about 5 mg/kg/day, about 6 mg/kg/day, about 7 mg/kg/day, about 8 mg/kg/day, about 9 mg/kg/day, about 10 mg/kg/day, about 12 mg/kg/day, about 14 mg/kg/day, about 16 mg/kg/day, about 18 mg/kg/day, about 20 mg/kg/day.

In one embodiment of the invention, the inhibitor, the composition, the pharmaceutical composition, the medicament, the cosmetic composition or the cosmeceutical composition of the invention is to be administered at a quantity of about 1 µg to about 100 mg, from about 1 µg to about 50 mg, from about 1 µg to about 10 mg, from about 1 µg to about 9 mg, from about 1 µg to about 8 mg, from about 1 µg to about 7 mg, from about 1 µg to about 6 mg, from about 1 µg to about 5 mg, from about 1 µg to about 4 mg, from about 1 µg to about 3 mg, from about 1 µg to about 2 mg, from about 1 µg to about 1 mg, from about 1 µg to about 100 µg.

In one embodiment of the invention, the inhibitor, the composition, the pharmaceutical composition, the medicament, the cosmetic composition or the cosmeceutical composition of the invention is to be administered at a quantity of about 1 µg to about 10 mg, from about 5 µg to about 10 mg, from about 10 µg to about 7.5 mg, from about 10 µg to about 5 mg, from about 10 µg to about 2.5 mg, from about 10 µg to about 2 mg, from about 10 µg to about 1 mg, from about 10 µg to about 0.75 mg, from about 10 µg to about 0.5 mg, from about 10 µg to about 0.25 mg.

In another embodiment, the inhibitor, the composition, the pharmaceutical composition, the medicament, the cosmetic composition or the cosmeceutical composition of the invention is to be administered at a quantity of about 0.02 mg to about 2000 mg, from about 0.02 mg to about 1500 mg, from about 0.02 mg to about 1000 mg, from about 0.02 mg to about 500 mg, from about 0.02 mg to about 200 mg, from about 0.02 mg to about 100 mg, from about 0.02 mg to about 50 mg, from about 0.02 mg to about 25 mg, from about 0.02 mg to about 10 mg, from about 0.02 mg to about 5 mg.

In another embodiment, the inhibitor, the composition, the pharmaceutical composition, the medicament, the cosmetic composition or the cosmeceutical composition of the invention is to be administered at a quantity of about 0.02 mg, 0.04 mg, 0.06 mg, 0.08 mg, 0.1 mg, 0.2 mg, 0.3 mg, 0.4 mg, 0.5 mg, 0.6 mg, 0.7 mg, 0.8 mg, 0.9 mg, 1 mg, 1.5 mg, 2 mg, 2.5 mg, 3 mg, 3.5 mg, 4 mg, 4.5 mg, 5 mg, 5.5 mg, 6 mg, 6.5 mg, 7 mg, 7.5 mg, 8 mg, 8.5 mg, 9 mg, 9.5 mg, 10 mg, 15 mg, 20 mg, 25 mg, 30 mg, 35 mg, 40 mg, 45 mg, 50 mg, 75 mg, 100 mg, 125 mg, 150 mg, 175 mg, 200 mg, 300 mg, 400 mg, 500 mg, 600 mg, 700 mg, 800 mg, 900 mg, 1000 mg, 1200 mg, 1400 mg, 1600 mg, 1800 mg, 2000 mg.

In one embodiment, the method of the invention is for a chronic treatment. In another embodiment, the method of the invention is for an acute treatment.

In one embodiment of the invention, the subject is diagnosed with a free oxygen radicals-related disease. In another embodiment of the invention, the subject is at risk of developing a free oxygen radicals-related disease.

In one embodiment, said subject is an adult, a teenager, a child, a young child or a new born child.

Another object of the present invention is a method for inhibiting free oxygen radicals' production in a subject in need thereof by acting on mitochondria at site $I_Q$ of complex I, comprising the administration of an effective amount into the subject of an inhibitor or selective inhibitor of mitochondrial production of ROS.

Another object of the present invention is a method for inhibiting free oxygen radicals' production in a subject in need thereof without inhibiting cytosolic ROS production, comprising the administration of an effective amount into the subject of an inhibitor or selective inhibitor of mitochondrial production of ROS.

Another object of the present invention is a method for treating and/or preventing; or for the treatment and/or prevention of at least one free oxygen radicals-related disease in a subject in need thereof, comprising the administration of an effective amount into the subject of an inhibitor or selective inhibitor of mitochondrial production of ROS.

Another object of the present invention is a method for treating and/or preventing; or for the treatment and/or prevention of at least one free oxygen radicals-related disease in a subject in need thereof by acting on mitochondria at site $I_Q$ of complex I, comprising the administration of an effective amount into the subject of an inhibitor or selective inhibitor of mitochondrial production of ROS.

Another object of the present invention is a method for treating and/or preventing; or for the treatment and/or prevention of at least one free oxygen radicals-related disease in a subject in need thereof without inhibiting cytosolic ROS production, comprising the administration of an effective amount into the subject of an inhibitor or selective inhibitor of mitochondrial production of ROS.

Another object of the present invention is a method for treating and/or preventing; or for the treatment and/or prevention of free oxygen-radicals related cardiovascular diseases in a subject in need thereof, comprising the administration of an effective amount into the subject of an inhibitor or selective inhibitor of mitochondrial production of ROS.

Another object of the present invention is a method for treating and/or preventing; or for the treatment and/or prevention of free oxygen-radicals related cardiovascular diseases in a subject in need thereof by acting on mitochondria at site $I_Q$ of complex I, comprising the administration of an effective amount into the subject of an inhibitor or selective inhibitor of mitochondrial production of ROS.

Another object of the present invention is a method for treating and/or preventing; or for the treatment and/or prevention of free oxygen-radicals related cardiovascular diseases in a subject in need thereof without inhibiting cytosolic ROS production, comprising the administration of an effective amount into the subject of an inhibitor or selective inhibitor of mitochondrial production of ROS.

Another object of the present invention is a method for treating and/or preventing; or for the treatment and/or prevention of myocardial infarction in a subject in need thereof, comprising the administration of an effective amount into the subject of an inhibitor or selective inhibitor of mitochondrial production of ROS.

Another object of the present invention is a method for treating and/or preventing; or for the treatment and/or prevention of myocardial infarction in a subject in need thereof by acting on mitochondria at site $I_Q$ of complex I, comprising the administration of an effective amount into the subject of an inhibitor or selective inhibitor of mitochondrial production of ROS.

Another object of the present invention is a method for treating and/or preventing; or for the treatment and/or prevention of myocardial infarction in a subject in need thereof without inhibiting cytosolic ROS production, comprising the administration of an effective amount into the subject of an inhibitor or selective inhibitor of mitochondrial production of ROS.

Another object of the present invention is a method for treating and/or preventing; or for the treatment and/or prevention of heart failure in a subject in need thereof, comprising the administration of an effective amount into the subject of an inhibitor or selective inhibitor of mitochondrial production of ROS.

Another object of the present invention is a method for treating and/or preventing; or for the treatment and/or prevention of heart failure in a subject in need thereof by acting on mitochondria at site $I_Q$ of complex I, comprising the administration of an effective amount into the subject of an inhibitor or selective inhibitor of mitochondrial production of ROS.

Another object of the present invention is a method for treating and/or preventing; or for the treatment and/or prevention of heart failure in a subject in need thereof without inhibiting cytosolic ROS production, comprising the administration of an effective amount into the subject of an inhibitor or selective inhibitor of mitochondrial production of ROS.

Another object of the present invention is a method for treating and/or preventing; or for the treatment and/or prevention of cardiac toxicity, preferably cardiac toxicity of anthracyclines, cardiac toxicity of anti-cancer drugs, cardiac toxicity of quinolones and/or cardiac toxicity of antiviral drugs, more preferably cardiac toxicity of anthracyclines in a subject in need thereof, comprising the administration of an effective amount into the subject of an inhibitor or selective inhibitor of mitochondrial production of ROS.

Another object of the present invention is a method for treating and/or preventing; or for the treatment and/or prevention of cardiac toxicity, preferably cardiac toxicity of anthracyclines, cardiac toxicity of anti-cancer drugs, cardiac toxicity of quinolones and/or cardiac toxicity of antiviral drugs, more preferably cardiac toxicity of anthracyclines in a subject in need thereof by acting on mitochondria at site $I_Q$ of complex I, comprising the administration of an effective amount into the subject of an inhibitor or selective inhibitor of mitochondrial production of ROS.

Another object of the present invention is a method for treating and/or preventing; or for the treatment and/or prevention of cardiac toxicity, preferably cardiac toxicity of anthracyclines, cardiac toxicity of anti-cancer drugs, cardiac toxicity of quinolones and/or cardiac toxicity of antiviral drugs, more preferably cardiac toxicity of anthracyclines in a subject in need thereof without inhibiting cytosolic ROS production, comprising the administration of an effective amount into the subject of an inhibitor or selective inhibitor of mitochondrial production of ROS.

Another object of the present invention is a method for treating and/or preventing; or for the treatment and/or prevention of pulmonary hypertension in a subject in need thereof, comprising the administration of an effective amount into the subject of an inhibitor or selective inhibitor of mitochondrial production of ROS.

Another object of the present invention is a method for treating and/or preventing; or for the treatment and/or prevention of pulmonary hypertension in a subject in need thereof by acting on mitochondria at site $I_Q$ of complex I, comprising the administration of an effective amount into the subject of an inhibitor or selective inhibitor of mitochondrial production of ROS.

Another object of the present invention is a method for treating and/or preventing; or for the treatment and/or prevention of pulmonary hypertension in a subject in need thereof without inhibiting cytosolic ROS production, comprising the administration of an effective amount into the subject of an inhibitor or selective inhibitor of mitochondrial production of ROS.

Another object of the present invention is a method for treating and/or preventing; or for the treatment and/or prevention of ischemia-reperfusion injury in a subject in need thereof, comprising the administration of an effective amount into the subject of an inhibitor or selective inhibitor of mitochondrial production of ROS.

Another object of the present invention is a method for treating and/or preventing; or for the treatment and/or prevention of ischemia-reperfusion injury in a subject in need thereof by acting on mitochondria at site $I_Q$ of complex I, comprising the administration of an effective amount into the subject of an inhibitor or selective inhibitor of mitochondrial production of ROS.

Another object of the present invention is a method for treating and/or preventing; or for the treatment and/or prevention of ischemia-reperfusion injury in a subject in need thereof without inhibiting cytosolic ROS production, comprising the administration of an effective amount into the subject of an inhibitor or selective inhibitor of mitochondrial production of ROS.

Another object of the present invention is a method for treating and/or preventing; or for the treatment and/or prevention of aging diseases in a subject in need thereof, comprising the administration of an effective amount into the subject of an inhibitor or selective inhibitor of mitochondrial production of ROS.

Another object of the present invention is a method for treating and/or preventing; or for the treatment and/or prevention of aging diseases in a subject in need thereof by acting on mitochondria at site $I_Q$ of complex I, comprising the administration of an effective amount into the subject of an inhibitor or selective inhibitor of mitochondrial production of ROS.

Another object of the present invention is a method for treating and/or preventing; or for the treatment and/or prevention of aging diseases in a subject in need thereof without inhibiting cytosolic ROS production, comprising the administration of an effective amount into the subject of an inhibitor or selective inhibitor of mitochondrial production of ROS.

Another object of the present invention is a method for increasing insulin secretion in a subject in need thereof, comprising the administration of an effective amount into the subject of an inhibitor or selective inhibitor of mitochondrial production of ROS.

Another object of the present invention is a method for increasing insulin secretion in a subject in need thereof by acting on mitochondria at site $I_Q$ of complex I, comprising administrating an effective amount of an inhibitor or selective inhibitor of mitochondrial production of ROS.

Another object of the present invention is a method for increasing insulin secretion in a subject in need thereof without inhibiting cytosolic ROS production, comprising administrating an effective amount of an inhibitor or selective inhibitor of mitochondrial production of ROS.

Another object of the present invention is a method for protecting neurons in a subject in need thereof, comprising the administration of an effective amount into the subject of an inhibitor or selective inhibitor of mitochondrial production of ROS.

Another object of the present invention is a method for protecting neurons in a subject in need thereof by acting on mitochondria at site $I_Q$ of complex I, comprising administrating an effective amount of an inhibitor or selective inhibitor of mitochondrial production of ROS.

Another object of the present invention is a method for protecting neurons in a subject in need thereof without inhibiting cytosolic ROS production, comprising administrating an effective amount of an inhibitor or selective inhibitor of mitochondrial production of ROS.

Another object of the present invention is a method for preserving organs, biological tissues and/or living cells, preferably before a transplantation procedure, comprising contacting said organs, biological tissues and/or living cells with an inhibitor or selective inhibitor of mitochondrial production of ROS.

Another object of the present invention is a method for preserving organs, biological tissues and/or living cells, preferably before a transplantation procedure, by acting on mitochondria at site $I_Q$ of complex I, comprising contacting said organs, biological tissues and/or living cells with an inhibitor or selective inhibitor of mitochondrial production of ROS.

Another object of the present invention is a method for preserving organs, biological tissues and/or living cells, preferably before a transplantation procedure, without inhibiting cytosolic ROS production, comprising contacting said organs, biological tissues and/or living cells with an inhibitor or selective inhibitor of mitochondrial production of ROS.

Another object of the invention is an inhibitor or selective inhibitor of mitochondrial production of ROS for inhibiting free oxygen radicals' production in a subject in need thereof by acting on mitochondria at site $I_Q$ of complex I.

Another object of the invention is an inhibitor or selective inhibitor of mitochondrial production of ROS for inhibiting free oxygen radicals' production in a subject in need thereof without inhibiting cytosolic ROS production.

Another object of the invention is an inhibitor or selective inhibitor of mitochondrial production of ROS for treating and/or preventing; or for use in treating and/or preventing at least one free oxygen radicals-related disease.

Another object of the invention is an inhibitor or selective inhibitor of mitochondrial production of ROS for treating and/or preventing; or for use in treating and/or preventing at least one free oxygen radicals-related disease by acting on mitochondria at site $I_Q$ of complex I.

Another object of the invention is an inhibitor or selective inhibitor of mitochondrial production of ROS for treating and/or preventing; or for use in treating and/or preventing at least one free oxygen radicals-related disease without inhibiting cytosolic ROS production.

Another object of the present invention is an inhibitor or selective inhibitor of mitochondrial production of ROS for treating and/or preventing; or for use in treating and/or preventing at least one free oxygen-radicals related cardiovascular disease.

Another object of the invention is an inhibitor or selective inhibitor of mitochondrial production of ROS for treating and/or preventing; or for use in treating and/or preventing at least one free oxygen-radicals related cardiovascular disease by acting on mitochondria at site $I_Q$ of complex I.

Another object of the invention is an inhibitor or selective inhibitor of mitochondrial production of ROS for treating and/or preventing; or for use in treating and/or preventing at least one free oxygen-radicals related cardiovascular disease without inhibiting cytosolic ROS production.

Another object of the present invention is an inhibitor or selective inhibitor of mitochondrial production of ROS for treating and/or preventing; or for use in treating and/or preventing myocardial infarction.

Another object of the present invention is an inhibitor or selective inhibitor of mitochondrial production of ROS for treating and/or preventing; or for use in treating and/or preventing myocardial infarction by acting on mitochondria at site $I_Q$ of complex I.

Another object of the present invention is an inhibitor or selective inhibitor of mitochondrial production of ROS for treating and/or preventing; or for use in treating and/or preventing myocardial infarction without inhibiting cytosolic ROS production.

Another object of the present invention is an inhibitor or selective inhibitor of mitochondrial production of ROS for treating and/or preventing; or for use in treating and/or preventing heart failure.

Another object of the present invention is an inhibitor or selective inhibitor of mitochondrial production of ROS for treating and/or preventing; or for use in treating and/or preventing heart failure by acting on mitochondria at site $I_Q$ of complex I.

Another object of the present invention is an inhibitor or selective inhibitor of mitochondrial production of ROS for treating and/or preventing; or for use in treating and/or preventing heart failure without inhibiting cytosolic ROS production.

Another object of the present invention is an inhibitor or selective inhibitor of mitochondrial production of ROS for treating and/or preventing; or for use in treating and/or preventing cardiac toxicity, preferably cardiac toxicity of anthracyclines, cardiac toxicity of anti-cancer drugs, cardiac toxicity of quinolones and/or cardiac toxicity of antiviral drugs, more preferably cardiac toxicity of anthracyclines.

Another object of the present invention is an inhibitor or selective inhibitor of mitochondrial production of ROS for treating and/or preventing; or for use in treating and/or preventing cardiac toxicity, preferably cardiac toxicity of anthracyclines, cardiac toxicity of anti-cancer drugs, cardiac toxicity of quinolones and/or cardiac toxicity of antiviral drugs, more preferably cardiac toxicity of anthracyclines by acting on mitochondria at site $I_Q$ of complex I.

Another object of the present invention is an inhibitor or selective inhibitor of mitochondrial production of ROS for treating and/or preventing; or for use in treating and/or preventing cardiac toxicity, preferably cardiac toxicity of anthracyclines, cardiac toxicity of anti-cancer drugs, cardiac toxicity of quinolones and/or cardiac toxicity of antiviral drugs, more preferably cardiac toxicity of anthracyclines without inhibiting cytosolic ROS production.

Another object of the invention is an inhibitor or selective inhibitor of mitochondrial production of ROS for treating and/or preventing; or for use in treating and/or preventing pulmonary hypertension.

Another object of the invention is an inhibitor or selective inhibitor of mitochondrial production of ROS for treating and/or preventing; or for use in treating and/or preventing pulmonary hypertension by acting on mitochondria at site $I_Q$ of complex I.

Another object of the invention is an inhibitor or selective inhibitor of mitochondrial production of ROS for treating and/or preventing; or for use in treating and/or preventing pulmonary hypertension without inhibiting cytosolic ROS production.

Another object of the present invention is an inhibitor or selective inhibitor of mitochondrial production of ROS for treating and/or preventing; or for use in treating and/or preventing ischemia-reperfusion injury.

Another object of the present invention is an inhibitor or selective inhibitor of mitochondrial production of ROS for treating and/or preventing; or for use in treating and/or preventing ischemia-reperfusion injury by acting on mitochondria at site I of complex I.

Another object of the present invention is an inhibitor or selective inhibitor of mitochondrial production of ROS for treating and/or preventing; or for use in treating and/or preventing ischemia-reperfusion injury without inhibiting cytosolic ROS production.

Another object of the invention is an inhibitor or selective inhibitor of mitochondrial production of ROS for treating and/or preventing; or for use in treating and/or preventing aging diseases.

Another object of the invention is an inhibitor or selective inhibitor of mitochondrial production of ROS for treating and/or preventing; or for use in treating and/or preventing aging diseases by acting on mitochondria at site $I_Q$ of complex I.

Another object of the invention is an inhibitor or selective inhibitor of mitochondrial production of ROS for treating and/or preventing; or for use in treating and/or preventing aging diseases without inhibiting cytosolic ROS production.

Another object of the invention is an inhibitor or selective inhibitor of mitochondrial production of ROS for increasing insulin secretion.

Another object of the invention is an inhibitor or selective inhibitor of mitochondrial production of ROS for increasing insulin secretion by acting on mitochondria at site $I_Q$ of complex I.

Another object of the invention is an inhibitor or selective inhibitor of mitochondrial production of ROS for increasing insulin secretion without inhibiting cytosolic ROS production.

Another object of the invention is an inhibitor or selective inhibitor of mitochondrial production of ROS for protecting neurons.

Another object of the invention is an inhibitor or selective inhibitor of mitochondrial production of ROS for protecting neurons by acting on mitochondria at site $I_Q$ of complex I.

Another object of the invention is an inhibitor or selective inhibitor of mitochondrial production of ROS for protecting neurons without inhibiting cytosolic ROS production.

Another object of the invention is an inhibitor or selective inhibitor of mitochondrial production of ROS for preserving organs, biological tissues and/or living cells, preferably before a transplantation procedure.

Another object of the invention is an inhibitor or selective inhibitor of mitochondrial production of ROS for preserving organs, biological tissues and/or living cells, preferably before a transplantation procedure, by acting on mitochondria at site $I_Q$ of complex L.

Another object of the invention is an inhibitor or selective inhibitor of mitochondrial production of ROS for preserving organs, biological tissues and/or living cells, preferably before a transplantation procedure, without inhibiting cytosolic ROS production.

Another object of the invention is the use of an inhibitor or selective inhibitor of mitochondrial production of ROS for inhibiting free oxygen radicals' production in a subject in need thereof by acting on mitochondria at site $I_Q$ of complex L.

Another object of the invention is the use of an inhibitor or selective inhibitor of mitochondrial production of ROS for inhibiting free oxygen radicals' production in a subject in need thereof without inhibiting cytosolic ROS production.

Another object of the invention is the use of an inhibitor or selective inhibitor of mitochondrial production of ROS for treating and/or preventing at least one free oxygen radicals-related disease.

Another object of the invention is the use of an inhibitor or selective inhibitor of mitochondrial production of ROS for treating and/or preventing at least one free oxygen radicals-related disease by acting on mitochondria at site $I_Q$ of complex L.

Another object of the invention is the use of an inhibitor or selective inhibitor of mitochondrial production of ROS for treating and/or preventing at least one free oxygen radicals-related disease without inhibiting cytosolic ROS production.

Another object of the invention is the use of an inhibitor or selective inhibitor of mitochondrial production of ROS for treating and/or preventing at least one free oxygen radicals-related cardiovascular disease.

Another object of the invention is the use of an inhibitor or selective inhibitor of mitochondrial production of ROS for treating and/or preventing at least one free oxygen radicals-related cardiovascular disease by acting on mitochondria at site $I_Q$ of complex I.

Another object of the invention is the use of an inhibitor or selective inhibitor of mitochondrial production of ROS for treating and/or preventing at least one free oxygen radicals-related cardiovascular disease without inhibiting cytosolic ROS production.

Another object of the present invention is the use of an inhibitor or selective inhibitor of mitochondrial production of ROS for treating and/or preventing myocardial infarction.

Another object of the present invention is the use of an inhibitor or selective inhibitor of mitochondrial production of ROS for treating and/or preventing myocardial infarction by acting on mitochondria at site $I_Q$ of complex I.

Another object of the present invention is the use of an inhibitor or selective inhibitor of mitochondrial production of ROS for treating and/or preventing myocardial infarction without inhibiting cytosolic ROS production.

Another object of the present invention is the use of an inhibitor or selective inhibitor of mitochondrial production of ROS for treating and/or preventing heart failure.

Another object of the present invention is the use of an inhibitor or selective inhibitor of mitochondrial production of ROS for treating and/or preventing heart failure by acting on mitochondria at site $I_Q$ of complex I.

Another object of the present invention is the use of an inhibitor or selective inhibitor of mitochondrial production of ROS for treating and/or preventing heart failure without inhibiting cytosolic ROS production.

Another object of the present invention is the use of an inhibitor or selective inhibitor of mitochondrial production of ROS for treating and/or preventing cardiac toxicity, preferably cardiac toxicity of anthracyclines, cardiac toxicity of anti-cancer drugs, cardiac toxicity of quinolones and/or cardiac toxicity of antiviral drugs, more preferably cardiac toxicity of anthracyclines.

Another object of the present invention is the use of an inhibitor or selective inhibitor of mitochondrial production of ROS for treating and/or preventing cardiac toxicity, preferably cardiac toxicity of anthracyclines, cardiac toxicity of anti-cancer drugs, cardiac toxicity of quinolones and/or cardiac toxicity of antiviral drugs, more preferably cardiac toxicity of anthracyclines by acting on mitochondria at site $I_Q$ of complex I.

Another object of the present invention is the use of an inhibitor or selective inhibitor of mitochondrial production of ROS for treating and/or preventing cardiac toxicity, preferably cardiac toxicity of anthracyclines, cardiac toxicity of anti-cancer drugs, cardiac toxicity of quinolones and/or cardiac toxicity of antiviral drugs, more preferably cardiac toxicity of anthracyclines without inhibiting cytosolic ROS production.

Another object of the invention is the use of an inhibitor or selective inhibitor of mitochondrial production of ROS for treating and/or preventing pulmonary hypertension.

Another object of the invention is the use of an inhibitor or selective inhibitor of mitochondrial production of ROS for treating and/or preventing pulmonary hypertension by acting on mitochondria at site $I_Q$ of complex I.

Another object of the invention is the use of an inhibitor or selective inhibitor of mitochondrial production of ROS for treating and/or preventing pulmonary hypertension without inhibiting cytosolic ROS production.

Another object of the present invention is the use of an inhibitor or selective inhibitor of mitochondrial production of ROS for treating and/or preventing ischemia-reperfusion injury.

Another object of the present invention is the use of an inhibitor or selective inhibitor of mitochondrial production of ROS for treating and/or preventing ischemia-reperfusion injury by acting on mitochondria at site $I_Q$ of complex I.

Another object of the present invention is the use of an inhibitor or selective inhibitor of mitochondrial production of ROS for treating and/or preventing ischemia-reperfusion injury without inhibiting cytosolic ROS production.

Another object of the invention is the use of an inhibitor or selective inhibitor of mitochondrial production of ROS for treating and/or preventing aging diseases.

Another object of the invention is the use of an inhibitor or selective inhibitor of mitochondrial production of ROS for treating and/or preventing aging diseases by acting on mitochondria at site $I_Q$ of complex I.

Another object of the invention is the use of an inhibitor or selective inhibitor of mitochondrial production of ROS for treating and/or preventing aging diseases without inhibiting cytosolic ROS production.

Another object of the invention is the use of an inhibitor or selective inhibitor of mitochondrial production of ROS for increasing insulin secretion.

Another object of the invention is the use of an inhibitor or selective inhibitor of mitochondrial production of ROS for increasing insulin secretion by acting on mitochondria at site $I_Q$ of complex I.

Another object of the invention is the use of an inhibitor or selective inhibitor of mitochondrial production of ROS for increasing insulin secretion without inhibiting cytosolic ROS production.

Another object of the invention is the use of an inhibitor or selective inhibitor of mitochondrial production of ROS for protecting neurons.

Another object of the invention is the use of an inhibitor or selective inhibitor of mitochondrial production of ROS for protecting neurons by acting on mitochondria at site $I_Q$ of complex I.

Another object of the invention is the use of an inhibitor or selective inhibitor of mitochondrial production of ROS for protecting neurons without inhibiting cytosolic ROS production.

Another object of the invention is the use of an inhibitor or selective inhibitor of mitochondrial production of ROS for preserving organs, biological tissues and/or living cells, preferably before a transplantation procedure.

Another object of the invention is the use of an inhibitor or selective inhibitor of mitochondrial production of ROS for preserving organs, biological tissues and/or living cells, preferably before a transplantation procedure, by acting on mitochondria at site $I_Q$ of complex I.

Another object of the invention is the use of an inhibitor or selective inhibitor of mitochondrial production of ROS for preserving organs, biological tissues and/or living cells, preferably before a transplantation procedure, without inhibiting cytosolic ROS production.

Another object of the invention is the use of an inhibitor or selective inhibitor of mitochondrial production of ROS in the manufacture of a medicament for inhibiting free oxygen radicals' production in a subject in need thereof by acting on mitochondria at site $I_Q$ of complex I.

Another object of the invention is the use of an inhibitor or selective inhibitor of mitochondrial production of ROS in the manufacture of a medicament for inhibiting free oxygen radicals' production in a subject in need thereof without inhibiting cytosolic ROS production.

Another object of the invention is the use of an inhibitor or selective inhibitor of mitochondrial production of ROS in the manufacture of a medicament for the treatment and/or prevention of at least one free oxygen radicals-related disease.

Another object of the invention is the use of an inhibitor or selective inhibitor of mitochondrial production of ROS in the manufacture of a medicament for treating and/or preventing at least one free oxygen radicals-related disease by acting on mitochondria at site $I_Q$ of complex I.

Another object of the invention is the use of an inhibitor or selective inhibitor of mitochondrial production of ROS in the manufacture of a medicament for treating and/or preventing at least one free oxygen radicals-related disease without inhibiting cytosolic ROS production.

Another object of the invention is the use of an inhibitor or selective inhibitor of mitochondrial production of ROS in the manufacture of a medicament for the treatment and/or prevention of at least one free oxygen radicals-related cardiovascular disease.

Another object of the invention is the use of an inhibitor or selective inhibitor of mitochondrial production of ROS in the manufacture of a medicament for treating and/or preventing at least one free oxygen radicals-related cardiovascular disease by acting on mitochondria at site $I_Q$ of complex I.

Another object of the invention is the use of an inhibitor or selective inhibitor of mitochondrial production of ROS in the manufacture of a medicament for treating and/or preventing at least one free oxygen radicals-related cardiovascular disease without inhibiting cytosolic ROS production.

Another object of the present invention is the use of an inhibitor or selective inhibitor of mitochondrial production of ROS in the manufacture of a medicament for treating and/or preventing myocardial infarction.

Another object of the present invention is the use of an inhibitor or selective inhibitor of mitochondrial production of ROS in the manufacture of a medicament for treating and/or preventing myocardial infarction by acting on mitochondria at site $I_Q$ of complex I.

Another object of the present invention is the use of an inhibitor or selective inhibitor of mitochondrial production of ROS in the manufacture of a medicament for treating and/or preventing myocardial infarction without inhibiting cytosolic ROS production.

Another object of the present invention is the use of an inhibitor or selective inhibitor of mitochondrial production of ROS in the manufacture of a medicament for treating and/or preventing heart failure.

Another object of the present invention is the use of an inhibitor or selective inhibitor of mitochondrial production of ROS in the manufacture of a medicament for treating and/or preventing heart failure by acting on mitochondria at site $I_Q$ of complex I.

Another object of the present invention is the use of an inhibitor or selective inhibitor of mitochondrial production of ROS in the manufacture of a medicament for treating and/or preventing heart failure without inhibiting cytosolic ROS production.

Another object of the present invention is the use of an inhibitor or selective inhibitor of mitochondrial production of ROS in the manufacture of a medicament for treating and/or preventing cardiac toxicity, preferably cardiac toxicity of anthracyclines, cardiac toxicity of anti-cancer drugs, cardiac toxicity of quinolones and/or cardiac toxicity of antiviral drugs, more preferably cardiac toxicity of anthracyclines.

Another object of the present invention is the use of an inhibitor or selective inhibitor of mitochondrial production of ROS in the manufacture of a medicament for treating and/or preventing cardiac toxicity, preferably cardiac toxicity of anthracyclines, cardiac toxicity of anti-cancer drugs, cardiac toxicity of quinolones and/or cardiac toxicity of antiviral drugs, more preferably cardiac toxicity of anthracyclines by acting on mitochondria at site $I_Q$ of complex I.

Another object of the present invention is the use of an inhibitor or selective inhibitor of mitochondrial production of ROS in the manufacture of a medicament for treating and/or preventing cardiac toxicity, preferably cardiac toxicity of anthracyclines, cardiac toxicity of anti-cancer drugs, cardiac toxicity of quinolones and/or cardiac toxicity of antiviral drugs, more preferably cardiac toxicity of anthracyclines without inhibiting cytosolic ROS production.

Another object of the invention is the use of an inhibitor or selective inhibitor of mitochondrial production of ROS in the manufacture of a medicament for the treatment and/or prevention of pulmonary hypertension.

Another object of the invention is the use of an inhibitor or selective inhibitor of mitochondrial production of ROS in the manufacture of a medicament for treating and/or preventing pulmonary hypertension by acting on mitochondria at site $I_Q$ of complex I.

Another object of the invention is the use of an inhibitor or selective inhibitor of mitochondrial production of ROS in the manufacture of a medicament for treating and/or preventing pulmonary hypertension without inhibiting cytosolic ROS production.

Another object of the present invention is the use of an inhibitor or selective inhibitor of mitochondrial production of ROS in the manufacture of a medicament for treating and/or preventing ischemia-reperfusion injury.

Another object of the present invention is the use of an inhibitor or selective inhibitor of mitochondrial production of ROS in the manufacture of a medicament for treating and/or preventing ischemia-reperfusion injury by acting on mitochondria at site $I_Q$ of complex I.

Another object of the present invention is the use of an inhibitor or selective inhibitor of mitochondrial production of ROS in the manufacture of a medicament for treating and/or preventing ischemia-reperfusion injury without inhibiting cytosolic ROS production.

Another object of the invention is the use of an inhibitor or selective inhibitor of mitochondrial production of ROS in the manufacture of a medicament for the treatment and/or prevention of aging diseases.

Another object of the invention is the use of an inhibitor or selective inhibitor of mitochondrial production of ROS in the manufacture of a medicament for treating and/or preventing aging diseases by acting on mitochondria at site $I_Q$ of complex I.

Another object of the invention is the use of an inhibitor or selective inhibitor of mitochondrial production of ROS in the manufacture of a medicament for treating and/or preventing aging diseases without inhibiting cytosolic ROS production.

Another object of the invention is the use of an inhibitor or selective inhibitor of mitochondrial production of ROS in the manufacture of a medicament for increase of insulin secretion.

Another object of the invention is the use of an inhibitor or selective inhibitor of mitochondrial production of ROS in the manufacture of a medicament for increasing insulin secretion by acting on mitochondria at site $I_Q$ of complex I.

Another object of the invention is the use of an inhibitor or selective inhibitor of mitochondrial production of ROS in the manufacture of a medicament for increasing insulin secretion without inhibiting cytosolic ROS production.

Another object of the invention is the use of an inhibitor or selective inhibitor of mitochondrial production of ROS in the manufacture of a medicament for the protection of neurons.

Another object of the invention is the use of an inhibitor or selective inhibitor of mitochondrial production of ROS in the manufacture of a medicament for protecting neurons by acting on mitochondria at site $I_Q$ of complex I.

Another object of the invention is the use of an inhibitor or selective inhibitor of mitochondrial production of ROS in the manufacture of a medicament for protecting neurons without inhibiting cytosolic ROS production.

Another object of the invention is the use of an inhibitor or selective inhibitor of mitochondrial production of ROS in the manufacture of a medicament for preserving organs, biological tissues and/or living cells, preferably before a transplantation procedure.

Another object of the invention is the use of an inhibitor or selective inhibitor of mitochondrial production of ROS in the manufacture of a medicament for preserving organs, biological tissues and/or living cells, preferably before a transplantation procedure, by acting on mitochondria at site $I_Q$ of complex I.

Another object of the invention is the use of an inhibitor or selective inhibitor of mitochondrial production of ROS in the manufacture of a medicament for preserving organs, biological tissues and/or living cells, preferably before a transplantation procedure, without inhibiting cytosolic ROS production.

BRIEF DESCRIPTION OF THE DRAWINGS

FIG. 19B presents the evolution of mitochondrial oxidation rates during the different respiratory states described above (Succ/ROT: GM substrates, succinate and rotenone) in the presence of increasing concentrations of AOX in DMSO.

FIG. 25A shows photographs of the dyed cells in the lower compartment for the different conditions (control, 5 µM AOX, 10 µM AOX and 10 µM NAC [N-acetyl cysteine]). FIG. 25B is an histogram showing the results of FIG. 25A.

FIG. 28 shows the effect of AOL, AOX and Oltipraz (0 to 80 μM) on ROS/$H_2O_2$ production by sites $I_Q$ and $III_{QO}$ of isolated mitochondria, when individually targeted using the combination of succinate (energy substrate of respiratory complex 2) and known inhibitors of respiratory chain, namely for site $I_Q$, 10 mM succinate alone and for site $III_{Qouter}$, 10 mM succinate, 4 μM rotenone and 2.5 μM antimycin A.

FIG. 29 shows the effect of AOX analogs (Cp1; Cp2; Cp3; Cp4; Cp5; Cp6a; Cp8; Cp9a) (from 0 to 25 μM) on ROS/$H_2O_2$ production by sites $I_Q$ and $III_{QO}$ of isolated mitochondria, when individually targeted using the combination of succinate (energy substrate of respiratory complex 2) and known inhibitors of respiratory chain, namely for site $I_Q$, 10 mM succinate alone and for site $III_{Qouter}$, 10 mM succinate, 4 μM rotenone and 2.5 μM antimycin A.

EXAMPLES

Figure 1:
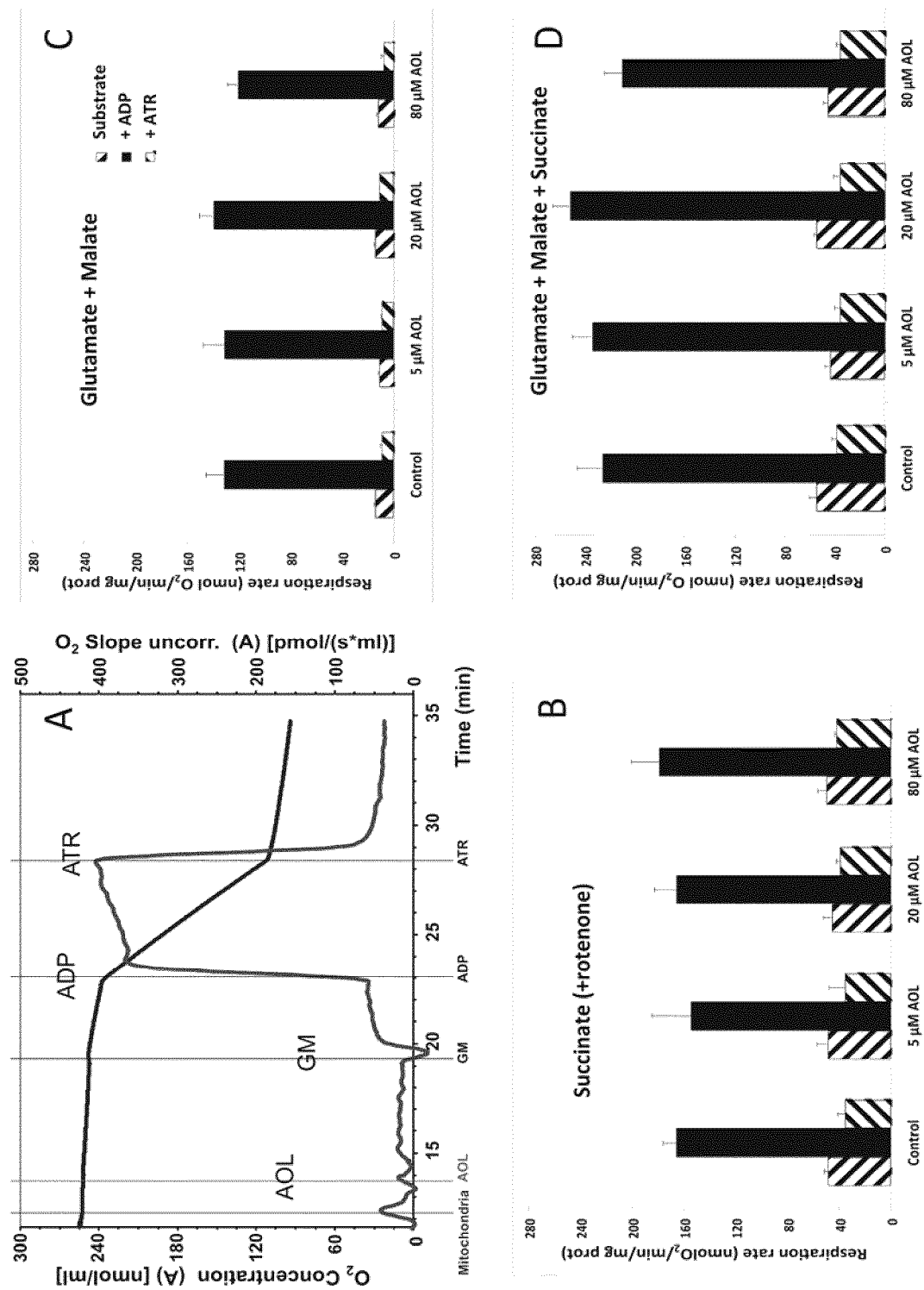
FIG. 1 illustrates the absence of effect of AOL (5-(4-methoxyphenyl)-3H-1,2-dithiole-3-thione) on mitochondrial respiration. Panel A: After incubation in the presence of AOL (20 μM in this example), isolated mitochondria from rat heart were oxidizing glutamate+malate (GM) as substrate. Phosphorylation was triggered by adenosine diphosphate (ADP) and stopped by atractyloside (ATR), a specific inhibitor of adenine translocator. Panels B to D: The classical study of mitochondrial oxidative phosphorylation in the presence of various respiratory substrates was carried out in the presence of increasing concentrations of AOL (from 5 to 80 μM). There were no statistical differences in mitochondrial respiration under the different energetic states after addition of AOL. Oxidation rate after ADP addition reflects the adenosine triphosphate (ATP) synthesis activity of isolated mitochondria.

The present invention is further illustrated by the following examples.

Chemistry Examples

General Experimental Procedures

Reagents and Solvents

All reagents of synthetic grade and solvents were used as supplied. The solvents used in reactions were dried, distilled if required in accordance with the state of the art. Some solvents were commercially available as dry and were used as such.

Reaction Conditions

When dry conditions were required, glassware was oven dried and reactions were carried out under a nitrogen atmosphere. Room temperature (r.t.) refers to 20-25° C. Reaction temperatures of −78° C. were obtained using solid C02 and acetone. For those at 0° C., an ice bath was employed and where heat was required an oil bath with contact thermometer was used.

Reactions were monitored by TLC. TLC was carried out using Merck, DC Kieselgel 60 $F_{254}$ plates UV254 pre-coated aluminum sheets with silica gel and fluorescent indicator. Indicators used included ethanolic phosphomolybdic acid solution Flash Chromatography Silica gel, MN Kieselgel 60, 15-40 microns grade from Macherey-Nagel was used in the purification of crude products by flash column chromatography. The samples were either applied directly to the top of the silica/solvent column or applied as dry silica gel slurry.

Automated Flash Chromatography

Teledyne Isco Combiflash Companion™ purification system Crude samples were dissolved in a small amount of suitable solvent and applied to RediSep® prepacked columns. The column was placed within the Teledyne Isco Combiflash Companion® purification system and automated purification was carried out using a solvent gradient program. The system was used either with the automated fraction collection facility where compounds were detected by UV or by collecting all fractions.

Nuclear Magnetic Resonance Spectroscopy (NMR)

NMR was recorded on Bruker UltraShield instruments operating at 400 MHz ($^1$H), and 100 MHz ($^{13}$C). Calibration was carried out using the residual solvent shift from the deuterated solvent. When $CDCl_3$ was employed as the solvent, calibration was carried out on this solvent signal at 7.26 ($^1$H) and 77.16 ($^{13}$C). When aromatics were present in the sample to be analyzed, $Me_4Si$ was added to $CDCl_3$ and the spectra were calibrated at 0.0 (1H). When D20 was used, the water signal was designated as the internal reference at 4.79 ppm (1H). For $CD_3OD$, the internal reference was designated at 3.31 ppm ($^1$H) and 49.0 ppm ($^{13}$C NMR). For $(CD_3)_2SO$ the internal reference was designated at 2.50 ppm ($^1$H) and 39.5 ppm ($^{13}$C). For $^{19}$F, $CFCl_3$ as an external reference was used. Chemical shifts are reported in parts per million (ppm) and coupling constants are given in Hertz (Hz). The abbreviations for the multiplicity of the proton and carbon signals are as follows: s singlet, d doublet, dd doublet of doublet, dt doublet of triplets, ddt doublet of doublet of triplets, t triplet, tt triplet of triplets, q, quintet, m multiplet.

Mass Spectroscopy (MS) and Liquid Chromatography Coupled to Tandem Mass Spectrometry (LC-MS) Analysis Mass analysis was carried out on a Waters 3100 Mass detector, Waters Alliance 2695. 1 μg sensitivity with either ESI or APCI. 10,000 Da/sec scan speeds up to 2,000 Da for full compatibility with seconds wide fast LC peaks. Dual orthogonal sampling ionization with ZSpray™ source. Multiple detection strategies available with supported Tunable UV (TUV), Photodiode Array (PDA), and Evaporative Light Scattering (ELS) optical detectors. Or mass analysis was carried out on UPLC/MS: Xevo G2 Qtof The Xevo G2 QT of mass spectrometer, with UPLC®/MSE and QuanT of technology.

Melting Point Analyses

Melting points were measured on a STUART SMP3 instrument.

High Performance Liquid Chromatography (HPLC)

HPLC-DAD analyses were carried out on a Waters analytical HPLC system equipped with suitable analytical column, Empower software, Waters Delta 600 Multisolvent delivery system and a photodiode array detector (Waters 2996) and/or refractometer, a system controller (Waters 600), and a Rheodyne injector 7725i with a 20 μL sample loop was used.

Synthesis of Intermediate Compounds (C)

General procedure A. A 100 mL round bottom flask fitted with magnetic stirrer is charged with appropriate commercial arylethanone and dimethylcarbonate. Sodium hydride (60% in mineral oil) is added slowly with stirring and the whole is refluxed overnight. The mixture is poured into water, acidified with HCl (2M) and extracted with ethyl acetate. The organic layer is washed with water (50 mL) and saturated brine solution (50 mL). The organic layer is dried over anhydrous $Na_2SO_4$ and the solvent is removed under reduced pressure. The crude material is purified by silica gel column chromatography using suitable solvent to give the corresponding methyl 3-oxo-3-arylpropanoate.

Intermediates 7, 11 and 13 were synthesized using general alkylation procedure A.

Intermediate 7: methyl 5-(3-methoxy-3-oxopropanoyl)-1H-indole-1-carboxylate

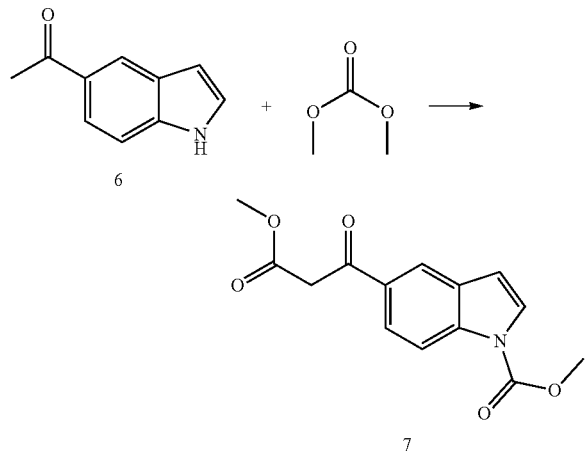

The reaction was carried out according to the general alkylation procedure A, using 6 as arylethanone (1.03 g, 6.47 mmol), dimethylcarbonate (12 mL) and sodium hydride (2.5 g, 64.7 mmol). After workup and purification, compound 7 was obtained (m=1.4 g, 78%). $^1$H NMR (400 MHz, DMSO-$D_6$) δ(ppm) 8.30 (d, J=1.4 Hz, 1H), 7.78 (dd, J=8.7, 1.7 Hz, 1), 7.55 (d, J=8.7 Hz, 1H), 7.48 (d, J=3.1 Hz, 1H), 6.64 (dd, J=3.1, 0.7 Hz, 1H), 4.23 (s, 2H), 3.84 (s, 3H), 3.66 (s, 3H).

Intermediate 11: methyl 3-(2-hydroxybenzo[d]oxazol-5-yl)-3-oxopropanoate

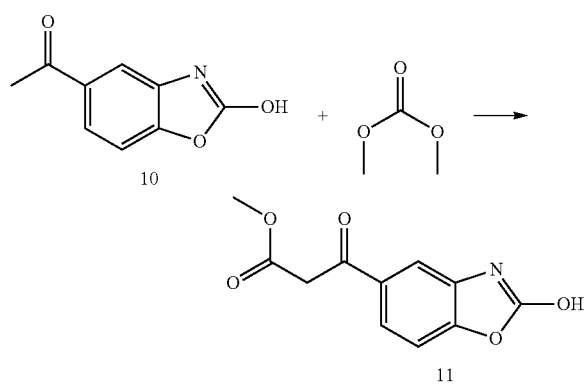

The reaction was carried out according to the general alkylation procedure A, using 10 as arylethanone (1.9 g, 10.7 mmol), dimethylcarbonate (24 mL) and sodium hydride (4.75 g, 118 mmol). After workup and purification, compound 11 was obtained (m=580 mg, 23%). $^1$H NMR (400 MHz, DMSO-$D_6$) δ(ppm) 11.94 (s, 2H), 7.77 (dd, J=8.4, 1.8 Hz, 2H), 7.58 (d, J=1.7 Hz, 2H), 7.44 (d, J=8.4 Hz, 2H), 4.23 (s, 3H), 3.64 (s, 6H).

Intermediate 13: methyl 3-(benzofuran-5-yl)-3-oxopropanoate

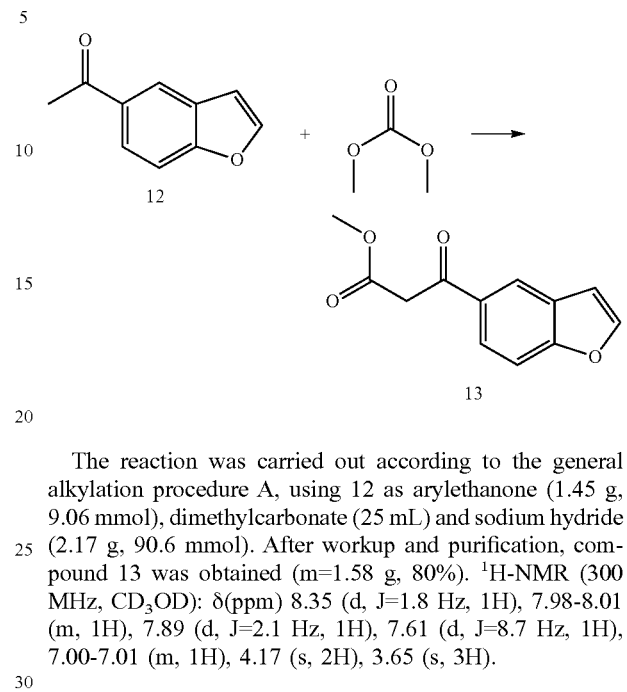

The reaction was carried out according to the general alkylation procedure A, using 12 as arylethanone (1.45 g, 9.06 mmol), dimethylcarbonate (25 mL) and sodium hydride (2.17 g, 90.6 mmol). After workup and purification, compound 13 was obtained (m=1.58 g, 80%). $^1$H-NMR (300 MHz, $CD_3OD$): δ(ppm) 8.35 (d, J=1.8 Hz, 1H), 7.98-8.01 (m, 1H), 7.89 (d, J=2.1 Hz, 1H), 7.61 (d, J=8.7 Hz, 1H), 7.00-7.01 (m, 1H), 4.17 (s, 2H), 3.65 (s, 3H).

Intermediate 9: methyl 3-(2-hydroxybenzo[d]thiazol-6-yl)-3-oxopropanoate

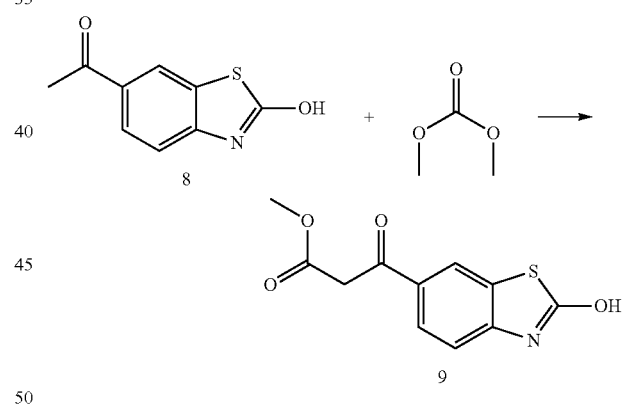

A 100 mL round bottom flask fitted with magnetic stirrer was charged with Sodium hydride (60% in mineral oil) (1 g, 48 mmol), dimethylcarbonate (4.2 mL) and tetrahydrofuran (30 mL). The commercial arylethanone 8 (1.94 g, 10 mmol) in tetrahydrofuran (30 mL) was added slowly with stirring and the whole was refluxed for 72 h. The mixture was slowly poured into water, acidified with saturated ammonium chloride (50 mL) and extracted with ethyl acetate. The organic layer was washed with water (50 mL) and dried over anhydrous $Na_2SO_4$. After evaporation under reduce pressure, the crude material was purified by crystallization in ethyl acetate to give the corresponding methyl 3-oxo-3-arylpropanoate 9 (m=1.89 g, 75%). $^1$H NMR (400 MHz, DMSO-$D_6$) δ(ppm) 12.33 (s, 1H), 8.24 (d, J=1.7 Hz, 1H), 7.89 (dd, J=8.4, 1.8 Hz, 1H), 7.22 (d, J=8.4 Hz, 1H), 4.17 (s, 2H), 3.65 (s, 3H).

Synthesis of compound Cp1

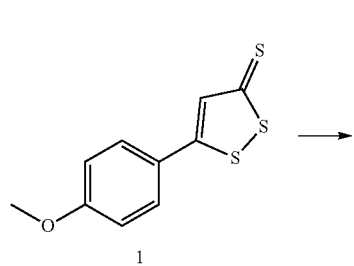

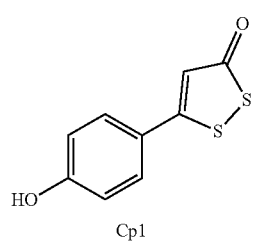

Step 1. Cp1-methoxy: 5-(4-methoxyphenyl)-3H-1,2-dithiol-3-on. Mercury (II) acetate (4 g, 12.5 mmol) was added to a solution of commercial dithione 1 (1 g, 4.16 mmol) in mixture of acetic acid (v=25 mL) and chloroform (v=80 mL). The reaction mixture was stirred at room temperature overnight. The whole was filtrated and evaporated. The obtained solid was chromatographed on silica gel (petroleum ether:acetone=90:10) to give a yellow solid Cp1-methoxy (800 mg, 85% yield). $^1$H NMR (400 MHz, CDCl$_3$) δ(ppm) 7.59 (d, J=8.9 Hz, 2H), 6.98 (d, J=8.9 Hz, 2H), 6.77 (s, 1H), 3.88 (s, 3H). $^{13}$C NMR (101 MHz, CDCl$_3$) δ(ppm) 194.29, 170.13, 162.52, 128.08, 125.08, 116.30, 114.75, 55.60.

Step 2. Cp1: 5-(4-hydroxyphenyl)-3H-1,2-dithiol-3-one. A mixture of methyl aryl ether Cp1-methoxy (410 mg, 1.83 mmol) and pyridine hydrochloride (630 mg, 5.5 mmol) were placed in a round bottom flask and subjected to microwave irradiation at 250 W for 5 minutes. After complete conversion, the reaction mixture was passed through a column chromatography (dichloromethane:methanol=97:3) to give the dithione Cp1 (m=70 mg, 10% yield). $^1$H NMR (400 MHz, Acetone-D$_6$) δ(ppm) 9.31 (s, 1H), 7.80-7.66 (m, 2H), 7.05-7.00 (m, 2H), 6.98 (s, 1H). $^{13}$C NMR (101 MHz, Acetone-D$_6$) δ(ppm) 192.95, 170.48, 161.08, 160.96, 128.34, 123.94, 116.25, 116.16, 115.17.

Synthesis of Compound Cp2

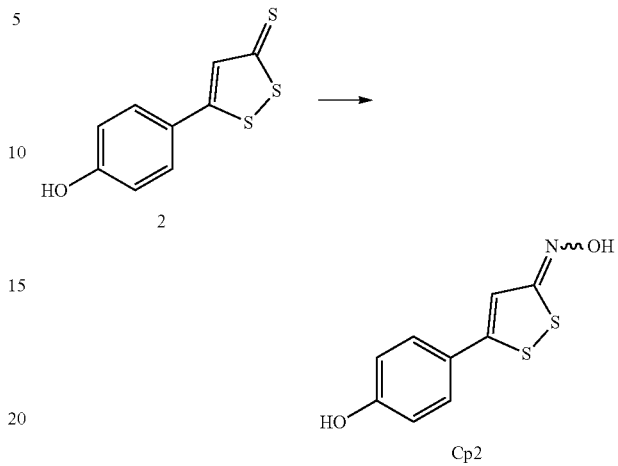

Cp2: 5-(4-hydroxyphenyl)-3H-1,2-dithiol-3-one oxime. Hydroxylamine hydrochloride (140 mg, 2 mmol) was added to a solution of commercial dithione 2 (224 mg, 1 mmol) and sodium acetate (165 mg, 2 mmol) in ethanol (v=5 mL). The reaction mixture was stirred at room temperature overnight and then concentrated under reduce pressure. The obtained solid was chromatographed on silica gel (dichloromethane) to give the dithione Cp2 (m=51 mg, 32%) as a red solid. $^1$H NMR (400 MHz, DMSO-D$_6$) δ(ppm) 11.55 (s, 1H), 10.08 (s, 1H), 7.51 (d, J=8.7 Hz, 2H), 7.07 (s, 1H), 6.84 (d, J=8.7 Hz, 2H). $^{13}$C NMR (101 MHz, DMSO-D$_6$) δ(ppm) 161.99, 159.83, 153.46, 128.36, 123.71, 116.30, 112.77.

Synthesis of Compound Cp3

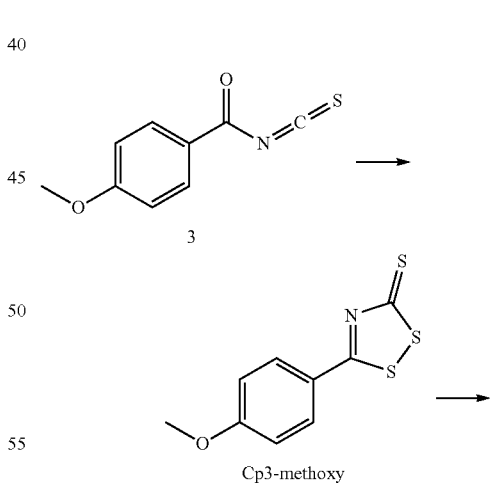

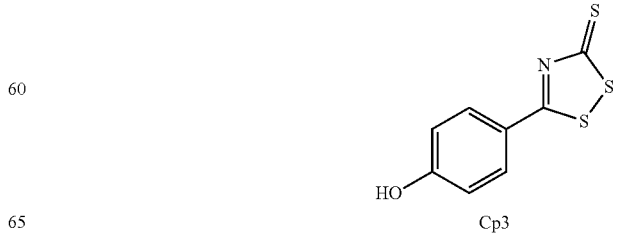

Ref.: MacDonald & McKinnon, 1967. *Can. J. Chem.* 45(11):1225-1229

Step 1. Cp3-methoxy: 5-(4-methoxyphenyl)-3H-1,2,4-dithiazole-3-thione. The commercial isothiocyanate 3 (3 g, 15.5 mol) and phosphorus pentasulfide (6 g, 13.5 mmol) in carbon disulfide (18 mL) were placed in a round bottom flask and subjected to microwave irradiation at 65 W for 15 minutes. After complete conversion, the solution was filtered and evaporated under reduced pressure. The oily residue was treated with ethanol (approximately 30 mL) and cooled to 0° C. The crude dithiones were filtered off and recrystallized from (dichloromethane:ethanol=1:1) to give a yellow solid Cp3-methoxy (m=220 mg, 7% yield). ¹H NMR (400 MHz, CDCl₃) δ(ppm) 8.12 (d, J=8.9 Hz, 2H), 7.26 (s, 1H), 7.00 (d, J=9.0 Hz, 3H), 3.92 (s, 3H). ¹³C NMR (101 MHz, DMSO-D₆) δ(ppm) 185.35, 160.71, 126.65, 119.04, 110.23, 51.10.

Step 2. Cp3: 5-(4-hydroxyphenyl)-3H-1,2,4-dithiazole-3-thione. A mixture of methyl aryl ether Cp3-methoxy (300 mg, 1.25 mmol) and dichloromethane (v=6 mL) were placed in a round bottom flask and cooled to 0° C. Boron tribromide, 1M in dichloromethane (v=6 mL, 6 mmol) was added slowly and the whole was stirred overnight. After complete conversion the reaction mixture was poured into water to give a suspension. The solid was filtered off and washed with water. Precipitation in dichloromethane gives the desired phenol Cp3 (m=270 mg, 95%). ¹H NMR (400 MHz, DMSO-D₆) δ(ppm) 11.09 (s, 1H), 8.07 (d, J=8.8 Hz, 2H), 6.97 (d, J=8.8 Hz, 2H). ¹³C NMR (101 MHz, DMSO-D₆) δ(ppm) 214.93, 191.66, 165.12, 132.15, 122.22, 117.20.

Synthesis of Compound Cp4

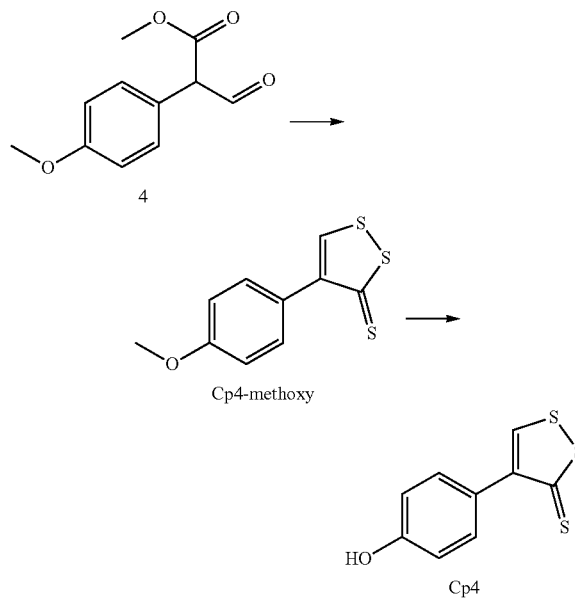

Ref.: Brown et al., 2014. *Bioorg Med Chem Lett.* 24(24): 5829-5831

Step 1. Cp4-methoxy: 4-(4-hydroxyphenyl)-3H-1,2-dithiole-3-thione. The mixture of methyl 2-(4-methoxyphenyl)-3-oxopropanoate 4 (3.79 g, 19.52 mmol), Lawesson's reagent (7.89 g, 19.52 mmol), and sulfur (313 mg, 9.59 mmol) in 250 mL of toluene were heated to reflux for 270 minutes. When the reaction was completed the mixture was filtered and the filtrate was concentrated. Purification by column chromatography (petroleum ether:acetone=10:1) allowed to a red solid. The obtained solid was washed with ether and crystalized in acetone to give Cp4-methoxy (1.56 g, 33% yield). ¹H NMR (400 MHz, CDCl₃) δ(ppm) 8.37 (s, 1H), 7.50 (d, J=8.8 Hz, 2H), 6.97 (d, J=8.8 Hz, 2H), 3.84 (s, 3H). ¹³C NMR (101 MHz, CDCl₃) δ(ppm) 214.12, 160.10, 153.04, 149.08, 130.28, 125.43, 113.88, 55.35.

Step 2. Cp4: 4-(4-hydroxyphenyl)-3H-1,2-dithiole-3-thione. A mixture of methyl aryl ether Cp4-methoxy (171 mg, 0.71 mmol) and pyridine hydrochloride (264 mg, 0.86 mmol) were placed in a round bottom flask and subjected to microwave irradiation at 250 W for 5 minutes. After complete conversion the reaction mixture was passed through a column chromatography (dichloromethane:methanol=97:3) to give the dithione Cp4 (m=51 mg, 32%). H NMR (400 MHz, Acetone-D₆) δ(ppm) 8.94 (s, 1H), 8.67 (s, 1H), 7.50 (d, J=8.6 Hz, 1H), 6.91 (d, J=8.6 Hz, 1H).

Synthesis of Compound Cp5

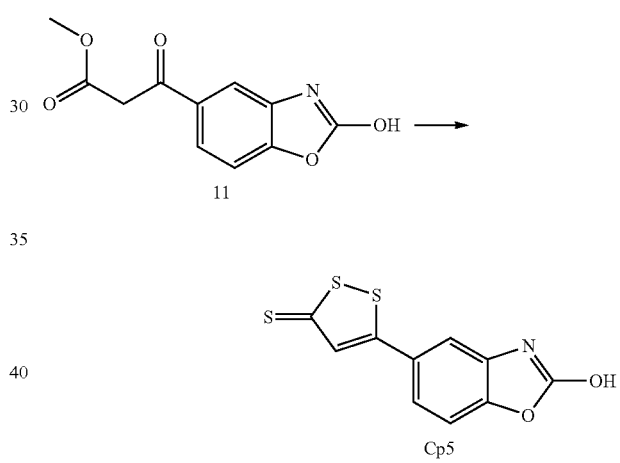

General procedure B. Phosphorus pentasulfide (0.7 mmol), sulfur (1 mmol), hexamethyldisiloxane HMDO (3 mmol) are heated in xylene (2.5 mL) at 145° C. for 5 minutes. The appropriate methyl 3-oxo-3-arylpropanoate is added by portions and the reaction mixture is refluxed for 1 h where the reaction is finished. Subsequently, the crude thiones are filtered off and the filtrates are concentrated. Purification by column chromatography and crystallizations allow to give the corresponding aryldithione.

Cp5: 5-(2-hydroxybenzo[d]oxazol-5-yl)-3H-1,2-dithiole-3-thione. The synthesis of compound Cp5 was carried out according to the general thionation procedure B, using intermediate 11 (580 mg, 2.47 mmol), P₄S₁₀ (658 mg, 1.53 mmol), sulfur (79 mg, 2.55 mmol), HMDO (0.76 mL, 7.65 mmol), and xylene (5 ml). After workup, rapid purification on silica gel (THF) and crystallization in ethanol and acetone, Cp5 (m=70 mg) was obtained as a red-dark solid. ¹H NMR (400 MHz, DMSO-D₆) δ(ppm) 12.07 (s, 1H), 7.84 (s, 1H), 7.66 (dd, J=8.4, 2.0 Hz, 1H), 7.59 (d, J=1.8 Hz, 1H), 7.45 (d, J=8.4 Hz, 1H). ¹³C NMR (101 MHz, DMSO-D₆) δ(ppm) 215.73, 173.92, 154.61, 146.65, 136.06, 132.07, 127.48, 122.31, 110.94, 108.69.

Synthesis of Compound Cp6a

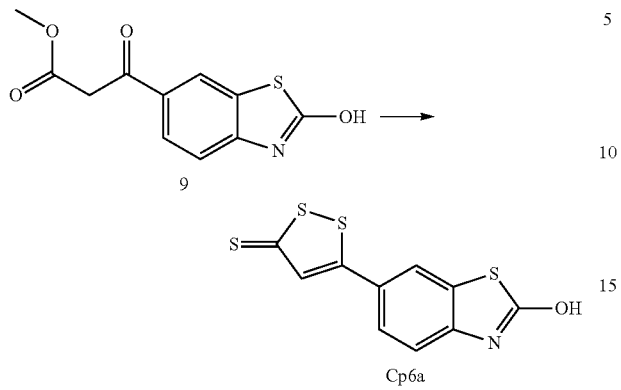

CP6a: 5-(2-hydroxybenzo[d]thiazol-6-yl)-3H-1,2-dithiole-3-thione. The reaction was carried out according to the general thionation procedure Busing intermediate 9 (700 mg, 2.55 mmol), $P_4S_{10}$ (680 mg, 1.53 mmol), sulfur (81.5 mg, 2.55 mmol), HMDO (1.63 mL, 7.65 mmol), and xylene (6 mL). After workup, rapid purification on silica gel (THF) and further purification by reverse phase on C18 (acetonitrile: water gradient) Cp6a (m=6.7 mg) was obtained as red solid. $^1$H NMR (400 MHz, DMSO-$D_6$) δ(ppm) 8.26 (d, J=1.9 Hz, 1H), 7.84 (dd, J=8.4, 1.9 Hz, 1H), 7.77 (s, 1H), 7.22 (d, J=8.4 Hz, 1H). $^3$C NMR (101 MHz, DMSO-$D_6$) δ(ppm) 173.85, 170.59, 144.13, 140.39, 135.24, 126.37, 125.48, 122.20, 112.62.

Synthesis of Compound Cp8

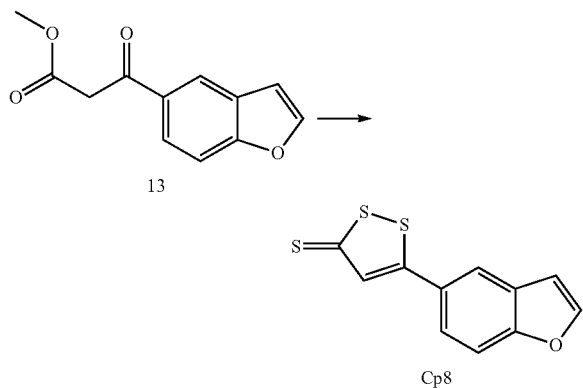

Cp8: 5-(benzofuran-5-yl)-3H-1,2-dithiole-3-thione. The reaction was carried out according to the general thionation procedure B, using intermediate 12 (1.58 g, 7.25 mmol), $P_4S_{10}$ (1.93 g, 4.35 mmol), sulfur (232 mg, 7.25 mmol), HMDO (0.76 mL, 21.7 mmol), and xylene (15 mL). After workup, rapid purification on silica gel (dichloromethane) and crystallization in ethanol and acetone, Cp8 (m=890 mg) was obtain as a yellow solid. H NMR (400 MHz, DMSO-$D_6$) δ(ppm) 8.26 (d, J=1.7 Hz, 1H), 8.14 (d, J=2.2 Hz, 1H), 7.86-7.81 (m, 3H), 7.75 (d, J=8.7 Hz, 1H), 7.06 (dd, J=2.2, 0.9 Hz, 1H). $^{13}$C NMR (101 MHz, DMSO-$D_6$) δ(ppm) 215.64, 174.84, 156.73, 148.51, 135.82, 128.82, 126.87, 124.25, 121.26, 113.04, 107.68.

Synthesis of Compound Cp9a

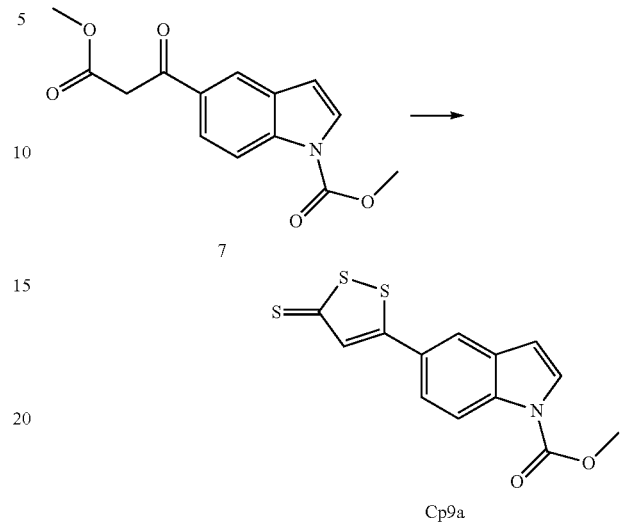

Cp9a: methyl 5-(3-thioxo-3H-1,2-dithiol-5-yl)-1H-indole-1-carboxylate. The reaction was carried out according to the general thionation procedure Busing intermediate 7 (700 mg, 2.55 mmol), $P_4S_{10}$ (680 mg, 1.53 mmol), sulfur (81.5 mg, 2.55 mmol), HMDO (1.63 mL, 7.65 mmol), and xylene (6 mL). After workup, rapid purification on silica gel (THF) and crystallization in ethanol and acetone, we have obtained Cp9a (m=55 mg) as a red-dark solid. $^1$H NMR (400 MHz, DMSO-$D_6$) δ(ppm) 8.20 (d, J=1.6 Hz, 1H), 7.81 (s, 1H), 7.69 (dd, J=8.7, 1.8 Hz, 1H), 7.59 (d, J=8.7 Hz, 1H), 7.49 (d, J=3.1 Hz, 1H), 6.59 (d, J=3.1 Hz, 1H), 3.84 (s, 3H). $^{13}$C NMR (101 MHz, DMSO-$D_6$) δ(ppm) 176.78, 138.90, 134.27, 132.59, 128.85, 122.84, 120.72, 111.52, 102.57, 34.12, 33.24, 31.09.

BIOLOGY EXAMPLES

Example 1: AOL does not Affect Mitochondrial Oxidative Phosphorylation

Material and Methods
Animal Procedures and Ethics Statement

All experiments described were carried out in agreement with the National and European Research Council Guide for the care and use of laboratory animals. P. Diolez has a valid license to conduct experiments on animals by the Service Vétérinaire de la Santé et de la Protection Animale of the Ministère de l'agriculture et de la Forêt, France (Mar. 17, 1999, license number 3308010).

Materials

All the chemicals were reagent grade, purchased from Sigma Chemical (St. Louis, Mo.), except for sucrose and NADH oxidase (that were obtained from Merck (Darmstadt, Germany)). The trithio-AnethOL compound (AOL, corresponding to 5-(4-methoxyphenyl)-3H-1,2-dithiole-3-thione) was a gift from the private company GMPO (Paris, France). 15 mM stock solution was prepared in DMSO, and kept in darkness at 0° C. for only few days.

Isolation of Mitochondria

Male Wistar rats (250-325 g; obtained from Janvier Labs, Le Genest-Saint-Isle, France) were killed by stunning and cervical dislocation, and the heart was quickly removed and washed in cold isolation medium containing 100 mM sucrose, 180 mM KCl, 50 mM Tris, 5 mM $MgCl_2$, 10 mM EDTA, and 0.1% (w/v) defatted BSA (pH 7.2).

Isolation of heart mitochondria was performed in a cold chamber. Before homogenization, hearts (about 1.5 g) were minced with scissors and treated for 5 minutes in 5 mL of the same medium supplemented with protease (2 mg of bacterial proteinase type XXIV per mL of isolation buffer) with stirring. The tissue suspension was poured into a 50-mL glass Potter homogenizer, diluted with 20 mL of isolation buffer, then homogenized for 3 minutes using a motorized Teflon pestle. The homogenate was filtered through bolting cloth (Sefar Nitex) to remove debris, and centrifuged at 8,000 g for 10 minutes. The resulting pellet was rinsed with 5 mL of isolation buffer, resuspended in 25 mL of the same buffer, then subjected to low speed centrifugation (400 g) for 8 minutes. The resulting supernatant was centrifuged twice at 7,000 g for 15 minutes to yield a washed mitochondrial pellet that was gently resuspended in 150 µL of isolation buffer. Protein concentration was determined by the Bradford method (Sigma, kit #B6916) using BSA as standard. Mitochondria were kept on ice at a final concentration of 40-50 mg/mL for less than 5 hours.

Mitochondrial Respiration

Oxygen consumption rates of heart mitochondria (0.1 mg/mL), incubated in the absence or presence of AOL at increasing doses (from 0 to 80 µM final concentration), were recorded polarographically under constant stirring at 25° C. using a high-resolution oximeter (Oxygraph-2K, Oroboros Instruments, Austria). The respiration medium consisted in 140 mM sucrose, 100 mM KCl, 1 mM EGTA, 20 mM $MgCl_2$, 10 mM $KH_2PO_4$, and 1 g/L (w/v) BSA essentially fatty acid free (pH 7.2).

Mitochondrial $ROS/H_2O_2$ Production

Rates of $ROS/H_2O_2$ production from heart mitochondria were assessed through the oxidation of the colorless, non-fluorescent indicator Amplex Red in the presence of exogenous horseradish peroxidase (HRP, EC 1.11.1.7, Sigma). $H_2O_2$ reacts with Amplex Red in a 1:1 stoichiometry, yielding the fluorescent compound resorufin (excitation: 560 nm; emission: 585 nm) which is stable once formed. Fluorescence was measured continuously with a spectro-fluorometer equipped with temperature control and stirring (SAFAS Xenius, Monaco). Isolated mitochondria (0.1 mg/mL) were incubated in the same experimental buffer than previously, supplemented with 15 µM Amplex Red and 10 µg/mL HRP. Glutamate (5 mM)/malate (2.5 mM) together with succinate (5 mM) were used as complex I and complex II substrates, respectively. Experiments were conducted under non-phosphorylating conditions in the presence of 15 µM atractyloside, i.e., under state IV conditions where mitochondrial membrane is maximal. Afterwards, rotenone (1.5 µM), antimycin A (2 µM), and myxothiazol (0.2 µM) were sequentially added to inhibit the redox centers within the electron transfer chain (FIG. 2), namely sites $I_Q$, $I_F$ (with rotenone), $III_{Qi}$ (with antimycin A) and $III_{Qo}$ (with myxothiazol). Assay was finally calibrated with known amounts of $H_2O_2$ (steps of 300 nM), in the presence of all relevant compounds, including AOL. The control test of the absence of effect of AOL on the Amplex Red assay itself and NAD(P)H oxidase $ROS/H_2O_2$ production was carried out in the absence of cardiac mitochondria and the presence of NAD (P)H oxidase (EC 1.6.3.3, 5 mU/mL, Sigma) and NADH (100 µM) solutions.

Results

We first verified (FIG. 1) that the AOL compound did not affect oxidative phosphorylation directly on isolated mitochondria from rat heart. This has been carried out by using the now classical oxygraph method. Mitochondria were first incubated with various AOL concentrations (5 to 80 µM) then respiratory substrate was added (substrate state, black curve), followed by a saturating ADP concentration to get the maximal oxidative phosphorylation rate (grey curve), and finally the addition of atractyloside (ATR) which inhibits the ADP/ATP translocator and gives the mitochondrial leak rate under non-phosphorylating conditions (FIG. 1A). The other panels of FIG. 1B-D presents the results obtained with different respiratory substrate combinations: glutamate+malate which feed electrons to complex I, succinate (+ rotenone) for complex II and glutamate+malate+succinate to feed electrons to both complexes. This last substrate combination has been chosen since it most closely resembles to in vivo conditions where Krebs cycle functions and both succinate and NADH are oxidized by respiratory chain. The results indicate that statistically no differences were observed in the presence of AOL for the large range of concentrations tested (FIG. 1), demonstrating under these conditions the absence of effect of AOL on mitochondrial oxidative phosphorylation—i.e., both on respiratory chain activity and ATP synthesis—as well as on mitochondrial inner membrane integrity (leak rate, after ATR addition). This last result indicates that AOL does not affect oxidative phosphorylation yield. Together, all these results confirm the absence of any harmful effect of AOL, documented by the use of this drug for human health for a long time.

Example 2: AOL Inhibits Superoxide/$H_2O_2$ Production by Mitochondria

As previously stated, mitochondrial ROS production is highly dependent on mitochondrial activity and conditions. Although we tested the effects of AOL on ROS production by mitochondria under numerous conditions, we chose to present here, for the sake of clarity, only the most demonstrative results of the very specific effects of AOL. As already discussed, the presence of the substrate combination (i.e., glutamate, malate and succinate) (FIG. 2A) giving the electrons to the whole respiratory chain, is the most representative of in situ conditions in the cell where the metabolism is active. Furthermore, maximal mitochondrial ROS/$H_2O_2$ production does not occur under conditions of high mitochondrial phosphorylation but under conditions of high reduction of electron transporters, i.e., low or no phosphorylation. These conditions are fulfilled in the presence of ATR (inhibition of ATP/ADP translocator by ATR, (FIG. 1) and we could effectively verify that the addition of ATR under conditions of saturating ADP triggered the production of ROS which was at the detection limit under maximal phosphorylating conditions (results not shown). Under these conditions, ROS are produced at different sites of the respiratory chain (Orr et al., 2013. Free Radic. Biol. Med. 65:1047-1059; Quinlan et al., 2013. Redox Biol. 1:304-312) (FIG. 2). The main sites of production are located at complexes I and III, where large changes in potential energy of electrons occur (Balaban et al., 2005. Cell. 120(4):483-495; Goncalves et al., 2015. J. Biol. Chem. 290(1):209-27), which also allow proton pumping at these sites.

Figure 2E:
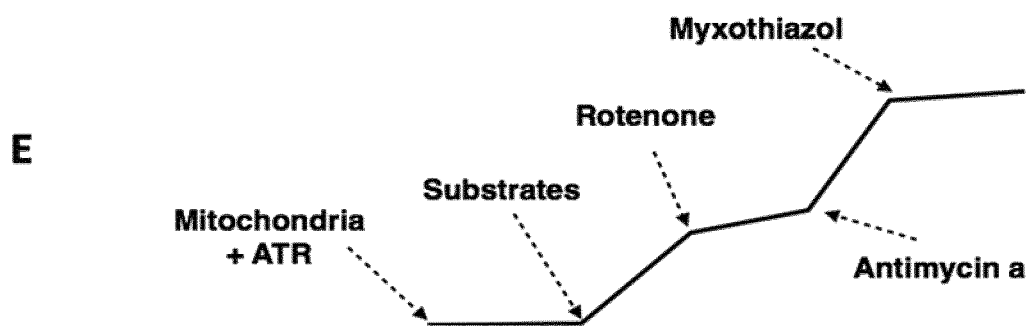
FIG. 2 presents the main sites of oxygen radicals' production by isolated mitochondria in the presence of substrates of both complexes I and III in the presence of ATR (state 4) in order to obtain maximal mitochondrial ROS production. As previously stated, mitochondrial ROS production is highly dependent on mitochondrial activity and conditions. Although AOL has been tested under numerous conditions, for the sake of clarity, we chose to present here only the most demonstrative results. The presence of all the substrates (i.e., glutamate, malate and succinate), giving the electrons to the whole chain, is the closest to in situ conditions in the cell. Under these conditions of substrates, we evaluated the effect of the presence of AOL on ROS production by the complete chain under ATR (inhibition of phosphorylation: maximum production), and by the complex I (inhibited by rotenone) and complex II (inhibited by Antimycin A). Colors refer to FIG. 3.

We designed a series of inhibitor titrations in order to decipher the action of AOL on ROS production by the whole respiratory chain under conditions of maximal ROS production (FIG. 2E). In the absence of specific inhibitors of the complexes, ROS production is at maximum and mainly comes from reverse electron transport at site $I_Q$ (FIG. 2A). It is crucial to note that ROS produced by complex I, either by site $I_Q$ (quinone site) or site $I_f$ (flavin site), are delivered to the inner—matrix—side of the inner mitochondrial membrane. After addition of rotenone, a classical inhibitor of complex I which specifically binds to $I_Q$, the ROS production decreases strongly and occurs almost entirely at site $III_{QO}$ and a remaining production at site $I_f$ due to the presence of complex I substrates and NADH production which are not inhibited by rotenone (FIG. 2B). The subsequent addition of antimycin A, an inhibitor of the electron transfer to cytochrome c, causes an increase in the reduced over oxidized quinone ratio, which is still reduced by complex II activity, and therefore a concomitant increase in ROS production at site $III_{QO}$ (FIG. 1C). Finally, the addition of myxothiazol, an inhibitor of complex III site $III_{QO}$, abolishes complex III ROS production and the remaining very low production may be ascribed to the flavin site of complex I, for which we have no known inhibitor (Goncalves et al., 2015. *J. Biol. Chem.* 290(1):209-27).

Figure 3:
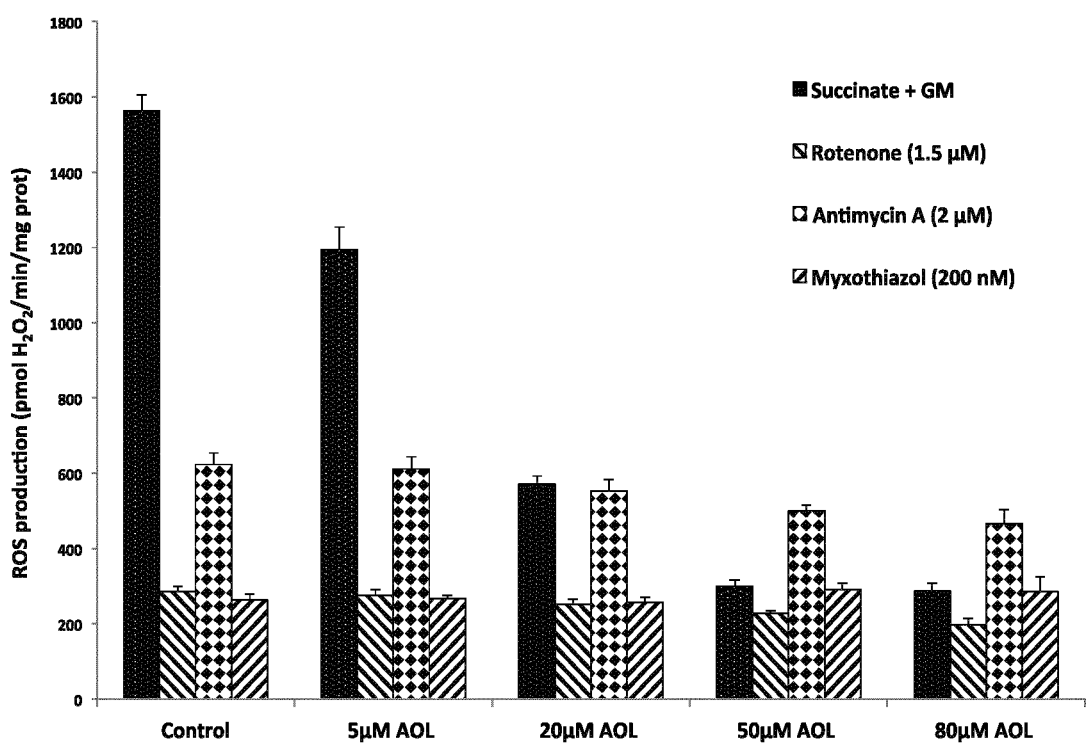
FIG. 3 presents the effect of AOL (5 to 80 μM) on $ROS/H_2O_2$ production by isolated mitochondria in the presence of substrates of complexes I and II in the presence of ATR (state 4), effect of rotenone, antimycin A and myxothiazol. In the absence of specific inhibitors of the complexes, ROS production is at maximum and mainly comes from reverse electron transport at site $I_Q$ (see FIG. 4). After addition of rotenone, which specifically reverse electron transport by inhibiting $I_Q$, production decreases and occurs almost entirely at site $III_{QO}$. The subsequent addition of Antimycin A, which blocks the transfer of the electrons to oxygen, increases ROS production at site $III_{QO}$ and finally myxothiazol blocks ROS production at site $III_{QO}$ (see FIG. 2 for details).

FIG. 3 illustrates the effect of the presence of increasing concentrations of AOL (from 5 to 80 μM) on $ROS/H_2O_2$ production measured under the different conditions defined in FIG. 2. It clearly appears from the results presented in this figure that AOL only affects the ROS production measured in the absence of inhibitor, by approximately 80%, while no statistical differences were observed with this range of AOL concentrations on $ROS/H_2O_2$ measured under the other conditions. As can be seen on FIG. 2, this specific condition (only ATR present) is the only condition in our assay where ROS are produced by complex I (site $I_Q$). When rotenone is added to the assay, $ROS/H_2O_2$ production appears insensitive to AOL, even at high concentrations, whatever the site being involved. The clear absence of effect on several sites of mitochondrial ROS production is not only surprising but also asks interesting questions about the very mechanism of action of AOL on mitochondria. Indeed, these results rule out the basic hypothesis of the mode of action of AOL described in the previous papers and at the basis of the patent for its therapeutic use. These results effectively demonstrate that AOL is not a radical scavenger; otherwise its action would be independent of the origin of the ROS. However, since AOL clearly strongly decreases ROS production by complex I at site $I_Q$, and only that site, we have the evidence that AOL specifically inhibits the formation of ROS at this site.

Although the mechanism has still to be investigated, evidence is presented here that AOL compound specifically interferes with mitochondrial complex I and selectively inhibits superoxide production from the ubiquinone-binding site of complex I (site $I_Q$) with no effects on superoxide production from other sites or on oxidative phosphorylation. To our knowledge, there is only one compound with comparable properties that has recently been described, the N-cyclohexyl-4-(4-nitrophenoxy) benzenesulfonamide (Orr et al., 2013. *Free Radic. Biol. Med.* 65:1047-1059). Like AOL, this compound does not modify the activity of complex I as a component of the respiratory chain and oxidative phosphorylation.

Figure 4:
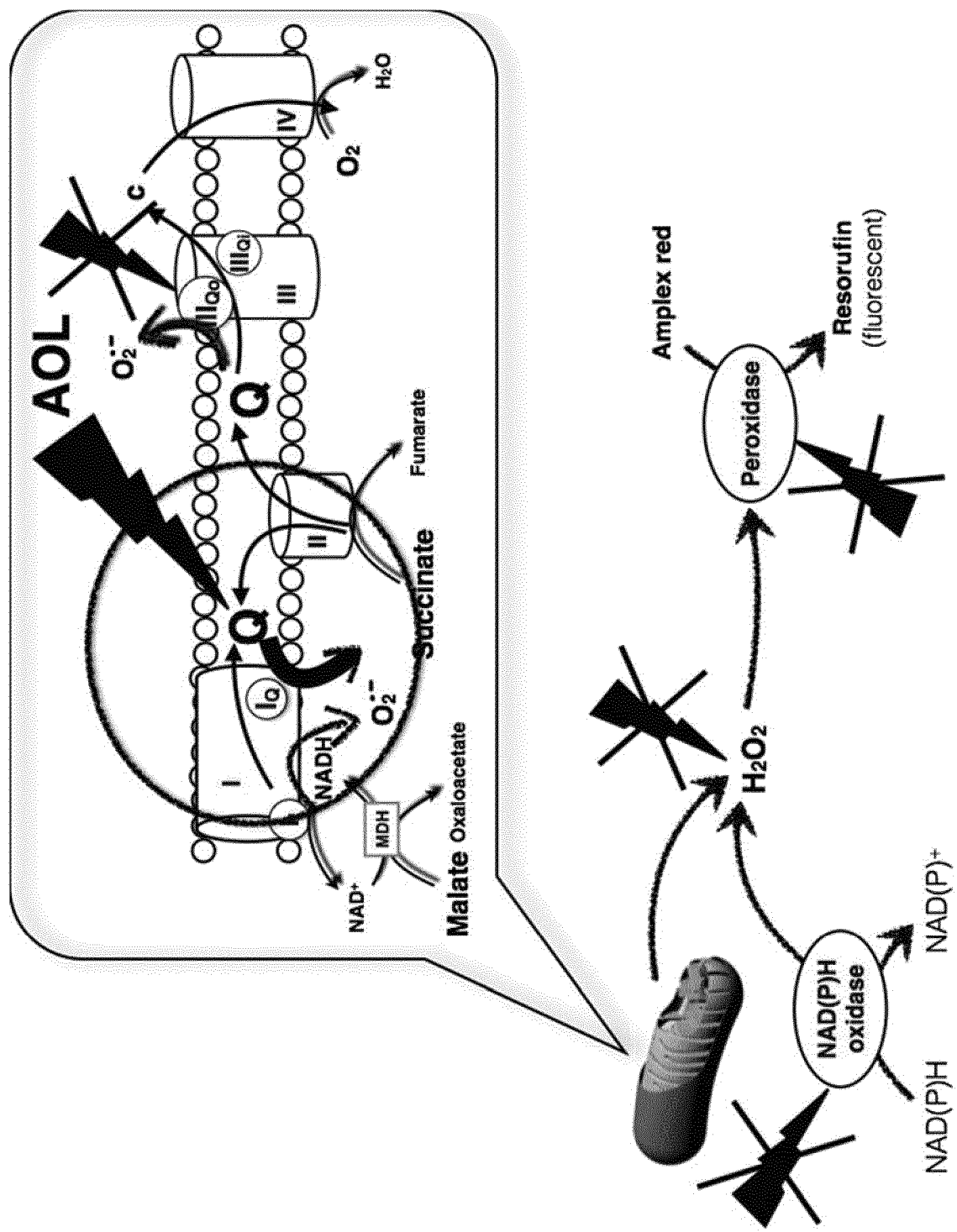
FIG. 4 is a scheme presenting the site of action of AOL on mitochondria ROS production and the sites where AOL has no or little action.

The specificity of AOL was further tested in vitro using the peroxidase-Amplex Red system utilized for the measurement of $ROS/H_2O_2$ by mitochondria, which in fact measures the appearance of $H_2O_2$ by the oxidation of Amplex Red to the fluorescent resorufin (see FIG. 4). In the absence of mitochondria and by adding instead a $H_2O_2$-producing system to the measuring system, it was possible to test the effect of AOL on this system. This has been carried out by using commercial NAD(P)H oxidase which produces $H_2O_2$ in the presence of added NAD(P)H and measuring the reduction of Amplex Red to resorufin (FIG. 4). We did not observe any inhibition of the fluorescence under these conditions, which exclude any effect of AOL on the NAD(P)H oxidase or on the peroxidase activity (results not shown). These results confirm that AOL does not interfere either with the measurement system or directly interact with $H_2O_2$. Interestingly, these results also demonstrate that AOL does not inhibit the $ROS/H_2O_2$ production by the NADP(H) oxidase, which is one—if not the—major non-mitochondrial $ROS/H_2O_2$ producer in the cells. The scheme on FIG. 4 recapitulates the different information on the mode of action of AOL on $ROS/H_2O_2$ production by mitochondria and NAD(P)H oxidase and stresses the very high specificity demonstrated here. These results are in striking contrast with previous assertions on the putative effect of AOL as radical scavenger.

When tested on isolated mitochondria from rat heart, AOL effectively decreases mitochondrial $ROS/H_2O_2$ production (in isolated mitochondria, $H_2O_2$ is produced from the reduction of ROS by mitochondrial superoxide dismutase). However, the results presented here clearly demonstrate that AOL does not act as a simple antioxidant or radical scavenger. While antioxidants are general $ROS/H_2O_2$ scavengers, AOL presents a complete selectivity towards the formation of ROS by site $I_Q$ in complex I, which demonstrates that AOL does not simply interact with superoxide radicals but specifically prevents their formation in complex I. In that respect, AOL therefore appears as a member of a brand-new class of oxidative stress protectants, whose only one member has been described very recently (Orr et al., 2013. *Free Radic. Biol. Med.* 65:1047-1059). Whereas antioxidants generally do not interfere directly with electron transport and scavenge ROS and/or $H_2O_2$ downstream from production and therefore can never fully suppress the effect of ROS (Orr et al., 2013. *Free Radic. Biol. Med.* 65:1047-1059), AOL may act differently by preventing ROS formation and thus being more active to protect mitochondria from their own ROS.

Data presented here go further and demonstrate that AOL is a specific inhibitor of ROS formation at site $I_Q$ of complex I of mitochondrial respiratory chain. Further experiments are however required to ascertain that AOL has completely no effect on other mitochondrial sites, but this does not preclude the above conclusions. We also show here some evidences that AOL may only interact with mitochondria without affecting oxygen radicals' formation in cytosol, and therefore would not affect intracellular signalisation.

Inhibition of complex I activity by rotenone or the neurotoxin MPP+ has been linked to parkinsonism in both rodents and humans, suggesting a link between dysfunctional complex I, ROS production, and neurodegeneration (Langston et al., 1983. *Science.* 219(4587):979-980; Betarbet et al., 2000. *Nat. Neurosci.* 3(12):1301-1306). In contrast, comparative analyses show an inverse relationship between maximal superoxide/$H_2O_2$ production from site $I_Q$, but not site $I_F$, and maximum life span across diverse vertebrate species (Lambert et al., 2007. *Aging Cell.* 6(5):607-618; Lambert et al., 2010. *Aging Cell.* 9(1):78-91). Therefore, selective modulators of superoxide/1202 production from site $I_Q$ or site $I_F$ would offer unique opportunities to probe the putative role of mitochondrial ROS production in normal and pathological processes (Orr et al., 2013. *Free Radic. Biol. Med.* 65:1047-1059). There are also some speculations, even controversial, that site $III_Q$—not affected by AOL—play an important role in cellular signalling during hypoxia.

In conclusion, it appears that AOL properties may represent a breakthrough in the search for specific modulators of ROS/$H_2O_2$ production in cells. This is a current important issue in research, and AOL has an enormous advantage toward newly discovered molecules since it is already authorized for human use.

AOL acts upstream from ROS production, therefore insuring higher protection than classical antioxidants;

AOL acts specifically on mitochondrial ROS production;

AOL ensures mitochondrial protection, crucial for numerous diseases, especially cardiac ones;

AOL does not interfere with cell signalisation;

AOL acts specifically on site $I_Q$ in complex I, which is the main mitochondrial site and may be implicated in important diseases, including Parkinson's disease and cardiac fibrillation.

AOL may represent the first member of a new class of "protectants" that specifically prevent ROS production inside mitochondria, and may therefore be used for mitochondrial protection during various oxidative stress and therefore prevent diseases, with very little side effects on crucial cellular ROS signalling.

Example 3: Effect of AOL in a Cardiovascular Disease: Diabetes

Effect of the Compound AOL on Glucose-Stimulated Insulin Secretion (GSIS) in Mouse Pancreatic Islets The aim of the study was to investigate the ability of the compound AOL in modulating glucose-stimulated insulin secretion (GSIS) in isolated pancreatic islets from mice.

Material and Methods

Experiments were conducted in strict compliance with the European Union recommendations (2010/63/EU) and were approved by the French Ministry of Agriculture and Fisheries (authorization no 3309004) and the local ethical committee of the University of Bordeaux. Maximal efforts were made to reduce the suffering and the number of animals used.

Three independent experiments were carried out and, for each of them, two mice were sacrificed and islets isolated according to the procedure further described below.

Pancreatic islets were isolated using the collagenase digestion method. Briefly, pancreas was inflated with Hanks solution containing 0.33 mg/mL of collagenase (Sigma-Aldrich), 5.6 mM glucose and 1% bovine serum albumin, pH 7.35, removed and kept at 37° C. for 6-9 minutes. After tissue digestion and exocrine removal by three consecutive washes, the islets were manually collected, under a binocular magnifier. Islets were left recovering from digestion by culturing for 20-24 hours in RPMI-1640 medium containing 11 mM glucose (Invitrogen, CA, USA) and supplemented with 2 mM glutamine, 200 IU/mL penicillin, 200 μg/mL streptomycin and 8% fetal bovine serum stripped with charcoal-dextran (Invitrogen).

For each static GSIS experiment, islets from two mice were first incubated for 2 hours at 37° C. in 3 mL Krebs-bicarbonate buffer solution (in mM): 14 NaCl, 0.45 KCl, 0.25 $CaCl_2$, 0.1 $MgCl_2$, 2 HEPES and 3 glucose, equilibrated with a mixture of 95% 02:5% C02, pH 7.4. Then, groups of five size-matched islets were transferred to 24-well plate wells with 0.5 mL fresh buffer containing either one of the following stimulus: 3 mM glucose (Glc) and 11 mM glucose plus vehicle (0.4% DMSO in Krebs-bicarbonate buffer), or 11 mM glucose plus the diluted drug to be tested (10 μM or 20 μM of AOL in vehicle), and further incubated for 1 hour. Six different wells were used for each experimental condition. At the end of the incubation, bovine albumin was added to each well to a final concentration of 1%, and the plate was put at 4° C. for 15 minutes to stop insulin secretion. Next, the media was collected and stored at −20° C. for subsequent measurement of insulin content by ELISA (kit from Mercodia, Uppsala, Sweden), according to the manufacturer's instructions. Insulin secretion in each well was calculated as ng of insulin per islet and per hour of incubation, and then expressed as percentage of insulin secretion in 11 mM glucose vehicle group, which was considered 100%.

Description of the experimental groups is shown in Table 1.

TABLE 1

| Group abbreviation | 3 mM Glc-Veh | 11 mM Glc-Veh | 11 mM Glc + AOL 10 μM | 11 mM Glc + AOL 20 μM |
|---|---|---|---|---|
| Group definition | Group treated with vehicle and 3 mM glucose | Group treated with vehicle and 11 mM glucose | Group treated with AOL 10 μM and 11 mM glucose | Group treated with AOL 20 μM and 11 mM glucose |
| Number of wells | 4-6 | 5-6 | 4-6 | 6 |

Results

Figure 5:
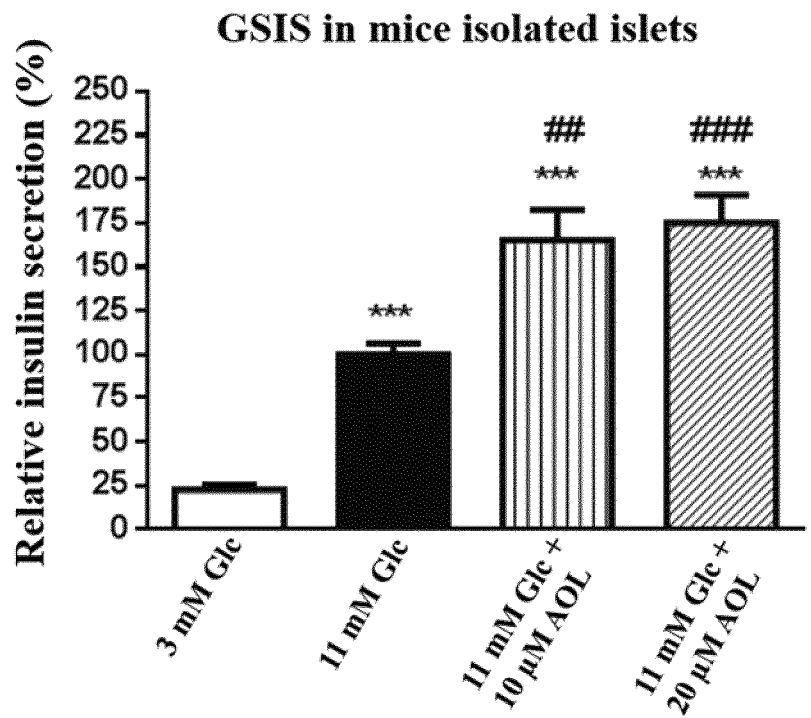
FIG. 5 is a histogram showing the effect of 10 and 20 μM AOL on glucose stimulated insulin secretion (GSIS) in isolated islets from male C57Bl/6J mice. Combination of three experiments is displayed. Islets from two mice for each experiment; five islets each well; four to six wells each condition. Insulin secretion data were normalized to 11 mM Glc-Veh group, which was considered 100%. *$p<0.05$, $p<0.01$ and *$p<0.001$ versus 3 mM Glc-Veh; #$p<0.05$, ##$p<0.01$ and ###$p<0.001$ versus 11 mM Glc-Veh; One-way ANOVA and Bonferroni's post-hoc test.

Individual insulin secretion values obtained in each of the three experiments were combined and averaged. These are expressed as the relative percentage of insulin secretion, normalized to the 11-mM glucose vehicle group (FIG. 5).

Combined analysis of data shows that AOL enhanced GSIS at both 10 and 20 μM, showing a similar potency, with a GSIS increase ranging around 65-75% as compared to the 11 mM glucose vehicle group (One-way ANOVA; Bonferroni's post-test). For statistical analysis see Table 2.

TABLE 2

| | One-way ANOVA | Sum of squares | Degrees of freedom | Mean of squares | F | p |
|---|---|---|---|---|---|---|
| Experiment #1 | Treatment | 50630 | 3 | 16880 | 18.36 | <0.0001 |
| | Residual | 16540 | 18 | 919.0 | | |
| Experiment #2 | Treatment | 44790 | 3 | 14930 | 21.46 | <0.0001 |
| | Residual | 12530 | 18 | 695.9 | | |
| Experiment #3 | Treatment | 193700 | 3 | 64570 | 35.16 | <0.0001 |
| | Residual | 33060 | 18 | 1837 | | |
| Combined experiments | Treatment | 244100 | 3 | 81360 | 33.13 | <0.0001 |
| | Residual | 152200 | 62 | 2455 | | |

Conclusion

The study demonstrates that AOL, at the doses tested (10 and 20 μM), enhances GSIS and significantly stimulates insulin secretion in vitro, in isolated pancreatic islets from mice.

Thus, these findings suggest that AOL might be particularly useful in pathological conditions in which insulin secretion is deficient, such as diabetes, including type 1 diabetes, type 2 diabetes and other types of diabetes such as MODY (Maturity Onset Diabetes of the Young).

Effects of a Chronic Treatment with AOL on Food Intake, Body Weight and Glucose Metabolism in Diet-Induced Obese Mice Material and Methods The aim of the study was to determine whether the compound AOL, administered daily at the doses of 5 mg/kg and 10 mg/kg for up to five weeks by intraperitoneal (i.p.)

daily administration in diet-induced obese (DIO) mice fed with a high-fat diet (HFD), modifies food intake, body weight, adiposity and glucose metabolism.

Mice were fed ad libitum with a HFD (60% of calories from fat, mostly lard) for twelve weeks before the pharmacological study begun. Animals received AOL or its vehicle by intraperitoneal (i.p.) administration and were maintained on HFD for the length of the study. Food intake and body weight were measured daily and recorded for up to three consecutive weeks.

For appropriate distribution of the mice in the different experimental groups before the start of the pharmacological study, we evaluated their body composition in vivo using an Echo MRI 900 (EchoMedical Systems, Houston, Tex., USA) (see also Cardinal et al., 2014. Mol. Metab. 3(7):705-16; Cardinal et al., 2015. Endocrinology. 156(2):411-8). Daily food intake and body weight measurements were obtained using a balance (model TP1502, Denver Instruments).

Thirty 7-weeks-old male C57/B16J mice arrived to the laboratory on 25 Feb. 2016 and underwent a first in vivo body composition analysis (Echo MRI 900, EchoMRI Systems) after 1 week of adaptation to the experimental housing room. After this first MRI analysis, animals were fed a high-fat diet (HFD) ad libitum for a period of twelve weeks. Thereafter, they underwent a second MRI analysis and were distributed into 3 experimental groups of equivalent body weight and body composition.

Once the pharmacological treatment started (day 1), food intake (FI) and body weight (BW) were measured daily before the dark phase in animals housed in their home cage. Spillage of food was checked daily. The food consumed was calculated by subtracting the food left in the hoppers from the initial pre-weighted amount. FI and BW were measured for three consecutive weeks. Afterwards animals underwent a third MRI analysis in order to observe potential effects of the treatment onto the body composition (changes in fat and lean mass), followed by a glucose tolerance test (GTT) and an insulin tolerance test (ITT). Mice received daily i.p. administration of AOL or its vehicle for a total length of five weeks, until they were sacrificed.

A nuclear echo magnetic resonance imaging whole-body composition analyzer (Echo MRI 900; EchoMedical Systems) was used to repeatedly assess body fat and lean mass in conscious mice.

GTT and ITT are routinely used to assess dynamic modulation of glucose metabolism respectively during a glucose challenge and an insulin challenge. They give information on the presence of glucose intolerance and possible resistance to the action of the hormone insulin.

Animals were injected i.p. with 1.5 g/kg of D-Glucose (Sigma-Aldrich) for the GTT or with 0.5 U/kg of insulin (Humulin, Lilly, France) for the ITT. For the GTT and the ITT, animals were fasted overnight. The tests were conducted the following morning. Blood samples were taken from the tail vein at different time points (0, 15, 30, 60, 90 and 120 minutes after the i.p. administration of glucose or insulin) and glucose concentration was measured using glucose sticks (OneTouch Vita, Lifescan France, Issy les Moulineaux, France).

At sacrifice, blood samples were collected, blood glucose was rapidly assessed using glucose sticks and blood samples were then centrifuged at 3000 rpm for 15 minutes. The obtained plasma was stored at −80° C. for subsequent measurement of insulin, which was carried out by performing an ELISA (kit from Mercodia, Uppsala, Sweden), according to the manufacturer's instructions.

HOMA-IR index, which gives information about the presence of insulin resistance, was calculated using the formula (Glucose mmol/L×Insulin mU/L)/22.5.

Statistical analyses were carried out using GraphPad Prism Software (San Diego, Calif., USA). Repeated measurements two-way ANOVA were carried out to analyze the effects of the treatment factor, the time factor and their interaction on food intake, body weight, GTT and ITT. One-way ANOVA was carried out to compare the effect of the treatment factor on cumulative food intake, body composition, AUC of GTT and ITT, and circulating glucose, insulin and HOMA-IR at time of sacrifice. When ANOVA results were significant (p<0.05), the Tukey post-hoc test was performed to allow adequate multiple comparisons among the groups. Data are expressed as mean±SEM. Graphs were generated using GraphPad Prism software.

Results

The treatment did not have a significant effect on body weight or on the percentage (%) of change of the body weight calculated from day 1 in which body weight was measured before the first administration of AOL.

Figure 6:
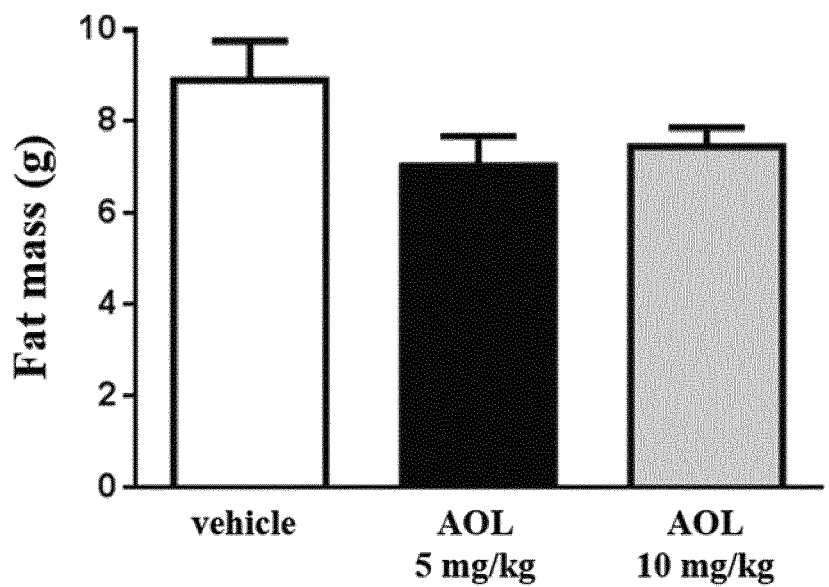
FIG. 6 is a histogram showing the fat mass determined after 3 weeks of treatment. Fat mass is expressed in grams (g). Data are expressed as mean±SEM.
Figure 7:
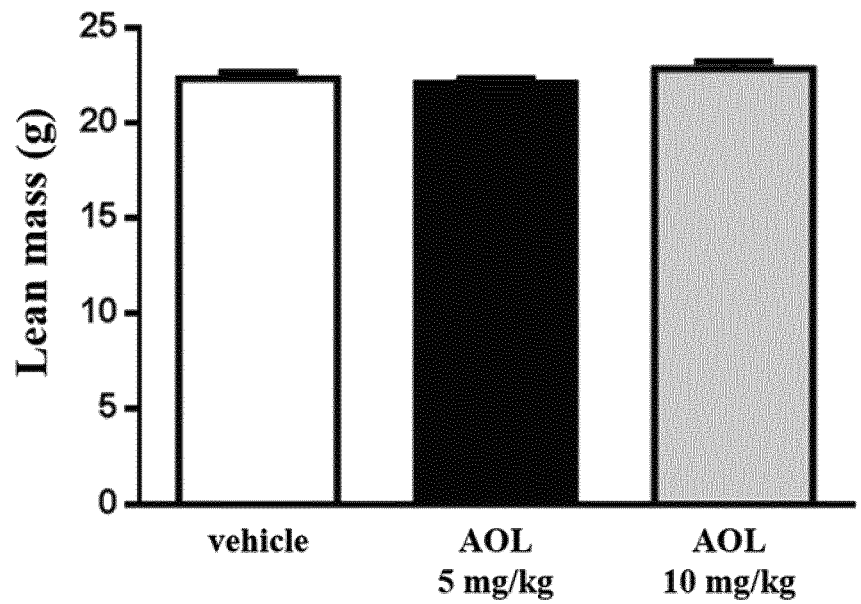
FIG. 7 is a histogram showing the lean mass determined after 3 weeks of treatment. Lean mass is expressed in grams (g). Data are expressed as mean±SEM.

Chronic administration of AOL after three weeks tended to reduce fat mass (p=0.13, FIG. 6), whilst it did not have any effect on lean mass (FIG. 7). The mean±SEM values are represented in FIG. 6 and FIG. 7 and statistical analysis are shown in Table 3 and Table 4, respectively.

TABLE 3

Statistical analysis of data represented in FIG. 6.

| One-way ANOVA | Sum of squares | Degrees of freedom | Mean of squares | F | p |
|---|---|---|---|---|---|
| Treatment | 18.50 | 2 | 9.248 | 2.151 | 0.1366 |
| Residual | 111.8 | 26 | 4.299 | | |

TABLE 4

Statistical analysis of data represented in FIG. 7.

| One-way ANOVA | Sum of squares | Degrees of freedom | Mean of squares | F | p |
|---|---|---|---|---|---|
| Treatment | 2.773 | 2 | 1.387 | 1.256 | 0.3014 |
| Residual | 28.70 | 26 | 1.104 | | |

AOL at the dose of 10 mg/kg significantly blunted the action of insulin on circulating glucose levels during an ITT (FIG. 8), suggesting the presence of insulin resistance. Accordingly, a treatment effect was also found when analyzing the AUC (AUC veh: 12812.50±750.35, AUC AOL 5 mg/kg: 15006.56±1139.69, AUC AOL 10 mg/kg: 18168.33±1562.90, one-way ANOVA F(2, 23)=5.186, p=0.0138), with the AOL 10 mg/kg group having an AUC significantly higher than the vehicle group (Tukey post-hoc, p=0.0107). The mean±SEM values are represented in FIG. 8 and statistical analysis are shown in Table 5.

TABLE 5

Figure 8:
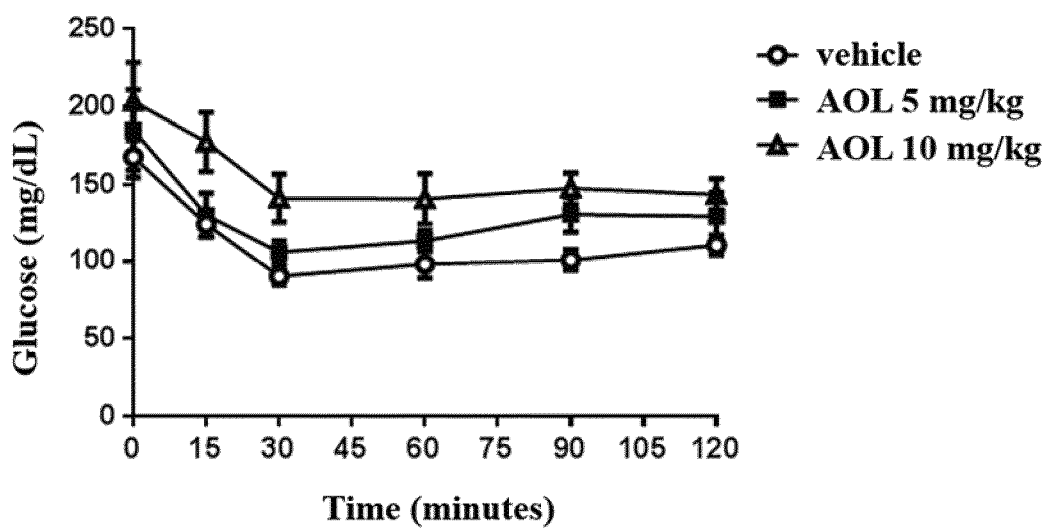
FIG. 8 is a graph showing the effect of chronic treatment with AOL (5 mg/kg and 10 mg/kg) on glucose responses during an insulin tolerance test (ITT). The graph represents changes in blood glucose levels during an ITT. Data are expressed as mean±SEM.

Post-hoc analysis on the treatment factor for data in FIG. 8. The numbers in the Tukey Post-hoc analysis table represent the p values. Values in bold correspond to significant (p < 0.05) results.

| Tukey post-hoc | Vehicle | AOL 5 mg/kg | AOL 10 mg/kg |
|---|---|---|---|
| Vehicle | | 0.532016 | 0.023546 |
| OP 5 mg/kg | 0.532016 | | 0.232976 |
| OP 10 mg/kg | 0.023546 | 0.232976 | |

At time of sacrifice, after five weeks of treatment, blood glucose levels were measured in 2-hour fasted mice.

AOL tended to decrease blood glucose levels (FIG. 9) and statistical analysis in Table 6.

TABLE 6

Figure 9:
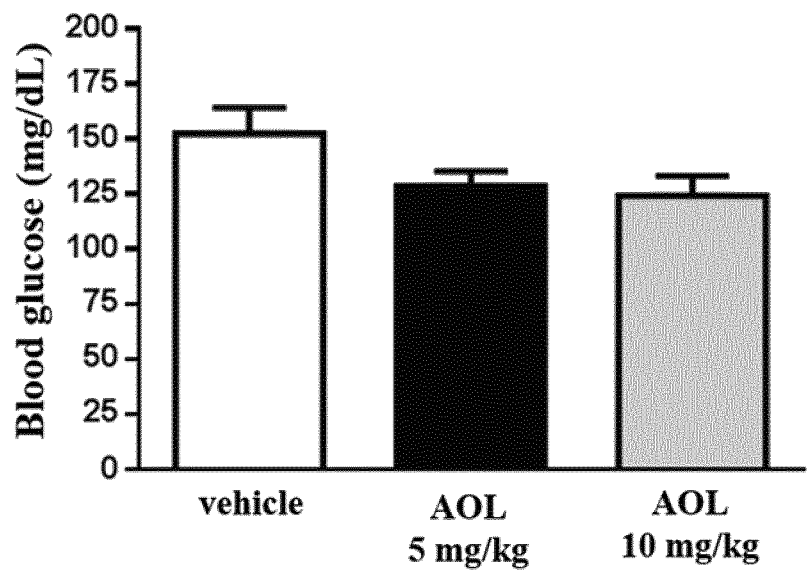
FIG. 9 is a histogram showing the effect of AOL on blood glucose levels. After five weeks of treatment, blood glucose was measured in 2-h fasted mice. Data are expressed as mean±SEM.

Statistical analysis of data represented in FIG. 9.

| One-way ANOVA | Sum of squares | Degrees of freedom | Mean of squares | F | p |
|---|---|---|---|---|---|
| Treatment | 3972 | 2 | 1986 | 2.586 | 0.0980 |
| Residual | 16898 | 22 | 768.1 | | |

Conclusion

In diet-induced obese animals, chronic daily administration of AOL tended to decrease body weight and food intake in DIO mice (data not shown). Accordingly, this was associated with a trend to decrease fat mass and basal blood glucose levels.

Overall, these data suggest that AOL might have some beneficial effects in a model of dietary obesity.

Example 4: Effect of AOL in a Neurologic Disease: Parkinson Disease

In this study, the potential neuroprotective effects of AOL were assessed by counting the number of tyrosine hydroxylase (TH)-positive neurons in the substantia nigra (SN) in the sub-chronic 1-methyl-4-phenyl-1,2,3,6-tetrahydropyridine (MPTP) mouse model of Parkinson's disease. Mice were treated with AOL (5 mg/kg; i.p.) or vehicle for 11 consecutive days. MPTP (20 mg/kg; i.p.) or saline was administered on treatment days 4-8. All mice were killed on day 12 following final administration of treatment.

Sub-chronic MPTP administration in C57/bl6 mice induces degeneration of nigrostriatal dopaminergic neurons, which leads to reduced number of TH-positive neurons in the SN which was, on this occasion, a reduction of 39%.

Material and Methods

For vehicle conditions, the test item was dissolved in 0.5% DMSO/0.95% Tween 20 in saline while AOL was administered intraperitoneally (i.p.) at the dose of 5 mg/kg. The volume of administration was 10 mL/kg.

C57bl/6 male mice (Janvier) weighing 22-28 g were housed in a temperature-controlled room under a 12-hour light/dark cycle with free access to food and water. In order to tentatively achieve final numbers of n=10 per group, n=12 per group were used to account for possible losses in the course of the experiment. To produce neurodegeneration of dopaminergic neurons in the substantia nigra, mice were treated with MPTP hydrochloride (20 mg/kg i.p. once daily for five consecutive days).

Mice were humanely euthanized by cervical dislocation after the last administration.

The caudal half of the brain (containing the substantia nigra) was placed in paraformaldehyde (4% in 0.1 M Phosphate Buffer Saline (PBS) pH 7.4) for 5 days and then transferred to 20% sucrose (20% in 0.1 M PBS) for cryoprotection. The tissue was then frozen in cold isopentane (at −50° C.±2° C.).

The striata were dissected out, weighed and snap frozen separately in dry ice (at −70° C.±10° C.). Tissues samples are stored at −70° C. (±10° C.) for an optional HPLC analysis of dopamine and its metabolites. If this option is not taken, the striata will be destroyed.

Coronal serial sections of the entire mesencephalon were cut on a cryostat at 50 μm intervals. Sections were collected free-floating in well-plates containing cryoprotectant solution, which were then stored at −20° C. until the day of TH immunohistochemical processing.

TH immunohistochemistry was performed as follows on every fourth section. Tissue sections were taken from the −20° C. freezer, left to adjust to room temperature, and then rinsed in PBS solution. Endogenous peroxidase was inhibited by incubating in PBS containing 0.3% $H_2O_2$ for 10 minutes. Following this, sections were washed in PBS, incubated in PBS 4% normal horse serum (NHS) and 0.3% Triton X-100 for 30 minutes, for the blockade of non-specific antigenic sites. Sections were then incubated overnight at room temperature in antibody dilutant+primary antibody for tyrosine hydroxylase (TH) (anti-TH affinity isolated antibody, Sigma T8700) at a dilution of 1/10,000. Sections were then rinsed thoroughly in PBS and incubated for 30 minutes in ImmPRESS Ig peroxidase polymer detection reagent (Vector MP7401). Following this, sections were thoroughly washed with PBS. Immunological staining was then revealed with 3,3'-Diaminobenzidine (DAB)/Tris/$H_2O_2$ kit (Vector SK4100). After one minute, revelation was stopped with several PBS washes. Sections were mounted and counterstained with 0.1% cresyl violet.

Unbiased stereological analysis was used to estimate the number of TH-immunopositive (TH+) neurons (Mercator, Explora Nova, La Rochelle, France). The boundaries of the SN were determined by examining the size and shape of the different TH+ neuronal groups. The volume was calculated by using the formula: $V=\Sigma S$ td; where $\Sigma S$ is the sum of surface areas, t is the average section thickness and d is the number of slices between two consecutive sections measured. One in every 4 sections was used; optical dissectors were distributed using a systematic sampling scheme. Dissectors (50 μm length, 40 μm width) were separated from each other by 150 μm (x) and 120 μm (y). The following formula was used to estimate the number of TH+ neurons: $N=V(SN) (\Sigma Q-/\Sigma V(dis))$; where N is the estimation of cell number, V is the volume of the SN, $\Sigma Q-$ is the number of cells counted in the dissectors, and $\Sigma V(dis)$ is the total volume of all the dissectors. Mean estimated number of neurons and SEM was then calculated for each group.

All statistical analyses were performed using Graphpad prism version 7. All data are presented as mean±the standard error of the mean (SEM). The effect of AOL was analyzed with a one-way ANOVA followed by Dunnett's multiple comparisons post-hoc analysis. A P value of less than 0.05 was considered significant.

Results

Figure 10:
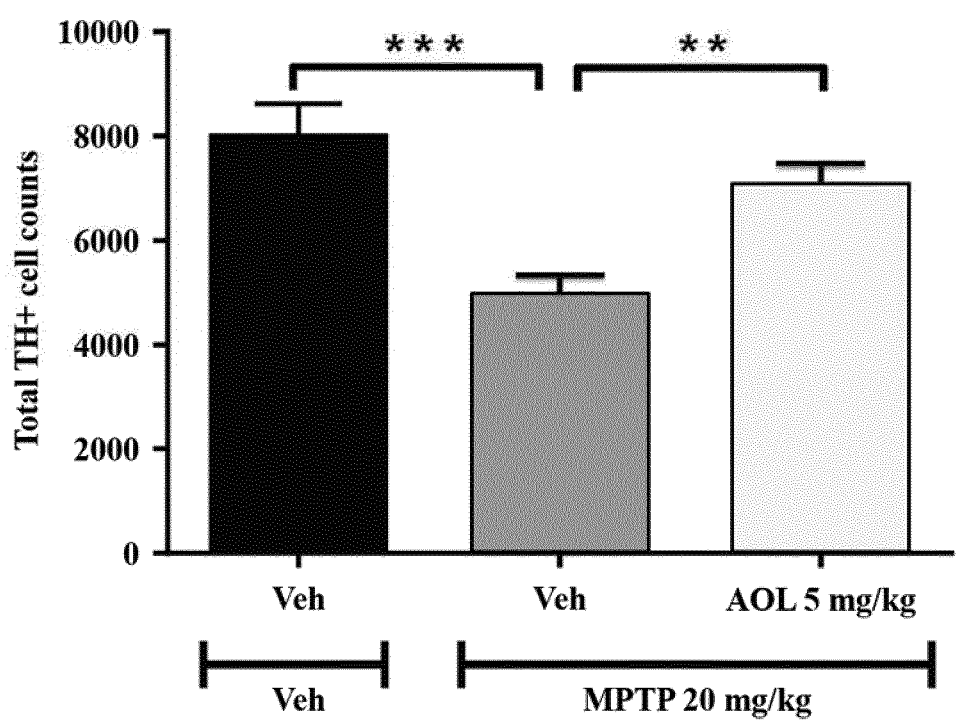
FIG. 10 is a histogram showing the neuroprotective effect of AOL (5 mg/kg bid for 11 days) on TH-positive cell counts in the SN in MPTP-treated mice. Data expressed as mean±SEM (n=10-11) and analyzed using one-way repeated measures ANOVA followed by Dunnett's multiple comparison test. $P<0.01$; *$P<0.001$ c.f. MPTP+vehicle.

There was a significant effect of treatment on the number of TH+ cells in the SN (F2,29=10.94, p<0.001, FIG. 10). The number of TH+ cells in the SN was reduced by 39% (p<0.001) in MPTP-treated compared to vehicle-treated animals. Following administration of AOL, the number of TH+ cells in the SN was increased by 44% (p<0.01) compared to vehicle in the MPTP-treated mice.

Conclusion

AOL treatment for 11 consecutive days, at a dose of 5 mg/kg, has a significant neuroprotective effect compared to vehicle, in preventing the MPTP-induced reduction in TH+ cells in the SN, resulting in 44% more cells surviving in the SN with the administration of AOL.

These data suggest that AOL treatment can protect the dopaminergic neurons in the substantia nigra from MPTP intoxication.

Example 5: Effect of AOL in Cardiovascular Disease: Ischemia-Reperfusion Injury The present study aims at evaluating the capacity for AOL to protect perfused rat heart from the damages occurring after global ischemia and reperfusion.

The consequences of 30 minutes' global ischemia followed by 120 minutes' reperfusion (FIG. 11) on contractility and tissue viability were studied on isolated perfused rat heart pretreated or not (control vehicle) with 10 µM AOL.

Material and Methods

All procedures conformed to the UK Animals (Scientific Procedures) Act 1986 and the Guide for the Care and Use of Laboratory Animals published by the National Institutes of Health (NIH Publication No. 85-23. revised 1996). Male Wistar rats (250-300 g) were anesthetized by 3% isoflurane, heparinized and euthanized by a lethal IP injection of pentobarbital (130 mg/kg). Hearts (~0.95 g of fresh weight) were rapidly harvested and placed into ice cold Krebs-Henseleit buffer containing (in mmol/L): NaCl 118, $NaHCO_3$ 25, KCl 4.8, $KH_2PO_4$ 1.2, $MgSO_4$ 1.2, glucose 11 and $CaCl_2$ 1.8; gassed with 95% $O_2$/5% $CO_2$ at 37° C. (pH 7.4). Langendorff heart perfusions were performed (Garlid et al., 2006. *Am. J. Physiol. Heart Circ. Physiol.* 291(1): H152-60) and contractility was assessed by continuous measurement of the rate pressure product (RPP) thanks to a balloon placed in the left ventricle and connected to a pressure transducer. Hearts were perfused in a constant flow mode (12 mL/min). After 10 minutes for stabilization followed by 10 minutes of treatment with the vehicle (Control) or 10 µM AOL solution, global normothermic ischemia was induced by halting perfusion flow for 30 minutes while immersing the heart in perfusion buffer at 37° C. At the end of the reperfusion period, hearts were stained to assess infarct size, or freeze-clamped using liquid-nitrogen cooled tongues. In the latter case, hearts were grinded under liquid nitrogen, and stored at −80° C. for further analyses.

At the end of the reperfusion period, hearts were stained with triphenyltetrazolium chloride (TTC): hearts were perfused for 7 minutes at 13 mL/min with a 12% (w/v) TTC solution in order to get a 1% final concentration in the heart. Hearts were then detached from the cannula and incubated for an additional 4 minutes at 37° C. before being sliced perpendicular to the longitudinal axis into 6 slices. The slices were then treated in 4% (w/v) formalin solution overnight at 4° C. and weighed, before both sides of each slice were photographed. The surface of the necrotic and at-risk areas of each side were determined on each photography by planimetry (AlphaEase v5.5), and infarct size was expressed as a percentage of the total cross-sectional area of the heart, since total heart was subjected to ischemia.

Data from 6 independent preparations are expressed as means±SEM. The n number in each group being smaller than 20, the distribution was considered as non-normal and consequently a non-parametric Mann-Whitney test (SPSS statistics 17.0) was performed to compare the two groups. Results were considered statistically significant if the p-value was below 0.05.

Results

Figure 11:
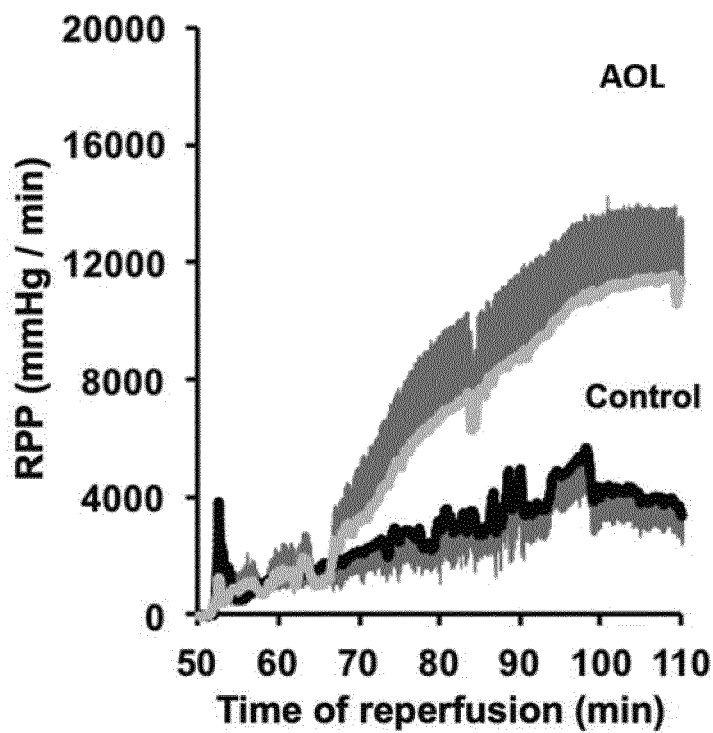
FIG. 11 is a graph showing the effect of AOL on the recovery of heart contractility during the reperfusion phase following ischemia. Data are expressed as mean±SEM for control (black) and AOL treated (grey) for 6 independent experiments.
Figure 12:
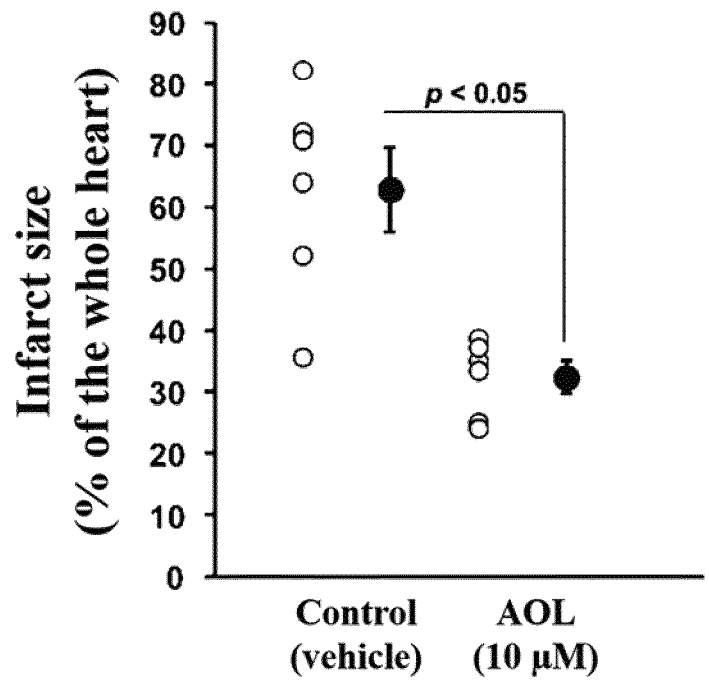
FIG. 12 is a graph showing the effect of AOL on the infarct size of the slices of ischemic hearts. At the end of the reperfusion period, hearts were stained by triphenyltetrazolium chloride (TTC). Living tissue appears red, while damaged tissue appears white.

FIG. 11 presents the evolution of the RPP—considered here as a surrogate of heart contractility—during the critical phase of the reperfusion following ischemia. Clearly, AOL improves the contractility and after an identical evolution as compared to the control hearts treated with AOL, showed an improvement of contractility which was about three times higher than control hearts after 2 hours of reperfusion. At this time, hearts were prepared for TTC staining to assess tissue viability. The higher contractile activity for AOL hearts was confirmed by TTC staining, and photographs of the slices of treated and non-treated hearts (data not shown) clearly show that AOL induced an important protection of cardiac tissue. This protection has been analyzed more thoroughly and the results are presented in FIG. 12. The infarct size—damaged tissue—is expressed as percentage of the total surface for each independent experiment together with the mean value for AOL-treated and non-treated hearts. Results clearly show that AOL highly significantly protects cardiac tissue from ischemia/reperfusion damages. In fact, about 50% of infarcted tissue was rescued by pre-treatment with AOL (FIG. 12).

Conclusion

These results extend, under ex vivo (living organ) conditions, the role of AOL as an inhibitor of mitochondrial ROS production, most probably at the level of complex I.

They also evidence the therapeutic interest of AOL for tissue protection against ischemia/reperfusion damages, not only in heart but also in any tissue subjected to ischemia.

Example 6: Effect of AOL in a Cardiovascular Disease: Pulmonary Hypertension The present study aims at studying the role of mitochondria in the pulmonary vasculature physiology and providing a new alternative treatment of pulmonary hypertension. This disease is characterized by increased pulmonary arterial pressure and remodeling of pulmonary arteries (PA), leading to increased pulmonary vascular resistance, hypertrophy of the right ventricle, right heart failure and ultimately, death.

Pulmonary hypertension can be divided into five groups, among which the group 1 corresponds to pulmonary arterial hypertension. As for group 3, it includes pulmonary hypertension due to lung diseases (such as chronic obstructive pulmonary disorder) and/or alveolar hypoxemia.

To address the issue of the effect of AOL, two different rat models were used: a hypoxia model and a monocrotaline-induced model, that share pathophysiological characteristics with group 3 and group 1 pulmonary hypertension, respectively.

Material and Methods

Male Wistar rats (300-400 g) were separated into 3 groups and used 4 weeks later:
- the first group (control or normoxic rats—N rats) was housed in ambient room air;
- the second group (chronic hypoxic rats—CH rats) was exposed to chronic hypoxia for 3 weeks in a hypobaric chamber (50 kPa); and
- the third group (MCT rats) was injected with a single intraperitoneal dose of monocrotaline at a dose of 60 mg/kg. MCT (Sigma, St Quentin Fallavier, France) was dissolved in an equal volume of HCl (1 M) and NaOH (1 M).

In each group, some animals were treated with AOL (Sulfarlem, EG Labo Eurogenerics. Crushed tablets mixed with food, fed ad libitum) and some other animals were untreated. Eaten food was weighed every day to estimate the AOL dose administered. 10 mg/kg/day was thus administered during the 3 weeks of experiment for the second and third groups.

For each condition, 7 to 10 rats were used. All animal care and experimental procedures complied with the recommendations of the Federation of European Laboratory Animals Science Association, and were approved by the local ethics committee (Comité d'éthique régional d'Aquitaine—referenced 50110016-A).

Pulmonary hypertension was assessed by measuring both the mean pulmonary arterial pressure (mPAP) and right ventricle hypertrophy. To measure PAP, N, CH and MCT rats were anesthetized with pentobarbital sodium (Centravet) by intraperitoneal injection (60 mg/kg) and mPAP was measured, in closed-chest rats, through a catheter inserted in the right jugular vein, then through the right atria and the right ventricle into the pulmonary artery, and attached to a Baxter Uniflow gauge pressure transducer. Right ventricle hypertrophy was estimated by the ratio of right ventricle (RV) to left ventricle plus septum (LV+S) weight (Fulton index).

Pulmonary arteries (PA) remodeling was assessed by measuring the percentage of the PA medial thickness from sections of paraffin-embedded lung. Lung sections were first stained with hematoxylin and eosin (VWR) according to common histological procedure. On each section, three groups of 10 intracinar arteries with different cross-sectional diameters were observed to evaluate medial wall thickness (namely cross-sectional diameters under 50 µm, between 50 to 100 µm and between 100 to 150 µm).

Results

Figure 13:
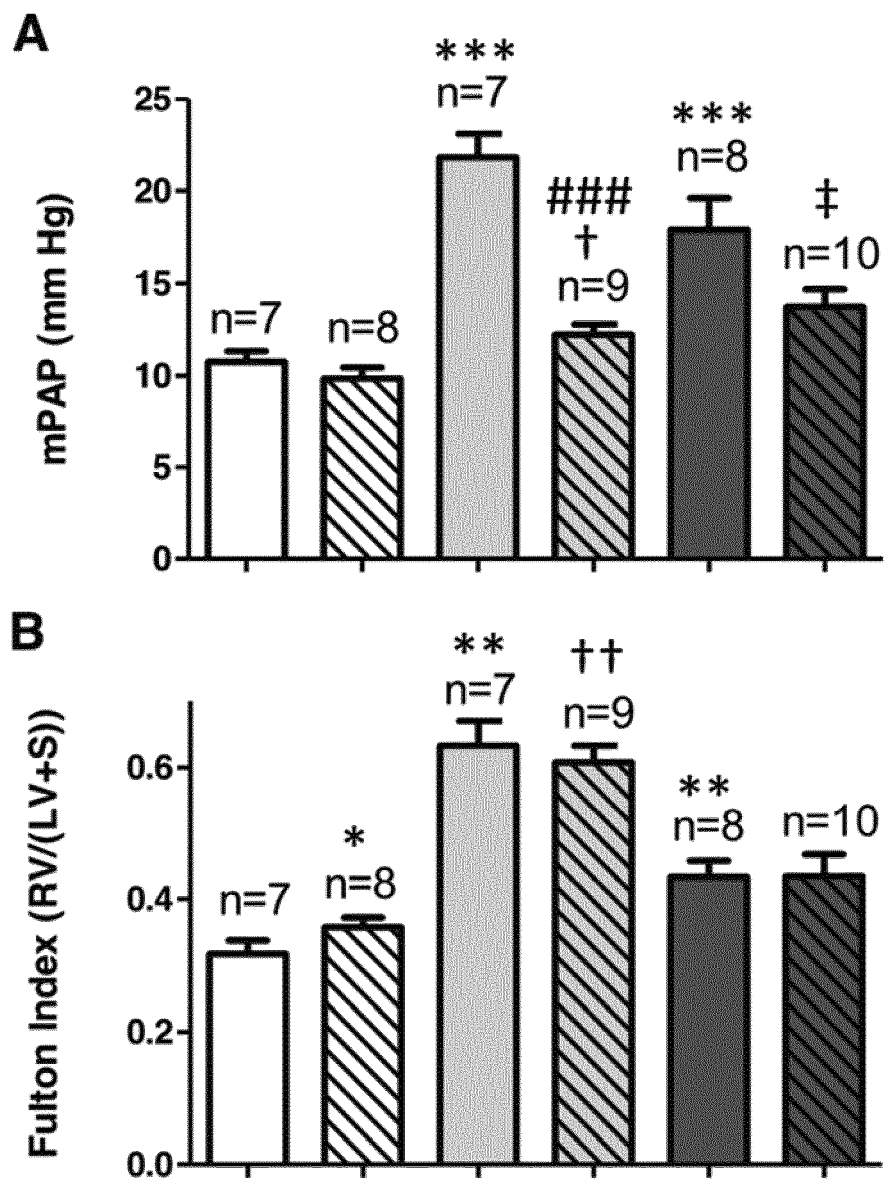
FIG. 13 is a set of two graphs showing the effect of AOL treatment on pulmonary arterial pressure and heart remodeling. Panel A: effect of AOL (hatched columns) on the mean pulmonary arterial pressure (mPAP) measured in normoxic rats (N, white columns), chronic hypoxic rats (CH, light grey columns) and monocrotaline-treated rats (MCT, dark grey columns). Panel B: right ventricular hypertrophy expressed as the Fulton index (i.e., ratio of right ventricle weight (RV) to left ventricle plus septum weight (LV+S)). n is the number of rats. *,  and * indicate a significant difference for $P<0.05$, 0.01 and 0.0001 respectively versus N. ### indicates a significant difference for $P<0.05$ versus CH. † and †† indicate a significant difference for $P<0.05$ and 0.01 respectively versus N+AOL. ‡ indicates a significant difference for $P<0.05$ versus MCT.

Results are expressed as mean±SEM of n independent observations. All data were analyzed using a non-parametric test for unpaired samples (Mann-Whitney test). FIG. 13 shows the effect of AOL on pulmonary arterial pressure (FIG. 13A) and heart remodeling (FIG. 13B). n indicates the number of rats for mPAP and Fulton index measurements. All bar graphs and statistics were performed with Graphpad PRISM software (v6, Graphpad Software). P<0.05 were considered significant. As seen, AOL had no significant effect on the control group (N rats). However, mean pulmonary arterial pressure was decreased in MCT rats treated with AOL, and even more significantly in CH rats treated with AOL. AOL treatment had however no effect on the Fulton index.

Figure 14:
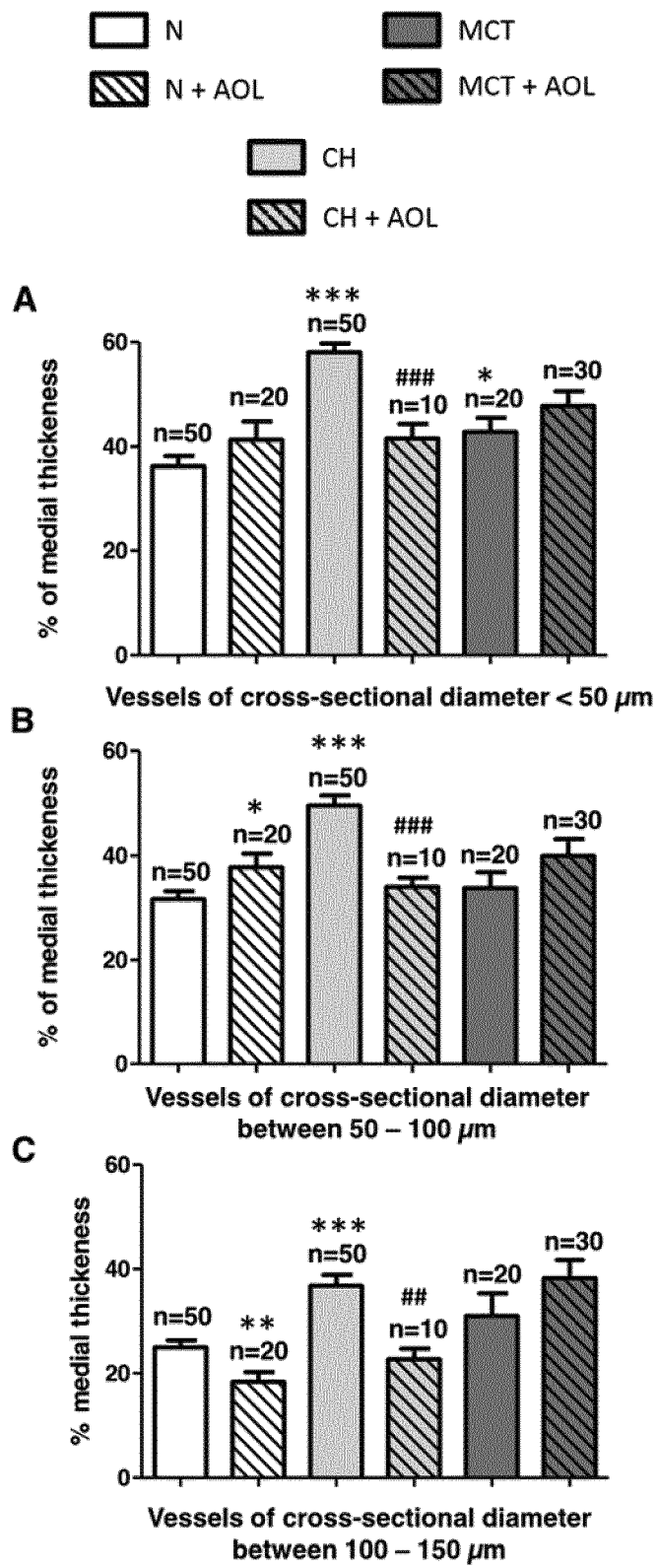
FIG. 14 is a set of graphs showing the effect of AOL on pulmonary arteries (PA) remodeling. The effect of AOL (hatched columns) on PA remodeling was assessed by measuring the percentage of PA medial thickness in normoxic rats (N, white columns), chronic hypoxic rats (CH, light grey columns) and monocrotaline-treated rats (MCT, dark grey columns). Intraacinar arteries observed to estimate PA remodeling were separated into three groups with different cross-sectional diameters (Panel A: under 50 µm; Panel B: between 50 to 100 µm; Panel C: between 100 to 150 µm). n is the number of vessels. *,  and * indicate a significant difference for P<0.05, 0.01 and 0.0001 respectively versus N. ## and ### indicate a significant difference for P<0.01 and 0.0001 versus CH. a significant difference for P<0.05 and 0.01 respectively versus N+AOL. ‡ indicates a significant difference for P<0.05 versus MCT.

FIG. 14 shows the effect of AOL on pulmonary arteries remodeling. n indicates the number of vessels analyzed for % of medial thickness measurement. All bar graphs and statistics were performed with Graphpad PRISM software (v6, Graphpad Software). P<0.05 were considered significant. AOL shows a significant effect in CH rats, in which pulmonary arteries diameter was reduced by 30%.

Conclusion

AOL treatment, at an oral dose of 10 mg/kg/day, has a significant effect in the prevention and/or treatment of pulmonary hypertension in vivo, in particular in group 3 pulmonary hypertension. Results indeed show a significant improvement of clinical symptomatology.

These data suggest that mitochondria play a major role in the pulmonary vasculature physiology, and extend the use of AOL to the treatment of pulmonary hypertension.

Example 7: Effect of AOL in Aging Disease and Progeroid Syndromes: Macular Degeneration The present study aims at evaluating the capacity for AOL to protect retina against progressive degeneration.

Material and Methods

Rats bred under cyclic low-intensity lighting were transferred to cyclic high-intensity lighting for one week and divided into 3 groups (non-treated animals, vehicle-treated animals and AOL-treated animals). Treated animals received injections of vehicle or AOL at a dose of 6 mg/kg/day, three times a day for the 7 days of the transfer (30 minutes before light-ON; at 01.00 µm; at 09.00 µm). After one week, animals were transferred in the dark (D0).

A control group ("untransferred") was not transferred to cyclic high-intensity lighting but received the same treatment as described above: injections of vehicle or AOL three times a day for 7 days, followed by a transfer in the dark (D0).

On the day following the transfer in the dark (D1), a first electroretinography is performed. It measures the electrophysiological signal which is generated by the retina, in response to a light stimulation. It is typically characterized by two waves, namely a-wave and b-wave. a-wave represents the initial corneal-negative deflection, derived from the cones and rods of the outer photoreceptor layers. It reflects the hyperpolarization of the photoreceptors due to closure of sodium ion channels in the outer-segment membrane. b-wave represents the corneal-positive deflection, derived from the inner retina (predominantly Muller and ON-bipolar cells). Analysis of the electroretinogram consists in measuring the amplitude and/or latency of these waves, as a function of the intensity of the light stimulation. a-wave amplitude, for a given light stimulation intensity, depends on the number of photoreceptors; whereas amplitude of b-wave, for a given light stimulation intensity and a given number of photoreceptors, indicates the signal transmission efficiency.

After D1's electroretinography, animals were transferred back under cyclic low-intensity lighting conditions, and a second electroretinography is performed at D15.

Animals were then sacrificed for histological analysis. The thickness of the various layers of the retina, in particular the thickness of the outer nuclear layer (ONL) and inner nuclear layer (INL) were measured (in µm, from the optical nerve and every 0.39 mm in the superior and inferior poles of the optic disc).

Results

Figure 15:
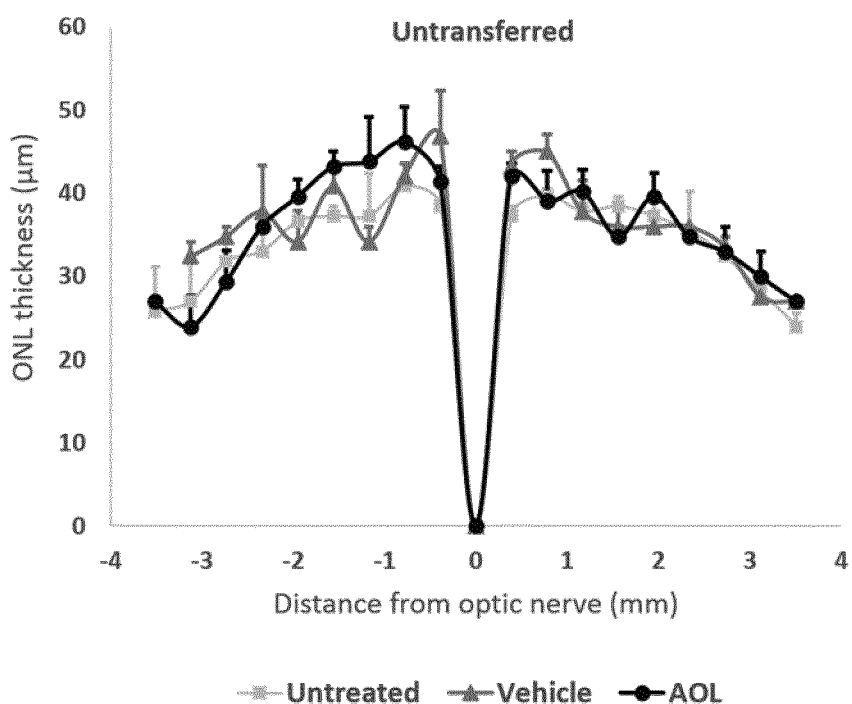
FIG. 15 is a set of graphs showing the effect of AOL on the thickness of the outer nuclear layer (ONL) of the retina, in progressive light-induced retinal degeneration. Panel A: effect of vehicle and AOL on "untransferred" animals. Animals were bred under cyclic low-intensity lighting and received injections of vehicle or AOL three times a day for 7 days. Fifteen days after the end of the treatment, histological analysis of the retina was carried out. Data are expressed as mean±SEM thickness of the ONL, for untreated animals (light grey, square dots), vehicle-treated animals (dark grey, triangle dots) and AOL-treated animals (black, round dots), in µm, from the optical nerve and every 0.39 mm in the superior and inferior poles of the optic disc. Panel B: effect of vehicle and AOL on "transferred" animals. Animals were bred under cyclic low-intensity lighting and transferred to cyclic high-intensity lightning for 7 days, during which they received injections of vehicle or AOL three times a day. At the end of the treatment, animals were transferred back under cyclic low-intensity lighting conditions, and histological analysis of the retina was carried out fifteen days later. Data are expressed as mean±SEM thickness of the ONL, for untreated animals (light grey, square dots), vehicle-treated animals (dark grey, triangle dots) and AOL-treated animals (black, round dots), in µm, from the optical nerve and every 0.39 mm in the superior and inferior poles of the optic disc.
Figure 15:
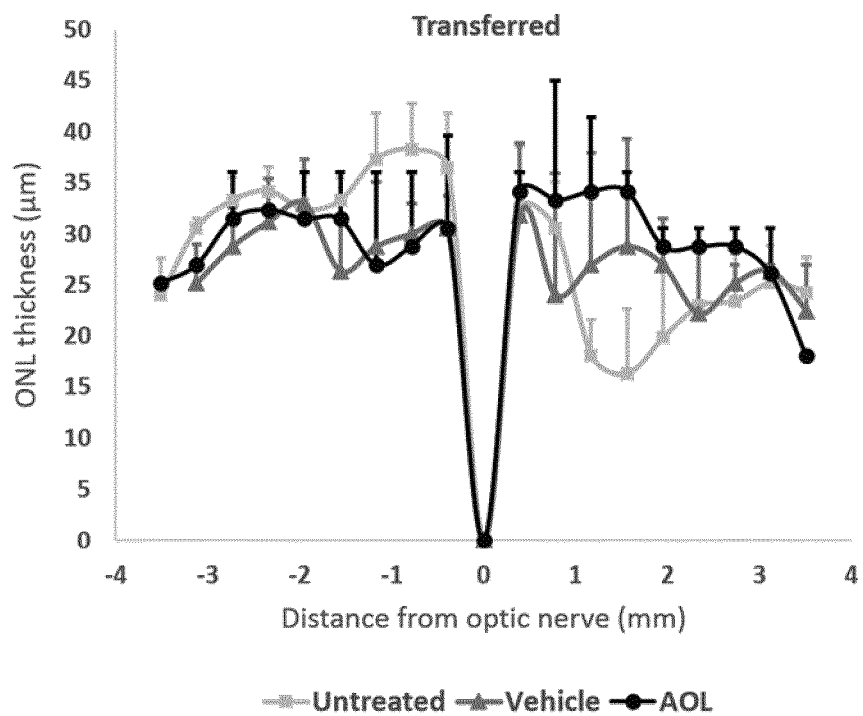

Histological analysis is reported on FIG. 15. It shows that, in the control group ("untransferred"), treatment with AOL has no effect on ONL's thickness (FIG. 15A). This suggests that AOL does not have a toxic effect on retina's photoreceptors.

On the contrary, transfer in cyclic high-intensity lighting conditions ("transferred") induces a significant decrease (by half in some areas) of the ONL, in non-treated animals. AOL however tends to protect the ONL against light-induced damages. Histological analysis has indeed shown a significant increase of the thickness of the ONL in AOL-treated/cyclic high-intensity lighting-exposed animals (FIG. 15B).

Conclusion

AOL treatment has a significant protective effect against light-induced damages on the retina. In particular, the thickness of the retina was shown to be preserved as compared to non-treated animals, after prolonged cyclic high-intensity lighting exposure.

Example 8: Effect of AOL in Diseases Related to Mitochondrial Dysfunctions

The present study aims at testing the effect of AOL in vivo, in a model of oxidative phosphorylation dysfunction.

Material and Methods

Mice deficient in mitochondrial Mn-Superoxide Dismutase (Sod2-KO) on a CD1-background were used. This genetic alteration leads to an adverse phenotype and the death of animals at an average of 8 days old. Mitochondrial superoxide dismutase is a free radical scavenging enzyme which transforms superoxide (highly reactive) into hydrogen peroxide (less reactive), that could then cross mitochondrial membranes and be detoxified by matrix and cytosolic anti-oxidant systems. The aim of this study was to test if AOL could rescue the Sod2-KO phenotype through its activity on $I_Q$ superoxide production.

After birth, pups were genotyped (3 day-old) and the litter size was reduced to 6 pups per cage. Animals were then treated (AOL in Kolliphor®—5 mg/kg) or not (Kolliphor® only, noted KOL below). The choice of the dosage was mainly driven by the solubility limit of the compound (2.8 mM in Kolliphor®) and the maximum injectable volume in pups (6 to 7 μL per gram body mass). Two studies were conducted on two different generations from the same parents: lifespan; and succinate dehydrogenase activity in heart (SDH) and Oil Red O staining in liver. Animals were weighed and injected (intra-peritoneal) daily.

Succinate dehydrogenase activity is a marker of superoxide in the mitochondrial matrix. Thus, a lack of SOD2 is associated with a decrease of SDH activity in heart. The aim of this experiment was to test whether or not AOL could restore SDH activity in KO mice.

Oil Red O staining is a marker of lipid that has been shown to accumulate in Sod2-KO liver. However, the direct link between superoxide/hydrogen peroxide production and liver lipid accumulation is not established. The aim of the study was to test the potency of AOL to prevent liver lipid accumulation in Sod2-KO mice.

Results

Lifespan 4 groups were constituted:

1—WT-KOL (n=7), a group of wild-type mice treated with the vehicle only;

2—WT-AOL (n=17), a group of wild-type mice treated with AOL;

3—KO-KOL (n=2), a group of Sod2-KO mice treated with the vehicle only;

4—KO-AOL (n=4), a group of Sod2-KO mice treated with AOL.

Animals were injected once a day from 3 days old until their death.

Figure 16:
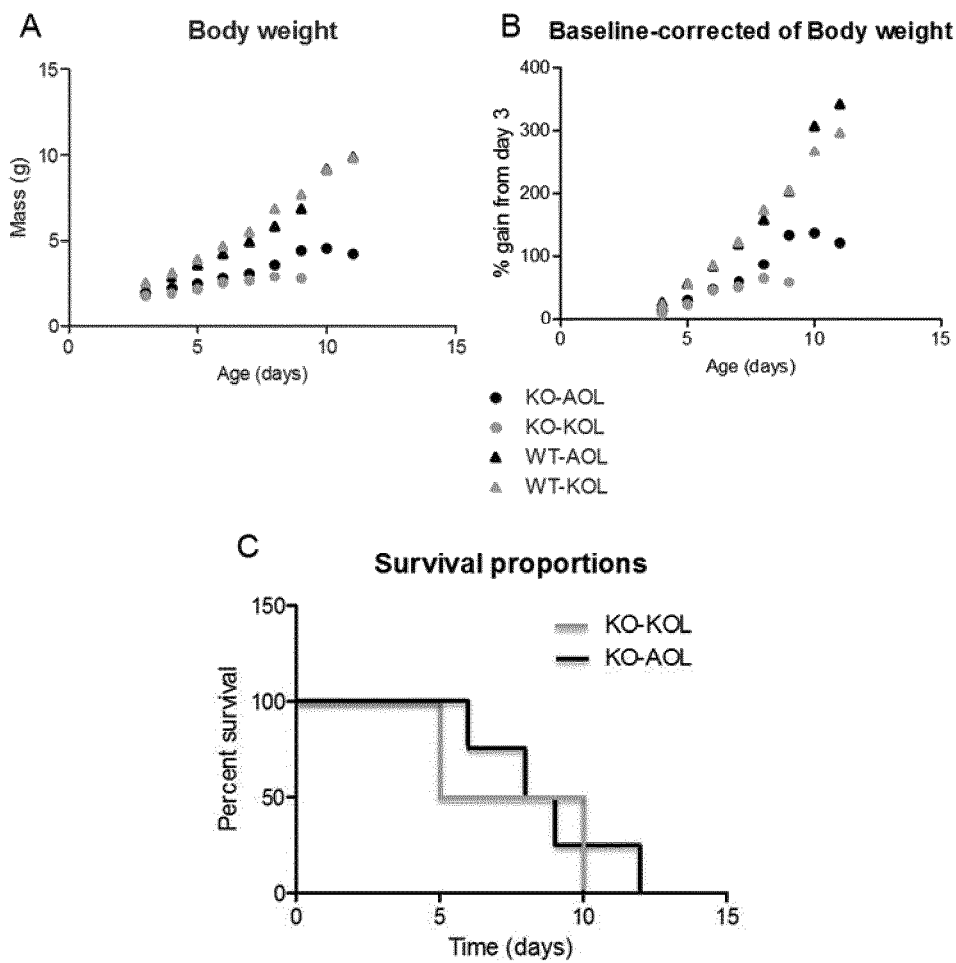
FIG. 16 is a set of graphs showing a lifespan SOD2-KO experiment on four groups of mice (WT-KOL: wild-type mice treated with vehicle; WT-AOL: wild-type mice treated with AOL; KO-KOL: SOD2-KO mice treated with vehicle; KO-AOL: SOD2-KO mice treated with AOL). Data are expressed as mean values. Panel A: evolution of mice body weight, in grams over time, in days. Panel B: baseline-corrected of mice body weight, as a percentage of weight gain over time, in days. Panel C: survival proportion among the KO-KOL and KO-AOL groups, in percentage over time, in days.

FIG. 16A and FIG. 16B show the evolution of body weight (A) and percentage of initial body weight. These results show that body weight and body weight gain were lower in KO-mice than in WT-mice. Treatment with AOL however tends to alleviate this effect as seen from day 8 to 12, suggesting a potential beneficial effect of the compound.

FIG. 16C shows the survival proportion of Sod2-KO mice whether they were treated with AOL or not. As expected in view of the above results, both median lifespan and maximal lifespan were slightly improved by AOL treatment in KO mice, with AOL-treated mice living up to 2 days longer as compared to untreated mice, supporting a beneficial effect of AOL.

SDH activity in heart & Oil Red O staining 5 groups were constituted:

1—WT-non-injected (n=6), a group of untreated wild-type mice;

2—WT-KOL (n=6), a group of wild-type mice treated with the vehicle only;

3—WT-AOL (n=6), a group of wild-type mice treated with AOL;

4—KO-KOL (n=4), a group of Sod2-KO mice treated with the vehicle only;

5—KO-AOL (n=6), a group of Sod2-KO mice treated with AOL.

In this study, animals were treated daily (5 mg/kg) from day 3 to day 5. Heart and liver were harvested at day 6.

Figure 17:
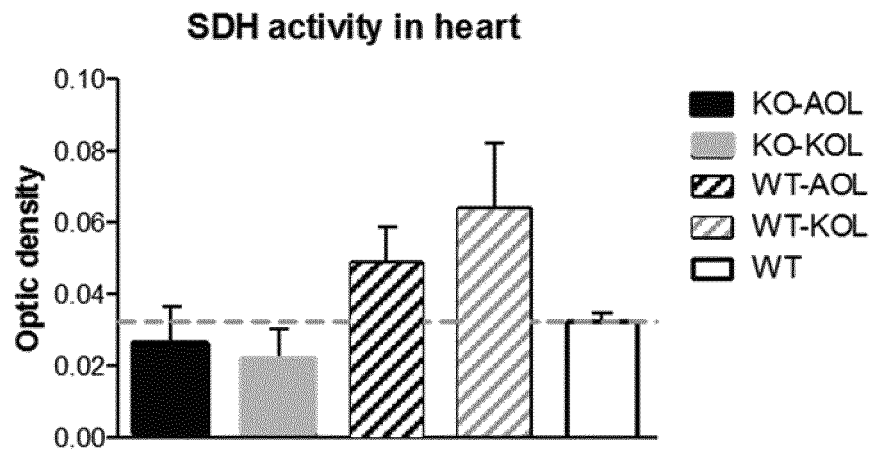
FIG. 17 is a graph showing the succinate dehydrogenase (SDH) activity in heart, among five groups of mice (WT-KOL: wild-type mice treated with vehicle; WT-AOL: wild-type mice treated with AOL; KO-KOL: SOD2-KO mice treated with vehicle; KO-AOL: SOD2-KO mice treated with AOL; WT: wild-type untreated mice). The optical density of SDH reaction sampled from heart sections was measured with the image processing software Image Analyst MKII (Akos). This density was expressed in the form of mean grey level where mean grey level=sum of grey/number of pixels measured. Data are expressed as mean values of the measured optical density.

As expected, SDH activity tended to decrease (not significant) in KO compared to WT animals. However, AOL showed only a very slight increase in SDH activity in KO mice, but could not restore SDH activity to the levels of WT mice (FIG. 17).

Figure 18:
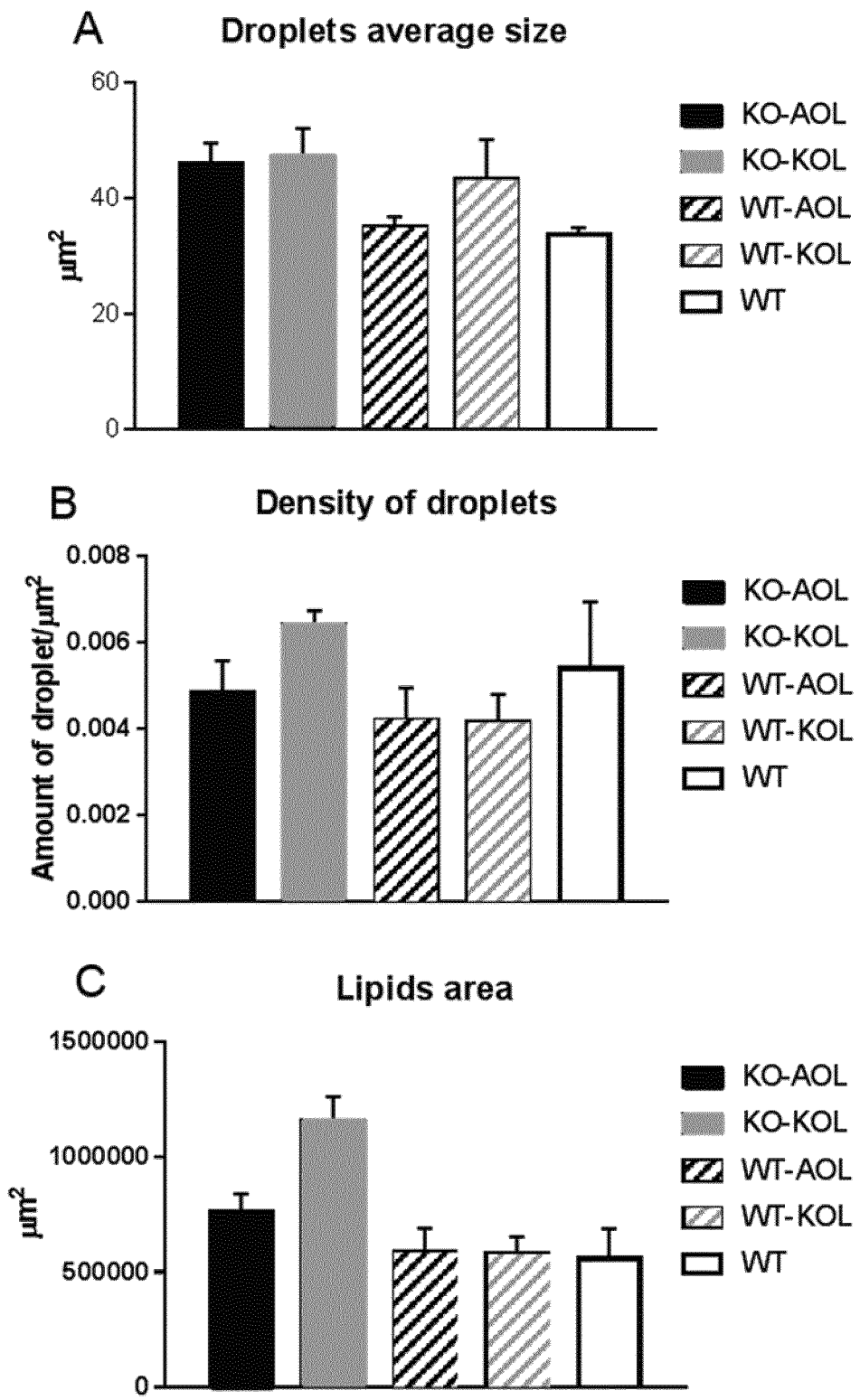
FIG. 18 is a set of graphs showing Oil Red O staining of liver slices from WT and SOD2-KO mice, treated or not with AOL. Histogram represent the average size of lipids droplets (Panel A), the droplet density (droplets number/liver area) (Panel B) and the total lipid area (average size×droplets number) (Panel C).

FIG. 18 shows lipid droplets average size (Panel A), density (Panel B) and area (Panel C). Untreated KO mice exhibited a high lipid content phenotype compared to WT animals. In AOL-treated KO mice however, lipid droplets density decreased as compared to untreated animals. More importantly, these results also show that AOL treatment was able to restore the total lipid area in KO mice, consistent with on-target suppression of mitochondrial superoxide production in vivo in Sod2-KO mice.

Conclusion

In vivo studies show encouraging results. Although AOL treatment could not fully counteract the effects of SOD2 depletion in mice, results show that lifespan could still be extended by a couple of day as compared to untreated KO animals, together with an alleviation of the decrease in body weight gain. This suggests a potential effect of AOL.

AOL bioavailability is known to be very short. Thus, treatment with higher doses might lead to improve AOL effects in these experiments. However, constitutive KO remains a high adverse phenotype to rescue with only one very specific treatment and may require synergic action with other drugs.

In vivo, results also showed that AOL could restore lipid content and/or prevent lipid accumulation in liver of Sod2-KO mice.

Example 9: AOX Affects Mitochondrial Oxidative Phosphorylation at High Concentrations (Over 20 μM)

Material and Methods

Animal Procedures and Ethics Statement

All experiments described were carried out in agreement with the National and European Research Council Guide for the care and use of laboratory animals. P. Diolez has a valid license to conduct experiments on animals by the Service Vétérinaire de la Santé et de la Protection Animale of the Ministère de l'agriculture et de la Forêt, France (Mar. 17, 1999, license number 3308010).

Materials

All the chemicals were reagent grade, purchased from Sigma Chemical (St. Louis, Mo.), except for sucrose and NADH oxidase (that were obtained from Merck (Darmstadt, Germany)). AOL and AOX were gift from OP2 (Bordeaux, France). 15 mM stock solutions were prepared in DMSO, and kept in darkness at 0° C. for only few days.

Isolation of Heart Mitochondria

Male Wistar rats (250-325 g; obtained from Janvier Labs, Le Genest-Saint-Isle, France) were killed by stunning and cervical dislocation, and the heart was quickly removed and washed in cold isolation medium containing 100 mM sucrose, 180 mM KCl, 50 mM Tris, 5 mM $MgCl_2$, 10 mM EDTA, and 0.1% (w/v) defatted BSA (pH 7.2).

Isolation of heart mitochondria was performed in a cold chamber. Before homogenization, hearts (about 1.5 g) were minced with scissors and treated for 5 minutes in 5 mL of the same medium supplemented with protease (2 mg of bacterial proteinase type XXIV per mL of isolation buffer) with stirring. The tissue suspension was poured into a 50-mL glass Potter homogenizer, diluted with 20 mL of isolation buffer, then homogenized for 3 minutes using a motorized Teflon pestle. The homogenate was filtered through bolting cloth (Sefar Nitex) to remove debris, and centrifuged at 8,000 g for 10 minutes. The resulting pellet was rinsed with 5 mL of isolation buffer, resuspended in 25 ml of the same buffer, then subjected to low speed centrifugation (400 g) for 8 minutes. The resulting supernatant was centrifuged twice at 7,000 g for 15 minutes to yield a washed mitochondrial pellet that was gently resuspended in 150 µL of isolation buffer. Protein concentration was determined by the Bradford method (Sigma, kit # B6916) using BSA as standard. Mitochondria were kept on ice at a final concentration of 40-50 mg/mL for less than 5 hours.

Mitochondrial Oxygen Consumption and ATP Synthesis

Oxygen consumption rates of heart mitochondria (0.1 mg/mL), incubated in the absence or presence of AOX at increasing doses (from 0 to 100 µM final concentration), were recorded polarographically under constant stirring at 25° C. using a high-resolution oximeter (Oxygraph-2K, Oroboros Instruments, Austria). The respiration medium consisted in 140 mM sucrose, 100 mM KCl, 1 mM EGTA, 20 mM $MgCl_2$, 10 mM $KH_2PO_4$, and 1 g/L (w/v) BSA essentially fatty acid free (pH 7.2).

ATP synthesis was measured under the same conditions using a high sensitivity pH electrode (Metrohm) as previously described (Gouspillou et al., 2014. *Aging Cell.* 13(1): 39-48).

Mitochondrial $ROS/H_2O_2$ Production

Rates of $ROS/H_2O_2$ production from heart mitochondria were assessed through the oxidation of the colorless, non-fluorescent indicator Amplex Red in the presence of exogenous horseradish peroxidase (HRP, EC 1.11.1.7, Sigma). $H_2O_2$ reacts with Amplex Red in a 1:1 stoichiometry, yielding the fluorescent compound resorufin (excitation: 560 nm; emission: 585 nm) which is stable once formed. Fluorescence was measured continuously with a spectro-fluorometer equipped with temperature control and stirring (SAFAS Xenius, Monaco).

Isolated mitochondria (0.1 mg/mL) were incubated in the same experimental buffer than previously, supplemented with 15 µM Amplex Red and 10 µg/mL HRP. Glutamate (5 mM)/malate (2.5 mM) together with succinate (5 mM) were used as complex I and complex II substrates, respectively. Experiments were conducted under non-phosphorylating conditions in the presence of 15 µM atractyloside. Afterwards, rotenone (1.5 µM), antimycin A (2 µM), and myxothiazol (0.2 µM) were sequentially added to inhibit the redox centers within the electron transfer chain (see FIG. 2), namely sites $I_Q$, $I_F$ (with rotenone), $III_{Qi}$ (with antimycin A) and $III_{Qo}$ (with myxothiazol). Assay was finally calibrated with known amounts of $H_2O_2$ (steps of 300 nM), in the presence of all relevant compounds, including AOX. The control test of the absence of effect of AOL, AOX and Oltipraz on the Amplex Red assay itself and NAD(P)H oxidase ROS/1202 production was carried out in the absence of cardiac mitochondria and the presence of NAD(P)H oxidase (EC 1.6.3.3, 5 mU/mL, Sigma) and NADH (100 µM) solutions.

Results

Figure 19:
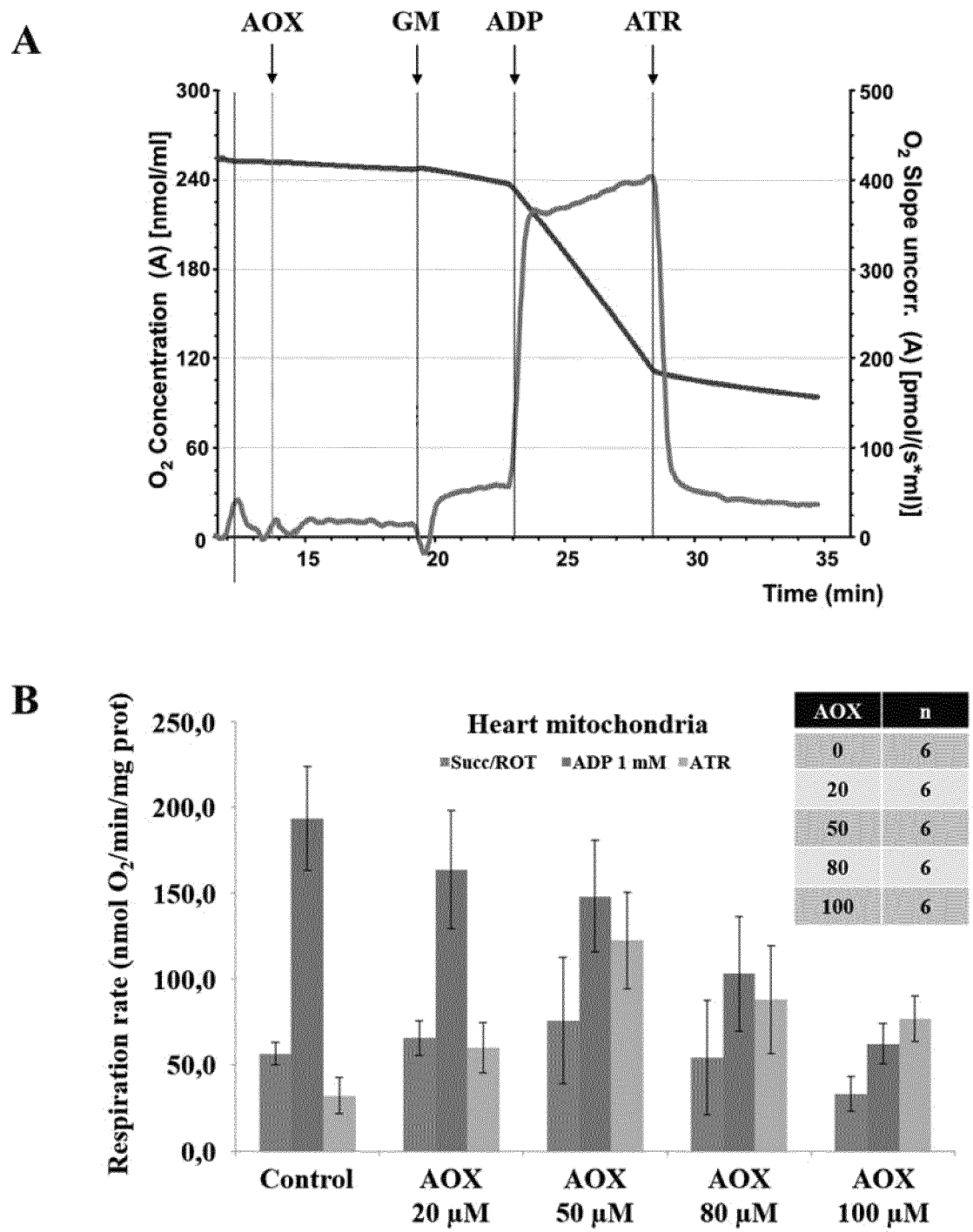
FIG. 19 shows the effect of AOX on mitochondrial oxidation. A typical experiment showing mitochondrial respiration under various oxidative phosphorylation conditions in the presence of AOX is shown in FIG. 19A. AOX has been added to mitochondria for a 5-minute-incubation before oxidative phosphorylation assay. Oxygen consumption (dark grey trace) starts after substrate addition (GM: Glutamate-Malate) and is activated by ADP (phosphorylation state). Phosphorylation is stopped by ATR (atractyloside) and low residual respiration reflects mitochondrial inner membrane integrity.

We first tested if AOX compound affects oxidative phosphorylation directly on isolated mitochondria from rat heart. This has been carried out by using the now classical oxygraph method (FIG. 19A). Mitochondria were first incubated with various AOX concentrations (20 to 100 µM), then respiratory substrate was added (substrate state, black curve), followed by a saturating ADP concentration to get the maximal oxidative phosphorylation rate (slope of oxygen consumption, grey curve), and finally the addition of atractyloside (ATR) which inhibits the ADP/ATP translocator and gives the mitochondrial leak rate under non-phosphorylating conditions (FIG. 19A). FIG. 19B presents the results obtained with succinate (+ rotenone) to feed electrons to respiratory chain. This substrate has been chosen since it most closely reflects respiratory chain regulation. The results indicate that under "substrate" state and ATR state (inner membrane proton leak rate), AOX induced an increase for concentrations up to 50 µM followed by a decrease for concentrations over 50 µM. These data suggest an uncoupling effect of AOX on oxidative phosphorylation for concentrations higher than 20 µM and a concomitant inhibition of oxidation rate. Data demonstrate under these conditions, the effect of high concentrations of AOX (higher than 20 µM) on mitochondrial oxidative phosphorylation—i.e., on both respiratory chain activity and ATP synthesis—as well as on mitochondrial inner membrane integrity (leak rate measured after ATR addition).

Figure 20:
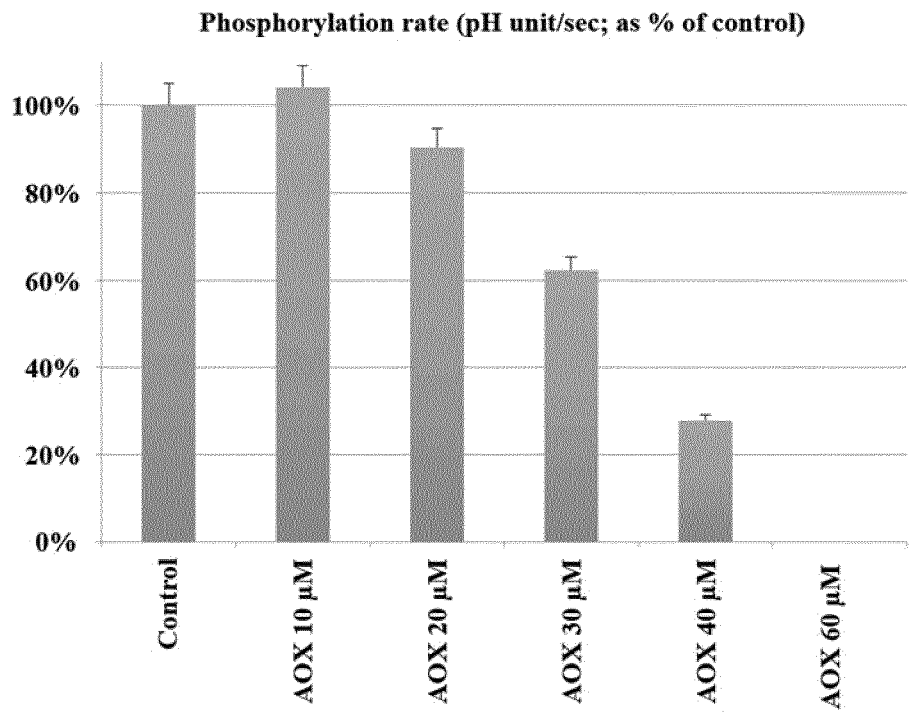
FIG. 20 shows the effect of AOX on mitochondrial ATP phosphorylation. Phosphorylation rate has been measured simultaneously with oxidation rate as previously described in Gouspillou et al. (2014. Aging Cell. 13(1):39-48), and the effects of increasing concentrations of AOX have been reported. Results are expressed as a relative percentage to the control of the pH unit/sec evolution.

FIG. 20 presents the effects of AOX on the phosphorylation rate (ATP synthesis rate) of isolated rat heart mitochondria. Results confirm that concentrations lower than 20 µM do not modify ATP synthesis by isolated mitochondria. However, higher concentrations do effectively decrease phosphorylation rate and completely abolish it at 60 µM.

Example 10: AOX Inhibits Superoxide/$H_2O_2$ Production by Mitochondria

As previously stated, mitochondrial ROS production is highly dependent on mitochondrial activity and conditions. Although we tested the effects of AOX on ROS production by mitochondria under numerous conditions, we chose to present here, for the sake of clarity, only the most demonstrative results of the very specific effects of AOX. The presence of the complete substrate combination (i.e., glutamate, malate and succinate) (FIG. 2A), giving the electrons to the whole respiratory chain, is the most representative of in situ conditions in the cell where metabolism is active. Furthermore, maximal mitochondrial $ROS/H_2O_2$ production does not occur under conditions of high mitochondrial phosphorylation but under conditions of high reduction of electron transporters, i.e., low or no phosphorylation. These conditions are fulfilled in the presence of ATR and we could effectively verify that the addition of ATR under conditions of saturating ADP triggered the production of ROS which was at the detection limit under maximal phosphorylating conditions (results not shown). Under these conditions, ROS are produced at different sites of the respiratory chain (Orr et al., 2013. *Free Radic. Biol. Med.* 65:1047-1059; Quinlan et al., 2013. *Redox Biol.* 1:304-312) (FIG. 2).

We designed a series of inhibitor titrations in order to decipher the action of AOX on ROS production by the whole respiratory chain under conditions of maximal ROS production (FIG. 2E). In the presence of substrate combination and the absence of specific inhibitors of the complexes, ROS production is at maximum and mainly comes from reverse electron transport at site $I_Q$ (FIG. 2A). After addition of rotenone, a classical inhibitor of complex I which specifically binds to $I_Q$ catalytic site, the ROS production decreases strongly and occurs almost entirely at site $III_{Qo}$ (FIG. 2B). Therefore, the decrease in ROS production (measured by the Amplex Red method, FIG. 22) after rotenone addition represents the activity of ROS production by complex I.

Figure 21:
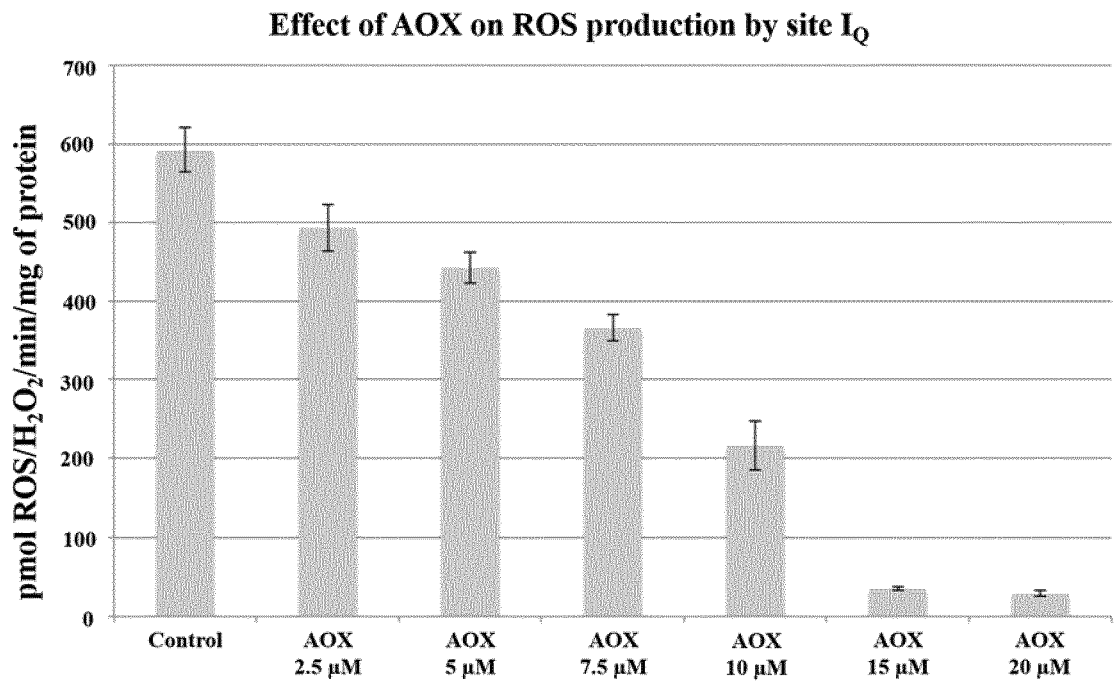
FIG. 21 shows the effect of increasing AOX concentrations on oxygen radicals production by isolated mitochondria in the presence of substrates of both complexes I and III (glutamate, malate and succinate) in the presence of ATR, therefore under conditions of major production by complex I. The measurement of ROS produced by mitochondria was carried out by using the classical peroxidase-Amplex Red system which measures the appearance of $H_2O_2$ by the oxidation of Amplex Red giving fluorescent resorufin (see FIG. 22B).

FIG. 21 illustrates the effect of increasing concentrations of AOX (from 2.5 to 20 µM) on $ROS/H_2O_2$ production measured under these conditions. It clearly appears from the results presented in this figure that AOX strongly inhibits the ROS production by complex I, at concentrations lower than required with AOL (cf. FIG. 3 for comparison). Indeed, AOX concentrations as low as 2.5 µM showed an inhibitory effect on the ROS production by site $I_Q$, with an estimated $IC_{50}$ of about 9.5 µM (Minimum: −72.5272±68.64; Maximum: 554.045±19.73; $IC_{50}$: 9.46768±1.018; Hill coefficient: 2.61579±0.5706).

Figure 22:
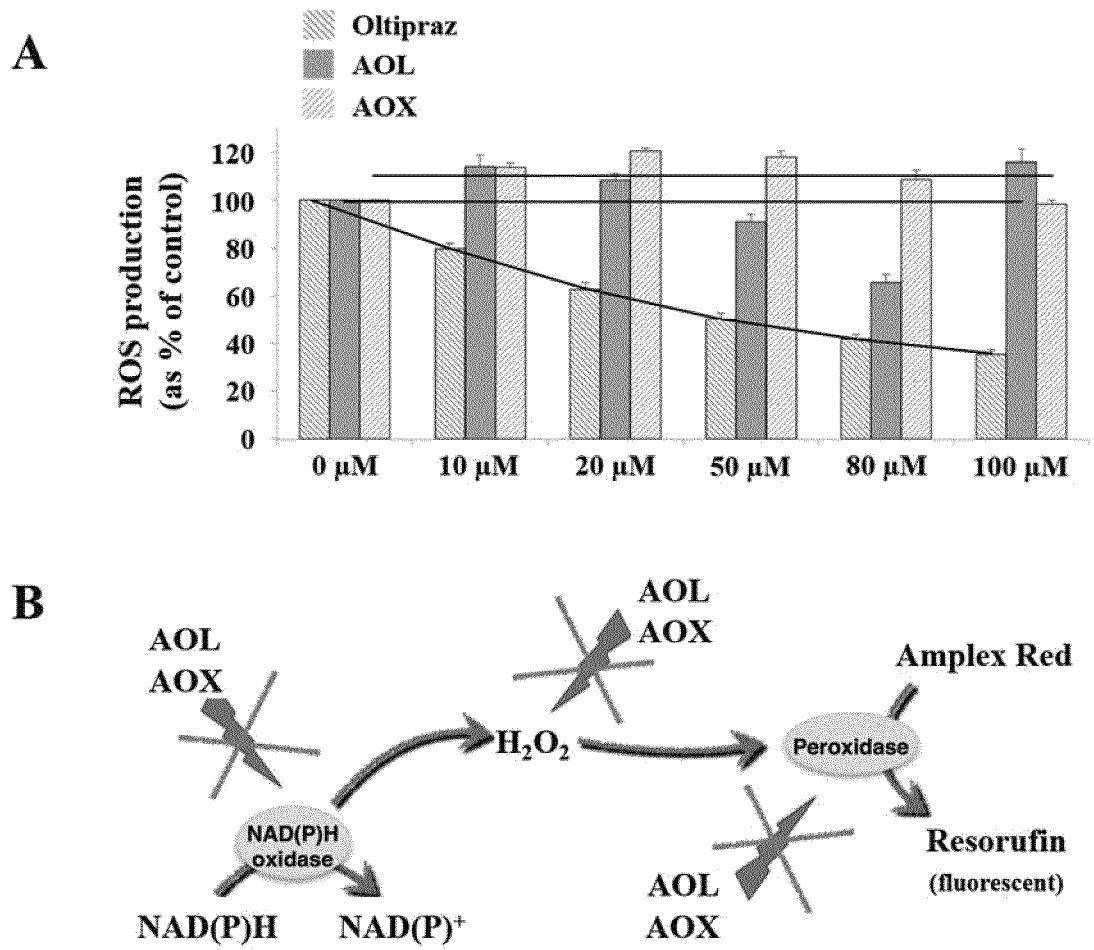
FIG. 22 shows the absence of effect of AOX on non-mitochondrial ROS in an in vitro assay, in comparison with AOL and Oltipraz. Non-mitochondrial ROS/$H_2O_2$ were obtained by using commercially available NAD(P)H oxidase in the presence of reduced NAD(P)H and again measured using the classical peroxidase-Amplex Red system (FIG. 22B). The effect of increased concentrations of the different molecules tested is presented in FIG. 22A. Straight horizontal lines represent the averaged percentage of ROS production across all concentrations tested, for AOL (99.2%) and of AOX (109.9%).

Example 11: AOX does not Scavenge Non-Mitochondrial Superoxide/$H_2O_2$ Production by NAD(P)H Oxidase The mechanism of action of AOX was further tested in vitro using the peroxidase-Amplex Red system utilized for the measurement of $ROS/H_2O_2$ by mitochondria, which in fact measures the appearance of $H_2O_2$ by the oxidation of Amplex Red to the fluorescent resorufin (FIG. 22). In the absence of mitochondria and by adding instead a $H_2O_2$-producing system to the assay, it was possible to test the effect of AOX on this non-mitochondrial superoxide/$H_2O_2$ production. This has been carried out by using commercial NAD(P)H oxidase which produces $H_2O_2$ in the presence of added NAD(P)H and measuring the reduction of Amplex Red to resorufin. We compared the effects of increasing concentrations (10 to 100 µM) of AOX to those of AOL and Oltipraz (FIG. 22A). Results presented show that while both AOL and AOX had no global effect on ROS measurement under these conditions, Oltipraz constantly decreased the amount of ROS measured by the assay. These results therefore demonstrate that Oltipraz either inhibits NAD(P)H oxidase or acts as a moderate (poor) radical scavenger and binds superoxide/$H_2O_2$ which are not available for peroxidase assay, but in all circumstances, inhibits non-mitochondrial (mimicking cytosolic) superoxide/$H_2O_2$ production. They also exclude any effect of AOX and AOL on the NAD(P)H oxidase or on the peroxidase activity. These results confirm that AOX and AOL do not interfere either with the measurement system or directly interact with $H_2O_2$. Interestingly, these results also demonstrate that AOX and AOL do not inhibit the $ROS/H_2O_2$ production by the NADP(H) oxidase, which is one—if not the—major non-mitochondrial $ROS/H_2O_2$ producer in the cells. The scheme on FIG. 22B recapitulates the different information on the mode of action of AOX and AOL on $ROS/H_2O_2$ production by mitochondria and NAD(P)H oxidase.

When tested on isolated mitochondria from rat heart, AOX effectively decreases mitochondrial $ROS/H_2O_2$ production (in isolated mitochondria, $H_2O_2$ is produced from the reduction of ROS by mitochondrial superoxide dismutase). However, the results presented here clearly demonstrate that AOX does not act as an antioxidant or radical scavenger. While antioxidants are general $ROS/H_2O_2$ scavengers, AOX presents a selectivity towards the formation of ROS by site I in complex I, which demonstrates that AOX does not simply interact with superoxide radicals but specifically prevents their formation in complex I. In that respect, AOX therefore appears as a member of a brand-new class of oxidative stress protectants, by preventing ROS formation and thus being more active to protect mitochondria from their own ROS. We also show here some evidences that AOX may only interact with mitochondria without affecting oxygen radicals' formation in cytosol, and therefore would not affect intracellular signalization.

Inhibition of complex I activity by rotenone or the neurotoxin $MPP^+$ has been linked to parkinsonism in both rodents and humans, suggesting a link between dysfunctional complex I, ROS production, and neurodegeneration (Langston et al., 1983. Science. 219(4587):979-980; Betarbet et al., 2000. Nat. Neurosci. 3(12):1301-1306). In contrast, comparative analyses show an inverse relationship between maximal superoxide/$H_2O_2$ production from site $I_Q$, but not site $I_F$, and maximum life span across diverse vertebrate species (Lambert et al., 2007. Aging Cell, 6(5): 607-618; Lambert A J et al., 2010. Aging Cell, 9(1):78-91). Therefore, selective modulators of superoxide/$H_2O_2$ production from site $I_Q$ or site $I_F$ would offer unique opportunities to probe the putative role of mitochondrial ROS production in normal and pathological processes (Orr et al., 2013. Free Radic. Biol. Med. 65:1047-1059).

These results effectively demonstrate that AOX is not a radical scavenger; otherwise its effects on ROS measurements would be independent of the origin of the superoxide/$H_2O_2$ origin: mitochondrial or non-mitochondrial. Although the mechanism has still to be investigated, evidence is presented here that AOX compound specifically interferes with mitochondrial complex I and selectively inhibits superoxide production from the ubiquinone-binding site of complex I (site $I_Q$).

In conclusion, it appears that AOX properties may represent a breakthrough in the search for specific mitochondria-targeted modulators of $ROS/H_2O_2$ production in cells. AOX acts upstream from ROS production, therefore insuring higher protection than classical antioxidants.

Example 12: AOX Specifically Inhibits Mitochondrial ROS Production but not Cytosolic ROS Production Material and Methods Human non-small cell carcinoma cell line H460 and A549 were obtained from ATCC. Cells were cultured in growth medium consisting of DMEM (GIBCO), 10% FBS (GIBCO) and 100 units of penicillin and 100 µg/mL streptomycin (GIBCO). The cells were maintained in either 75-$cm^2$ T-flasks or 175-$cm^2$ T-flasks (BD Biosciences) in an incubator (model 3100 series, Forma Scientific, Marietta, Ohio) controlled at 37° C., 95% humidity, and 5% $CO_2$. Cell culture medium was refreshed every other day. Every 2 to 3 days, H460 and A549 cultures were detached from the flasks using a 0.25% trypsin solution (Gibco) and subcultured. All cultures were maintained at 80-90% confluence at the time of subculture.

Cytotoxicity screening was carried out by sulforhodamine B colorimetric assay. A549 and H460 cells ($2 \cdot 10^3$) were seeded in a 96-well plate, and after adherence, cells were incubated with 5 to 500 µM of AOL or AOX or control dimethyl sulfoxide (DMSO). Cytotoxicity was evaluated after 48 hours treatment sulforhodamine B (SRB) assay, according to Vichai (Vichai et al., 2006. Nat. Protoc. 1(3): 1112-6).

Cell migration assays were performed in Transwells (Corning Inc., 8.0-µm pore size). For migration assay, $2 \cdot 10^4$ cells in serum-free medium were added to the upper wells. Media containing 10% FBS were added to the lower wells.

Cells that migrated through the filter after 16 hours were stained with 0.2% crystal violet and counted using the software Image J.

Statistical analysis was performed using GraphPad Prism 6 (GraphPad Software, Inc.). The results are expressed as mean±SEM values for n independent experiments. Comparisons between groups were done by one-way ANOVA and a posteriori Dunnett's test. When appropriate, unpaired Student's t-tests or Mann-Whitney's test were employed. Differences of $p<0.05$ were considered to be significant.

Results

Absence of Cytotoxicity of AOX on Cultured Cells

Figure 23:
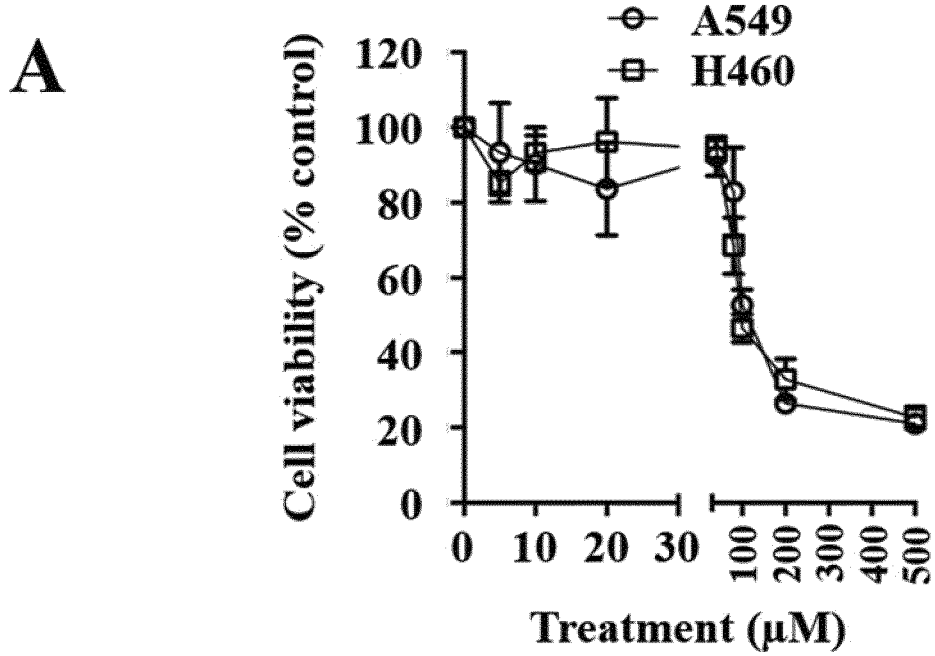
FIG. 23 shows the effect of AOX on the viability of carcinoma cell lines A549 and H460, expressed in % to the control (0 µM AOX). Cells were incubated with increasing doses, from 0 to 500 µM AOX, and cytotoxicity was assessed by sulforhodamine B (SRB) assay (FIG. 23A). Results are also expressed as the log of AOX concentration (FIG. 23B).
Figure 23:
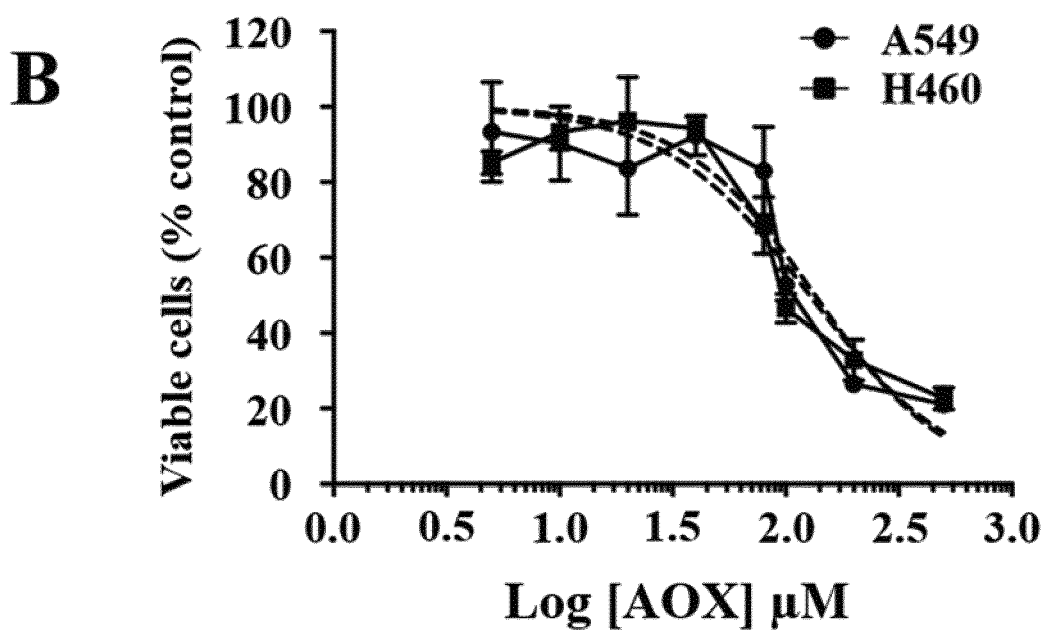

Cytotoxicity of AOX was performed on two carcinoma cell lines (H460 and A459) for a large range of concentrations (0 to 500 µM). Results are presented in FIG. 23.

Positively no significant toxicity could be observed for concentrations lower than 100 µM, and cell viability only decreased abruptly for higher concentrations of AOX (FIG. 23A). By plotting these results on a semi-logarithmic plot (FIG. 23B), we could calculate the $IC_{50}$ for high dose AOX toxicity as 134.8±0.3 µM. These results demonstrate that AOX has no harmful effect on cultured cells, even for high concentrations (100 µM).

Absence of Effect of AOX on Carcinoma Cells Respiration

The effects of AOX (0 to 40 µM) were assessed on carcinoma cells using the classical oxygraphic approach and compared to the effects of sister molecule AOL.

Figure 24:
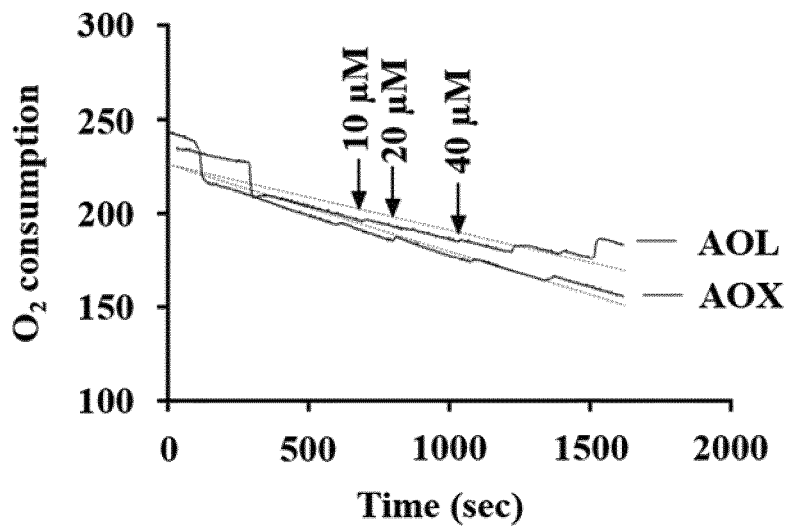
FIG. 24 shows the absence of effect of AOX and AOL on the respiration of H460 cells, as assed by oxygraphic approach.

Oxygen consumption of H460 resting cells has been measured continuously and increasing concentrations of AOL and AOX (0 to 40 µM) have been injected to the preparation (FIG. 24). It can be seen than there has been no change in the rate of oxygen consumption by H460 cells either with AOX or with AOL, indicating the absence of intracellular perturbation of mitochondrial activity and cell energetic metabolism. These results confirm the absence of harmful effect of AOL and AOX on cell functions.

Effect of AOX on Carcinoma Cells Metastatic Activity

Figure 25:
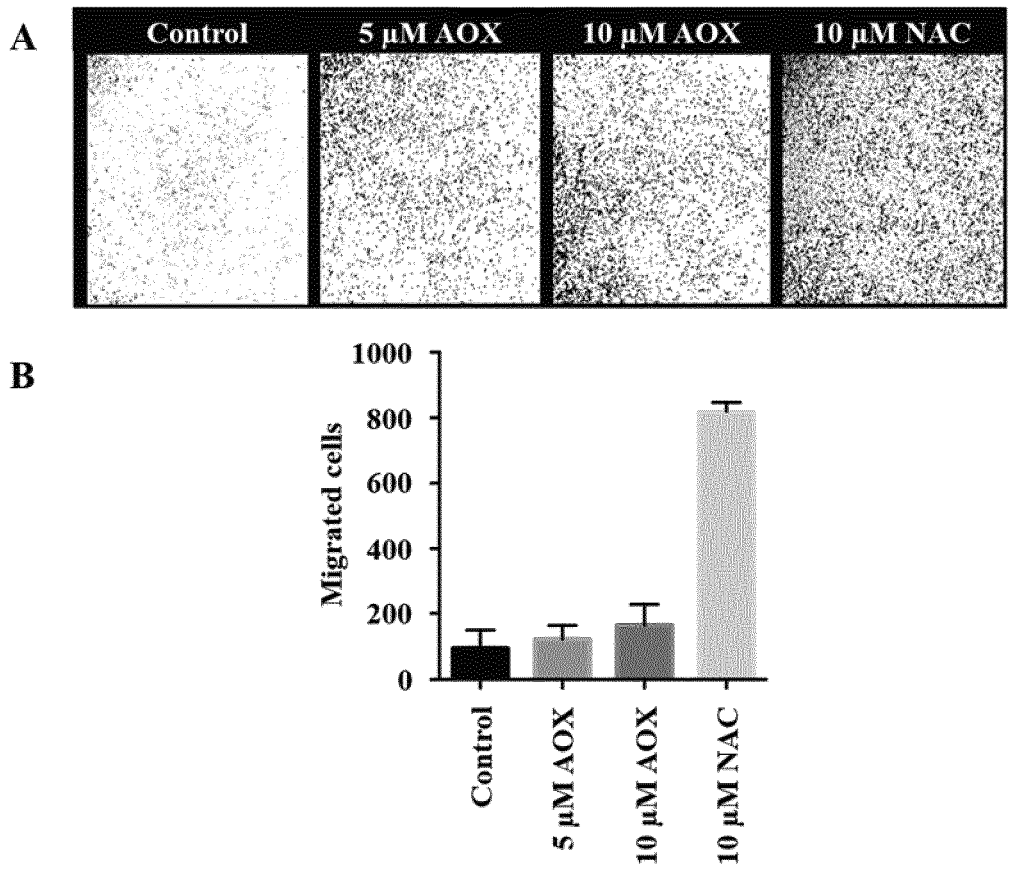
FIG. 25 shows the absence of effect of AOX on metastatic activity of carcinoma cells, using the Transwell test. Briefly, H460 carcinoma cells were placed on the upper layer of a cell permeable membrane, and following an incubation period, the cells that have migrated through the membrane are stained and counted.

The Transwell test of cell migration has been utilized for this assay and the migration of H460 carcinoma cells has been measured in the presence of two different concentrations of AOX (5 and 10 µM) and compared to the effect of 100 µM N-acetyl cystein (NAC) as a positive control of cytosolic ROS production (FIG. 25).

FIG. 25A presents the photographs of dyed cells in the lower compartment for the different assay conditions. The results are presented in the histogram (FIG. 25B) and demonstrate the absence of induction of metastatic activity by AOX since the number of cells crossing the membrane are equivalent for the control and AOX conditions. By contrast, in the presence of NAC—a typical cell permeable radical scavenger targeting cytosolic ROS—, we observed a huge increase in metastatic activity.

These results clearly demonstrate that the action of AOX as inhibitor of mitochondrial ROS production does not interfere with cytosolic ROS production.

Conclusion

When directly applied to isolated mitochondria, AOX has some adverse effects on mitochondrial function for high concentrations (above 20 µM), probably due to the protonability of the molecule, which could act as a weak acid and perturb mitochondrial membrane potential. However, we could observe that these conditions are not attained in intact cells where even high concentrations do not trigger mitochondrial dysfunction.

These results demonstrate thus that AOX has no toxic effect on cultured cell for concentrations over 100 µM, i.e., well over potential circulating concentrations under therapeutic treatment. This has been confirmed on the absence of effect of AOX under these conditions on cell respiration and energetic metabolism.

The absence of effect of AOX on the metastatic activity of carcinoma cells by contrast to N-acetyl cystein (NAC), which increased this activity, confirms the specificity of AOX for mitochondrial ROS inhibition and the absence of effect of AOX on cytosolic ROS production.

Example 13: Effect of AOX in a Cardiovascular Disease: Pulmonary Hypertension

The present study aims at providing a new alternative treatment of pulmonary hypertension. This disease is characterized by increased pulmonary arterial pressure and remodeling of pulmonary arteries (PA), leading to increased pulmonary vascular resistance, hypertrophy of the right ventricle, right heart failure and ultimately, death.

Comparative Effects of AOX and AOL on Intrapulmonary Arteries Contractility

To address the issue of the effect of AOX, isometric tension measurements were carried out on intrapulmonary arteries, upon agonist-induced contractions using serotonin or endothelin, in absence and in presence of AOL or AOX.

Material and Methods

Intrapulmonary arteries of the first order (IPA1) were divided into short tubular segments with an external diameter of 1.5-2 mm and used for isometric contraction measurement. Arterial rings were mounted in isolated organ bath systems, containing Krebs solution (containing 118.4 mM NaCl, 4.7 mM KCl, 1.2 mM $MgSO_4$, 25 mM $NaHCO_3$, 1.2 mM $KH_2PO_4$, 2.5 mM $CaCl_2$) and 11.1 mM D-glucose, pH 7.4 adjusted with NaOH) at 37° C. and bubbled continuously with 15% $O_2$/5% $CO_2$. An initial load of 0.8 to 1 g was applied to arterial rings. Tissues were allowed to equilibrate for 1 hour in Kreb's solution and washed out every 15 minutes. A high KCl solution (80 mM) was applied in order to obtain a reference contraction used to normalize subsequent contractile responses.

Contractile responses to different agonists were then tested by constructing a cumulative concentration-response curve (CCRC) to serotonin (5HT, $10^{-4}$ to $10^{-8}$ µM) or endothelin (ET-1, $10^{-7}$ to $10^{-10}$ M). When indicated, AOL or AOX were preincubated during 30 minutes, and then CCRC to agonist was performed in the presence of the drug. High potassium solutions were obtained by substituting an equimolar amount of KCl for NaCl from Kreb's solution. Endothelial function was tested on each ring by examining the relaxation induced by 10 µM carbamylcholine on 0.3 µM Phe-induced preconstricted pulmonary arterial rings. Passive and active mechanical properties were assessed using transducer systems, coupled to IOX software (EMKA Technologies, Paris, France) in order to facilitate data acquisition and analysis.

Results

The contraction was dependent of the concentration of serotonin (5HT) or endothelin (ET-1) with maximal contractions measured with 100 µM 5HT and 0.1 µM ET-1.

Figure 26A:
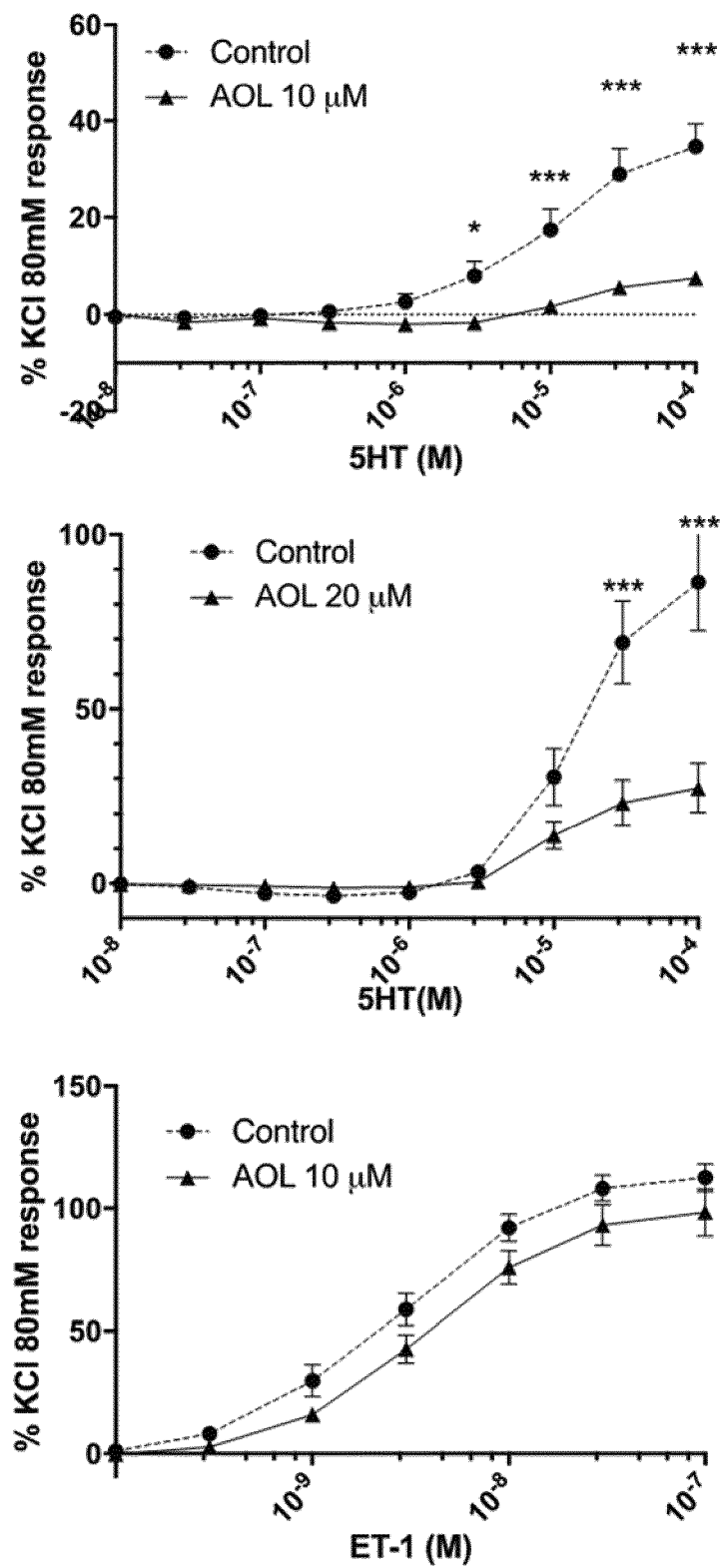
FIG. 26 shows the contraction of intrapulmonary arteries induced by serotonin (5HT) or endothelin (ET-1) in presence of AOL (FIG. 26A) or AOX (FIG. 26B) at different concentrations. 2-way ANOVA: * $p<0.05$;  $p<0.01$; * $p<0.001$.

AOL could relax contractions induced with up to $5·10^{-5}$ M of serotonin, but had no effect on endothelin-induced contractions (FIG. 26A).

Figure 26B:
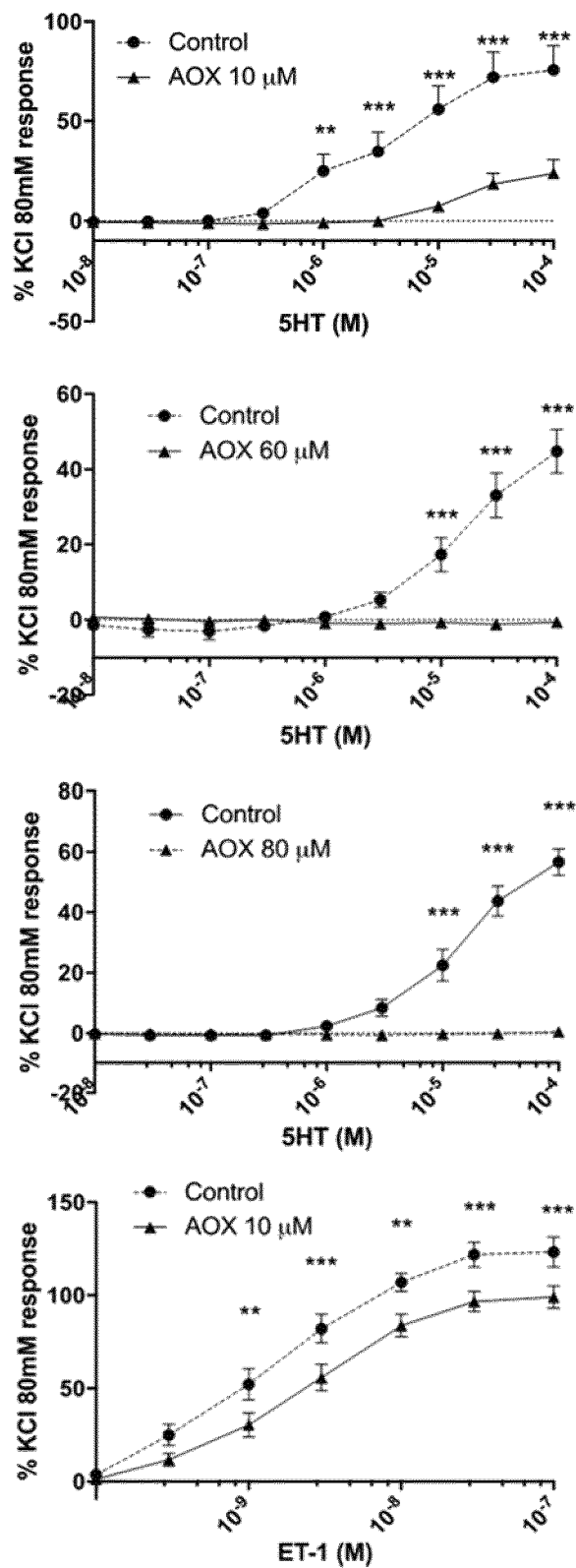

The same pattern of response was observed on rings incubated in a bath containing AOX at 10 μM (FIG. 26B). Using higher concentrations of AOX however, contractions induced with $10^{-4}$ M of serotonin could be relaxed.

Conclusion

These data further confirm that mitochondria play a major role in the pulmonary vasculature physiology, and suggest a greater efficacy of AOX than AOL for the lessening of pulmonary artery contractility and therefore, for the prevention and/or treatment of pulmonary hypertension.

Effect of AOL on Pulmonary Arterial Smooth Muscle Cells Proliferation

Material and Methods

Detection of pulmonary arterial smooth muscle cells (PASMC) proliferation was assayed by using a colorimetric immunoassay kit (Roche Applied Science, Indianapolis, Ind., USA) based on the measurement of 5-bromo-2'-deoxyuridine (BrdU) incorporation during DNA synthesis.

Isolated PASMC were seeded in culture medium supplemented with 10% fetal calf serum (FCS) at a density of $5\cdot 10^3$ cells/well/100 μL in a 96-well culture plate. The culture plate was placed in a humidified incubator at 37° C. under 5% $CO_2$ in air. After 48 hours, cells were subjected to 48 hours of growth arrest in serum-free culture medium supplemented with 1% insulin-transferrin-selenium. At the end of this period, PASMC were incubated for 24 hours in culture medium containing either:

0.2% FCS (control condition);
0.2% FCS+10, 20, 60 or 100 μM AOL;
0.2% FCS+100 μM 5HT (serotonin);
0.2% FCS+100 μM 5HT+10, 20, 60 or 100 μM AOL;
10% FCS;
10% FCS+10, 20, 60 or 100 μM AOL.

Each condition was tested in triplicate. 10 μL of BrdU (100 μM) was then added to the media and cells were incubated for an additional 2 hours at 37° C. DNA synthesis was then assayed using the colorimetric method, according to the manufacturer's instructions. Newly synthesized BrdU DNA was determined by measuring absorbance of the samples in an ELISA reader (Spectrostar/nano; BMG Labtech, Champigny-sur-Marne, France) at a wavelength of 380 nm with a reference wavelength of 490 nm.

Results

Figure 27:
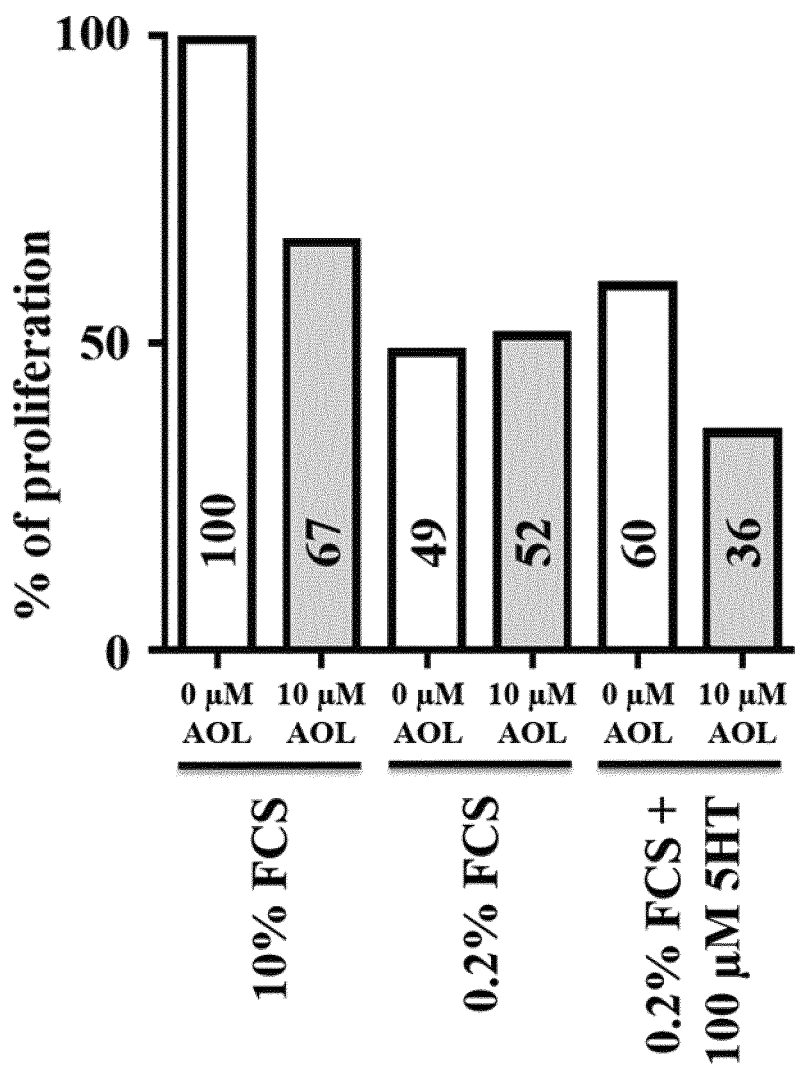
FIG. 27 shows the proliferation of pulmonary arterial smooth muscle cells (PASMC) after incubation in 10% fetal calf serum (FCS), 0.2% FCS and 0.2% FCS+100 μM serotonin (5HT), in presence or in absence of AOL.

As reported in FIG. 27, AOL successfully inhibited the proliferation induced by a high concentration of FCS (10%) or in more physiological conditions, i.e., in presence of 0.2% of FCS and 100 μM 5HT.

Conclusion

These data suggest that AOL has a potential effect in the prevention and/or treatment of pulmonary hypertension.

Example 14: Effect of AOX in a Cardiovascular Disease: Cardiac Toxicity of Anthracyclines The present study aims at evaluating the effect of AOX in a model of cardiac toxicity of anthracyclines. This was assessed by administering anthracycline-derived anti-cancer drugs, together with AOX, to 10-week-old rats for 14 to 17 days.

Material and Methods

The studies were performed on Sprague-Dawley rats aged 10 weeks and different treatments were administered intraperitoneally for 14 to 17 days, before collection of the heart for analysis. To respect the "three Rs principle" in animal experimentation, the number of group tested was limited as much as possible, in particular by focusing the experiments on one anthracycline molecule only, namely Doxorubicine, and by comparing the effect of AOX to one alternative protective molecule only, namely Dexrazoxane.

At the end of the experiment, the heart of the rats treated will be removed and cardiac function will be studied exhaustively after perfusion of these hearts in a Langendhorf system to determine the function cardiac affected by doxorubicin and whether AOX treatment is efficient.

The study comprises 5 different groups for 8 rats each:

1—Control group. Rats received the vehicle only, composed of 5% DMSO+95% NaCl 0.9%, twice a day (morning and evening) for 17 days;

2—Doxo group. Rats received Doxorubicine at a dose of 3 mg/kg (i.p.), every two days (morning), from day 3, for 14 days. Rats received vehicle only for every other injection;

3—Dexra group. Rats were treated with Dexrazoxane (reference protecting agent) at a dose of 30 mg/kg i.p. simultaneously with Doxorubicin at a dose of 3 mg/kg i.p. (according to the dosage ratio recommended by the French Regional Health Agency "ARS" in 2011), every two days, from day 3, for 14 days. Rats received vehicle only for every other injection;

4—AOX group. Rats were treated with AOX and Doxorubicin:
  4 mg/kg i.p. of AOX, mornings and evenings, for 72 hours preceding the first injection of Doxorubicin;
  on the days of Doxorubicin injection (based on the Doxo group): 4 mg/kg i.p. AOX together with the Doxorubicin injection, followed 90 minutes later by a second injection of AOX at a dose of 4 mg/kg i.p.;
  on the days without Doxorubicin injection: 4 mg/kg i.p. of AOX, mornings and evenings.

5-AOX/Carv/Enal group. Rats were treated similarly than rats from the AOX group here above. AOX injections were supplemented with a classical treatment for cardiac insufficiency (Carvediol, a β-blocker, at a dose of 1 mg/kg, and Enalapril, a vasodilator, at a dose of 0.5 mg/kg).

Example 15: Effect of AOX in an Autoimmune Disease: Scleroderma

The present study aims at testing the effect of AOX on fibroblasts from patients with scleroderma. Scleroderma is a chronic systemic autoimmune disease characterized by an increased synthesis of collagen, damages to small blood vessels, activation of T lymphocytes and production of altered connective tissues.

Material and Methods

Fibroblasts from both a healthy donor and a patient with scleroderma are cultured in flasks, in complete DMEM medium (10% FCS, 1% antibiotic). After 6-hour adhesion, cells are deprived of serum overnight.

AOX is extemporaneously prepared. AOX was weighed and dissolved in DMSO at 5 mg/mL. This stock solution was further diluted to 10 and 5 mM final, in DMSO. AOX was further diluted in complete DMEM medium, to reach final concentrations of 40, 20 and 10 μM.

Cultured cells were contacted with AOX at 40, 20 and 10 μM. Control cells were contacted with complete DMEM medium, supplemented with DMSO (0.2%) and N-acetylcysteine (3 mM). Cells are incubated under normoxic conditions (37° C., 20% 02) and under hypoxia (37° C., 1% $O_2$) for 6 or 24 hours.

For MMP-1, MIP and MCP secretion analysis, the culture supernatant is harvested, aliquoted and stored at −20° C. for dosage. MMP-1 is quantified by ELISA (Abcam), according to the manufacturer's instructions. MCP-1 and MIP-la concentrations are quantified by CBA (Cytometric Bead Array, Biolegend).

For MMP1, collagen and CCl2 expression analysis, cells are detached with trypsin and washed with PBS. The cell pellet is then resuspended in lysis buffer, and RNA extraction is carried out according to the manufacturer's instructions (Nucleospin RNA Plus, Macherey Nagel). 1 μg of RNA is retro-transcribed (GoScript, Promega), then diluted 10-fold before SYBR Green qPCR (SYBR qPCR Premix Ex Taq, Takara) in a BioRad CFX384 PCR machine. Primers for MMP-1, CollA2 and CCl2 are used to measure genes of interest; primers for Ppia, RPLP0 and EEF1A1 are used to measure reference genes.

Example 16: AOX Inhibits Selectively ROS Production at Site $I_Q$ Contrary to Oltipraz Material and Methods After freshly isolating mitochondria from rat heart, then measuring protein quantity of the mitochondrial suspension, $H_2O_2$ production in response to the exogenous addition of increasing concentrations of AOL, AOX and Oltipraz was measured fluorimetrically with Amplex Red and horseradish peroxidase (HRP).

The two major sites of mitochondrial ROS/$H_2O_2$ production were targeted individually using the combination of succinate (energy substrate of respiratory complex 2) and known inhibitors of respiratory chain, namely for site $I_Q$, 10 mM succinate alone (CCCP as positive control) and for site $III_{Qouter}$, 10 mM succinate, 4 μM rotenone and 2.5 μM antimycin A (myxothiazol as positive control). These "reaction" solutions were designed to generate maximal rates of ROS/$H_2O_2$ production predominantly from a single site within the chain (Quinlan et al. 2013. Redox Biol. 1:304-12).

For measurement, a working solution of 50 μM Amplex red reagent and 20 μg/ml HRP was mixed to the reaction buffer into the corresponding wells of a 96-well plate (Greiner 96 F-bottom), in the absence or presence of increasing concentrations (from 0 to 80 μM) of AOL, AOX or Oltipraz. Addition of mitochondria to a final concentration of 0.125 mg/mL per well initiated the assay. The appropriate total volume per microplate well was 200 μL.

Plates were incubated in the dark at room temperature for 20-25 minutes. A double orbital shaking (100 rpm-3 seconds) was applied before reading the endpoint fluorescence values on a CLARIOstar plate reader (BMG LABTECH GmbH, Germany). In fact, $H_2O_2$ reacts with Amplex Red in a 1:1 stoichiometry, yielding the fluorescent compound resorufin that was analyzed using the following optic settings (excitation wavelength at 546-20 nm; emission at 600-40 nm; gain: 750).

Also, an $H_2O_2$ standard curve, with concentrations ranging from 0 to 5 μM, was prepared in the experimental buffer that consisted in (in mM): 140 sucrose, 100 KCl, 1 EGTA, 20 $MgCl_2$, 10 $KH_2PO_4$, and 1 g/L (w/v) BSA essentially fatty acid free (pH 7.2).

Results

FIG. 28 illustrates the effect of increasing concentrations of AOL, AOX and Oltipraz (from 0 to 80 μM) on ROS/$H_2O_2$ production measured under these conditions.

Figure 28A:
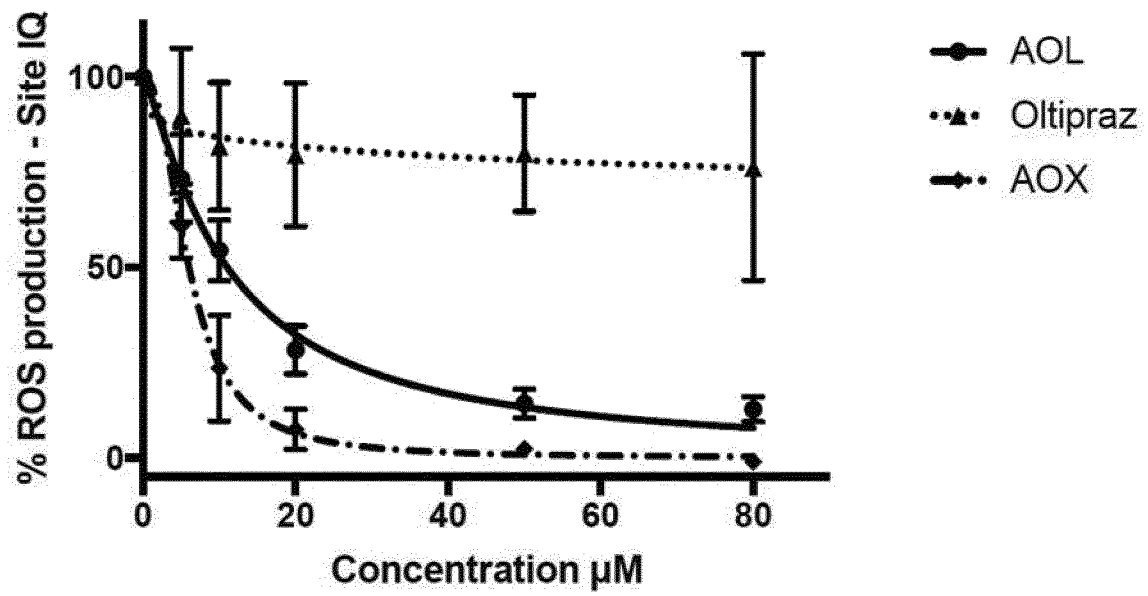
FIG. 28A shows the effect of the three molecules on site $I_Q$ and FIG. 28B shows the effect on site $III_{QO}$.

It clearly appears from the results of FIG. 28A that AOL and AOX strongly inhibit the ROS production by complex I, at concentrations as low as 2.5 μM. On the contrary, Oltipraz, at the same concentrations, and up to 80 μM, showed only a poor effect on the inhibition of ROS production in site $I_Q$.

Figure 28B:
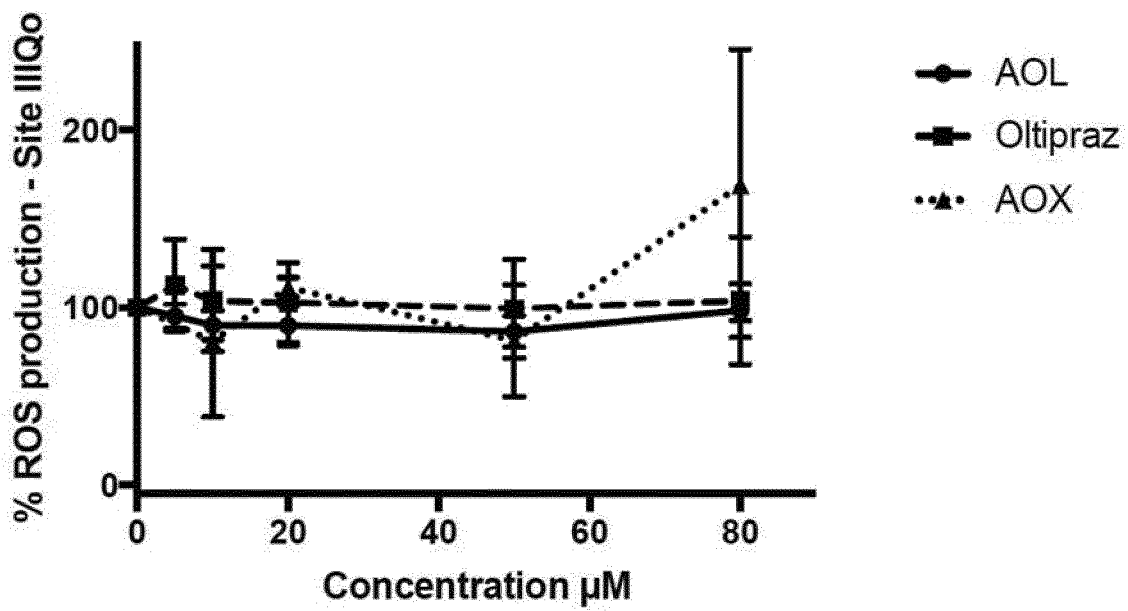

FIG. 28B further shows that none of the three compounds have an effect on the inhibition of ROS production by complex III.

Together, these results clearly demonstrate that AOL and AOX are site IQ-selective inhibitors of mitochondrial ROS production, contrary to Oltipraz.

Example 17: AOX Analogs Inhibit Superoxide/$H_2O_2$ Production by Mitochondria

Material and Methods

The same protocol as described above in Example 16 was used to measure ROS/$H_2O_2$ production in response to the exogenous addition of various AOX analogs. Namely, a working solution of 50 μM Amplex red reagent and 20 μg/mL HRP was mixed to the reaction buffer into the corresponding wells of a 96-well plate (Greiner 96 F-bottom), in the absence or presence of increasing concentrations (from 1 to 25 μM) of eight compounds (Cp1; Cp2; Cp3; Cp4; Cp5; Cp6a; Cp8; Cp9a). Addition of mitochondria to a final concentration of 0.125 mg/mL per well initiated the assay. The appropriate total volume per microplate well was 200 μL.

Results

Figure 29A:
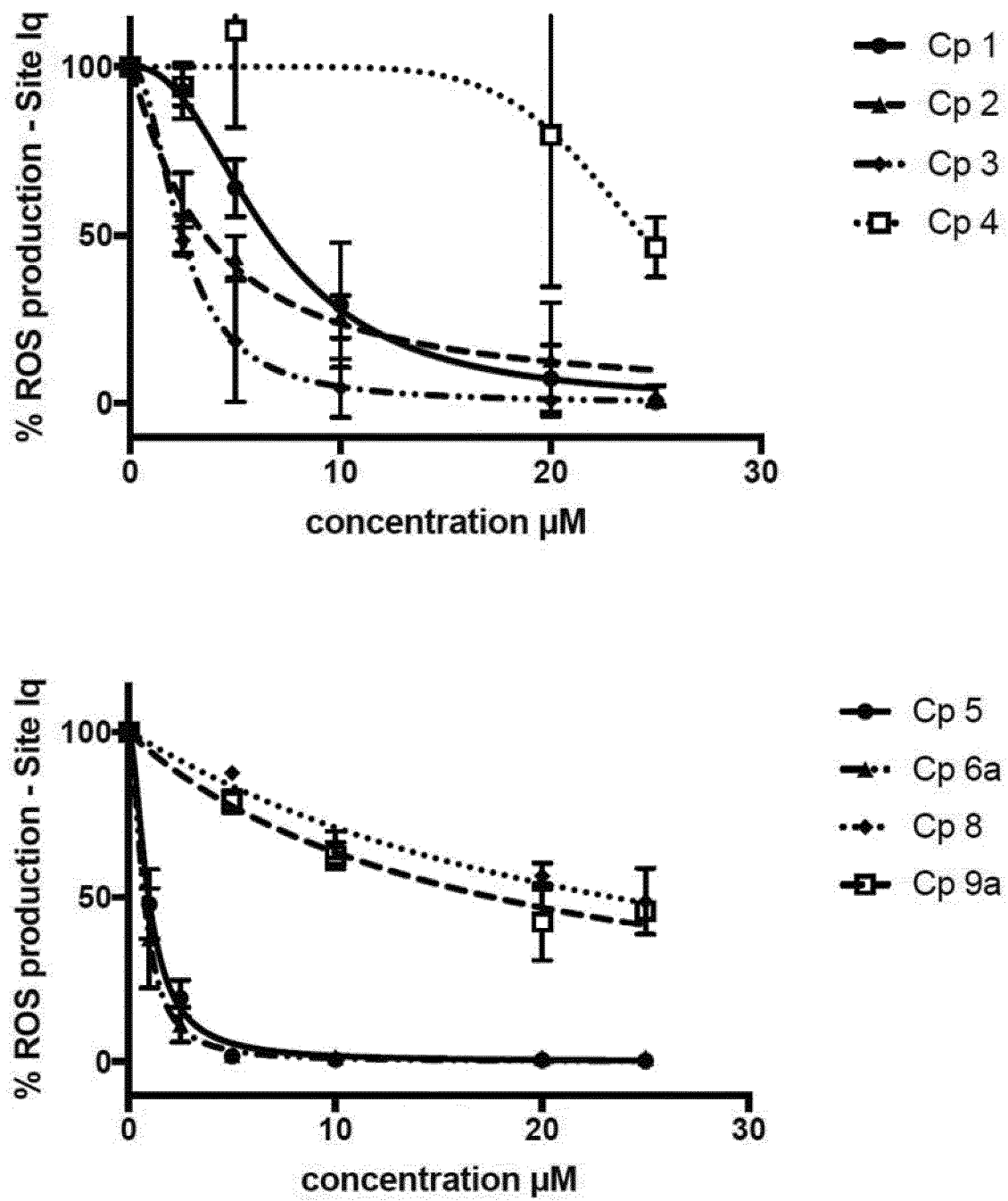
FIG. 29A shows the effect of (upper panel) Cp1, Cp2, Cp3, Cp4, (lower panel) Cp5, Cp6a, Cp8 and Cp9a on site $I_Q$
Figure 29B:
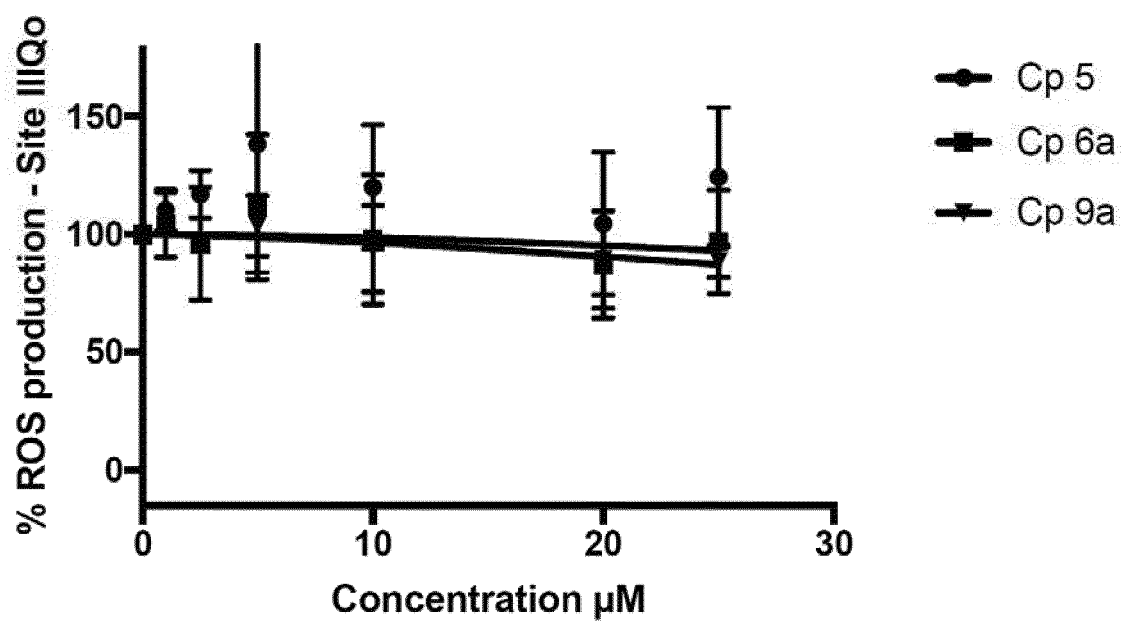
FIG. 29B shows the effect of Cp5, Cp6a and Cp9a on site $III_{QO}$.

FIGS. 29A and 29B illustrate the effect of increasing concentrations of AOX analogs (from 2.5 to 25 μM) on ROS/$H_2O_2$ production measured under these conditions.

It clearly appears from the results presented in these figures that AOX analogs inhibits the ROS production by complex I, selectively with respect to complex III.

The invention claimed is:
1. A compound of formula (I'):

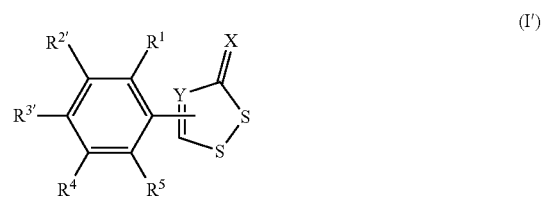

or a pharmaceutically acceptable tautomer, salt or solvate thereof, wherein:

X represents S, O or NHOH;

Y represents CH, C or N;

$R^1$, $R^4$ and $R^5$ each independently represent hydrogen, hydroxy, halo, amino, alkylsulfonyl, aminosulfonyl, cyano, nitro, carboxy, aryl, alkoxy, haloalkyl, alkylamino, am inoalkyl, nitrooxyalkyl or carboxyalkyl;

$R^{2'}$ and $R^{3'}$ together with the carbon atoms to which they are attached form a 5-membered heteroaryl moiety wherein —$R^{3'}$—$R^{2'}$— represents -A-$CR^6$=B— or —B=$CR^6$-A—; wherein:

A represents O, S or NR'; wherein $R^7$ represents hydrogen, C1—C8 alkyl or alkyloxycarbonyl;

B represents CH or N; and $R^6$ represents hydrogen, hydroxy, halo, amino, alkylsulfonyl, aminosulfonyl, cyano, nitro, carboxy, aryl, alkoxy, haloalkyl, alkylamino, aminoalkyl, nitrooxyalkyl or carboxyalkyl.

2. The compound according to claim 1, of formula (IIa), (IIb), (IIIa) or (IIIb):

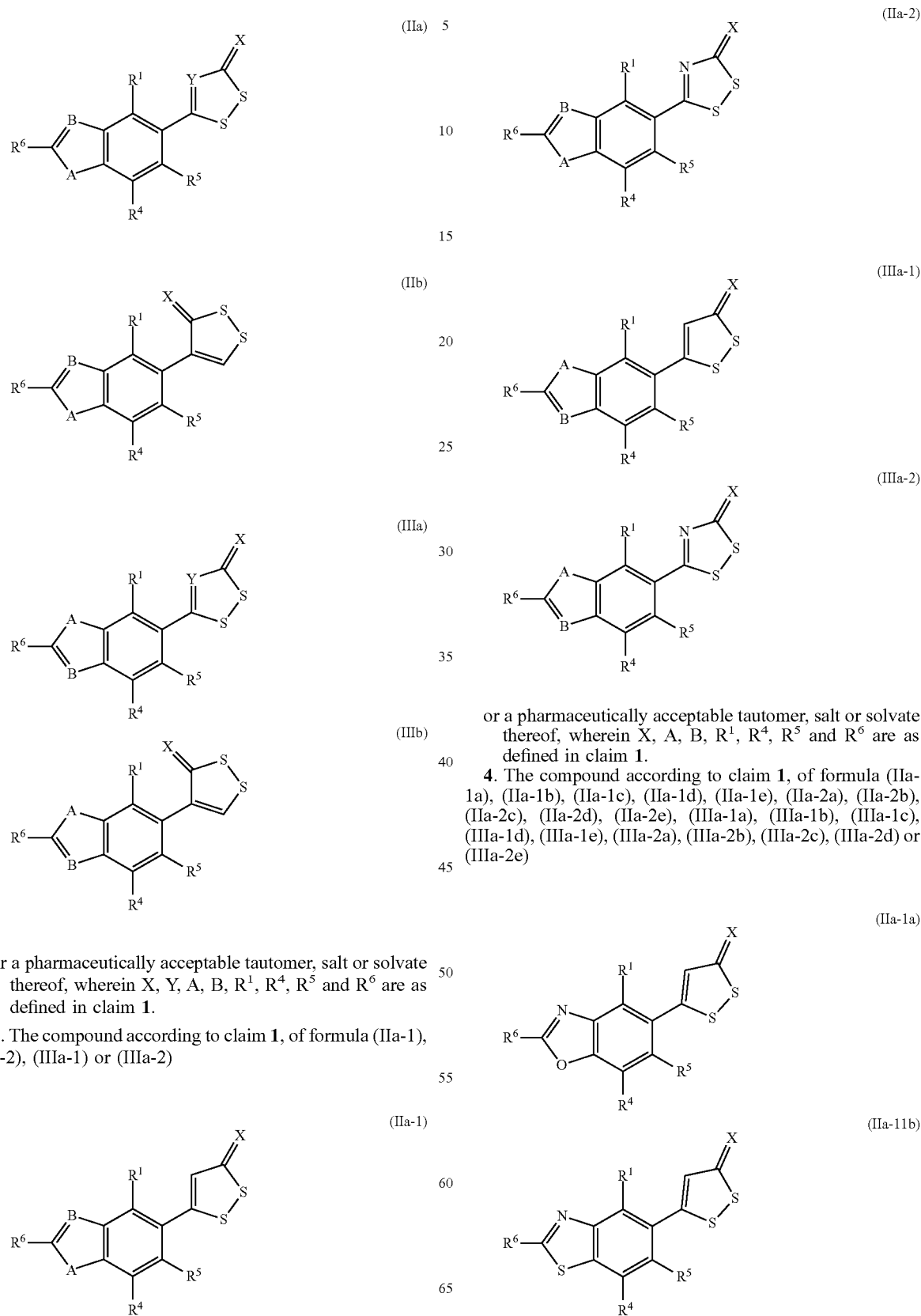

or a pharmaceutically acceptable tautomer, salt or solvate thereof, wherein X, Y, A, B, $R^1$, $R^4$, $R^5$ and $R^6$ are as defined in claim 1.

3. The compound according to claim 1, of formula (IIa-1), (IIa-2), (IIIa-1) or (IIIa-2)

or a pharmaceutically acceptable tautomer, salt or solvate thereof, wherein X, A, B, $R^1$, $R^4$, $R^5$ and $R^6$ are as defined in claim 1.

4. The compound according to claim 1, of formula (IIa-1a), (IIa-1b), (IIa-1c), (IIa-1d), (IIa-1e), (IIa-2a), (IIa-2b), (IIa-2c), (IIa-2d), (IIa-2e), (IIIa-1a), (IIIa-1b), (IIIa-1c), (IIIa-1d), (IIIa-1e), (IIIa-2a), (IIIa-2b), (IIIa-2c), (IIIa-2d) or (IIIa-2e)

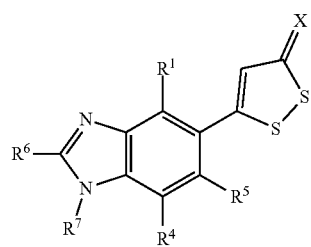 (IIa-1c)
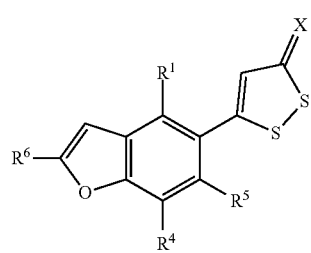 (IIa-1d)
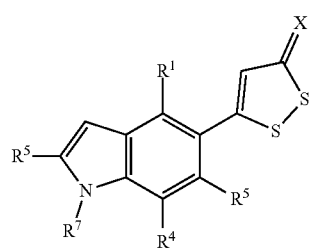 (IIa-1e)
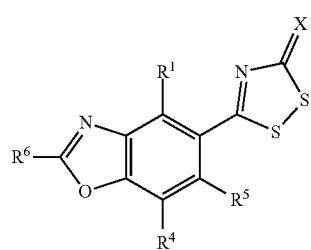 (IIa-2a)
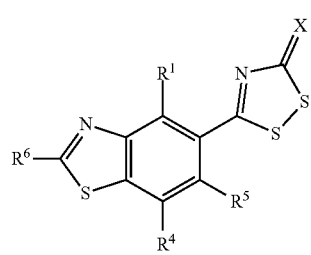 (IIa-2b)
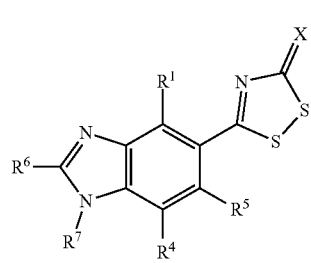 (IIa-2c)
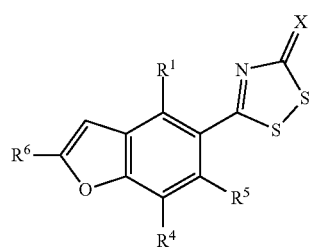 (IIa-2d)
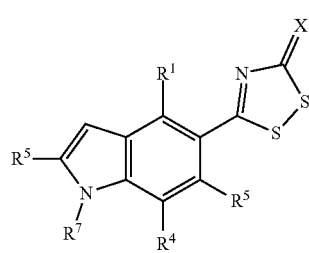 (IIa-2e)
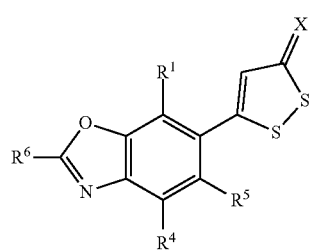 (IIIa-1a)
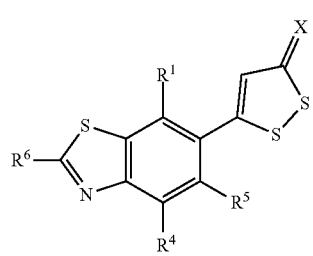 (IIIa-1b)
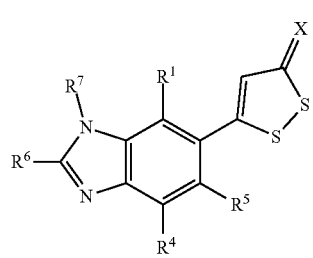 (IIIa-1c)
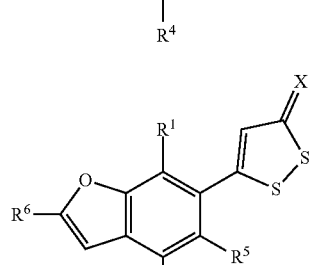 (IIIa-1d)

-continued
(IIIa-1e)
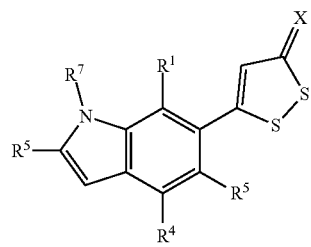
(IIIa-2a)
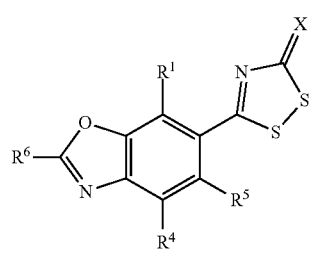
(IIIa-2b)
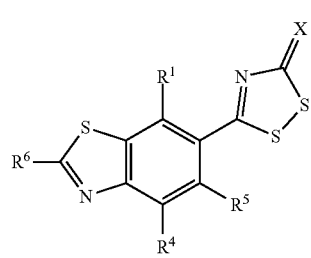
(IIIa-2c)
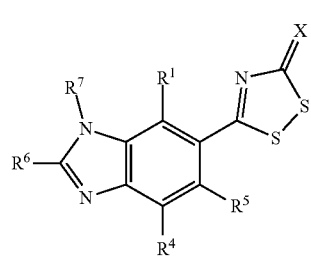
(IIIa-2d)
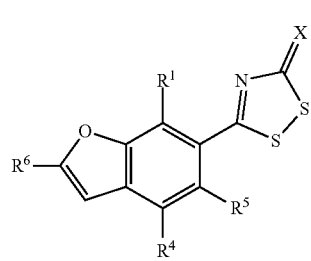
(IIIa-2e)
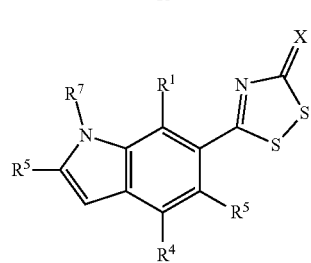
or a pharmaceutically acceptable tautomer, salt or solvate thereof, wherein X, $R^1$, $R^4$, $R^5$, $R^6$ and $R^7$ are as defined in claim 1.
5. The compound according to claim 1, being of formula (IIb-1), (IIb-2), (IIb-3), (IIb-4), (IIb-5), (IIIb-1), (IIIb-2), (IIIb-3), (IIIb-4) or (IIIb-5)
(IIb-1)
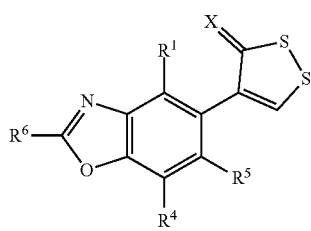
(IIb-2)
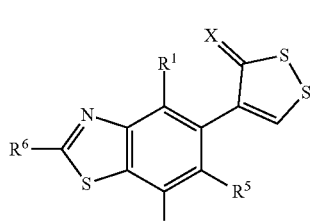
(IIb-3)
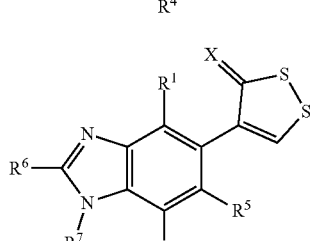
(IIb-4)
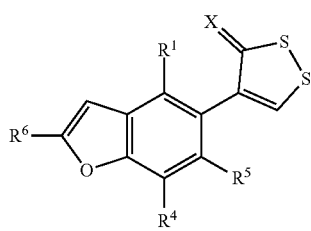
(IIb-5)
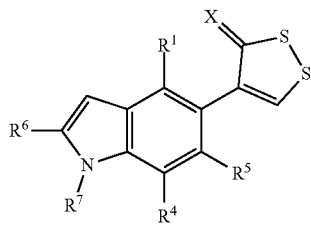
(IIIb-1)
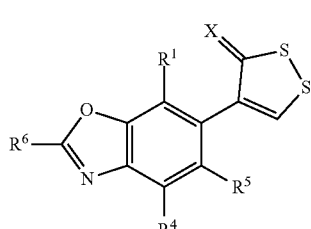
(IIIb-2)
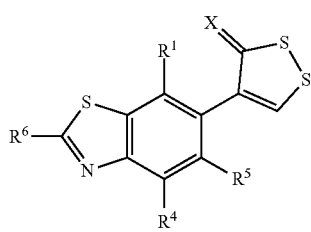

-continued (IIIb-3)
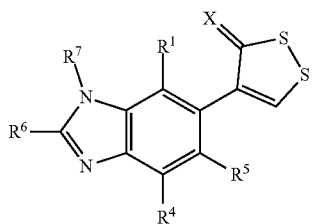

(IIIb-4)
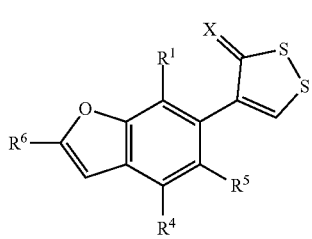

(IIIb-5)
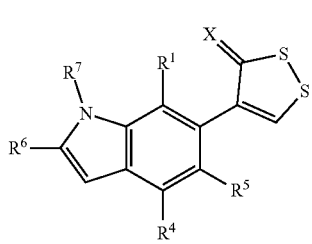

or a pharmaceutically acceptable tautomer, salt or solvate thereof, wherein X, $R^1$, $R^4$, $R^5$, $R^6$ and $R^7$ are as defined in claim 1.

6. The compound according to claim 1, wherein X is S or O; and/or Y is CH or N.

7. The compound according to claim 1, wherein X is S; and/or Y is CH.

8. The compound according to claim 1, said compound being selected from the group consisting of:

5-(2-hydroxybenzo[d]oxazol-5-yl)-3H-1,2-dithiole-3-thione;

5-(2-hydroxybenzo[d]thiazol-6-yl)-3H-1,2-dithiole-3-thione;

5-(benzofuran-5-yl)-3H-1,2-dithiole-3-thione; and methyl 5-(3-thioxo-3H-1,2-dithiol-5-yl)-1H-indole-1-carboxylate.

9. A pharmaceutical composition comprising a compound according to claim 1, or a pharmaceutically acceptable tautomer, salt or solvate thereof, and at least one pharmaceutically acceptable excipient.

10. A medicament comprising a compound according to claim 1, or a pharmaceutically acceptable tautomer, salt or solvate thereof.

11. A process for manufacturing a compound of Formula (IIa-1) according to claim 3 or a pharmaceutically acceptable tautomer, salt or solvate thereof, characterized in that it comprises:

a) cyclizing a compound of formula (C)

(C)
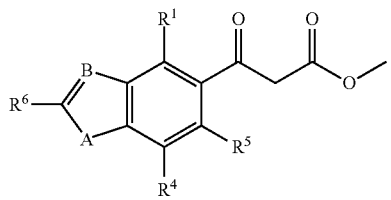

wherein A, B, $R^1$, $R^4$, $R^5$ and $R^6$ are as defined in claim 3;
with a sulfur-based reagent, in the presence of a siloxane; to obtain a compound of formula (IIa-1')

(IIa-1')
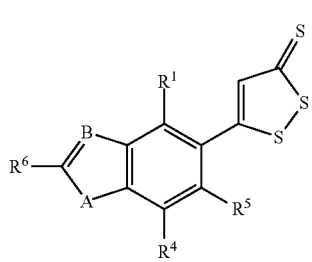

or a pharmaceutically acceptable tautomer, salt or solvate thereof, wherein A, B, $R^1$, $R^4$, $R^5$ and $R^6$ are as defined in claim 3; and optionally:

b1) compound of formula (IIa-1') can react with an oxidant; to obtain a compound of formula (IIa-1")

(IIa-1")
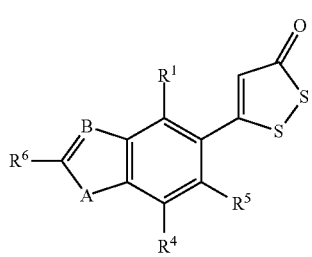

or a pharmaceutically acceptable tautomer, salt or solvate thereof, wherein A, B, $R^1$, $R^4$, $R^5$ and $R^6$ are as defined in claim 3; or b2) compound of formula (IIa-1') can react with hydroxylamine $NH_2OH$—HCl; in the presence of a base; to obtain a compound of formula (IIa-1''')

(IIa-1''')
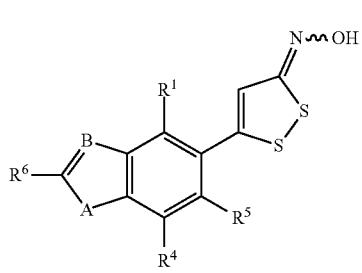

or a pharmaceutically acceptable tautomer, salt or solvate thereof, wherein A, B, $R^1$, $R^4$, $R^5$ and $R^6$ are as defined in claim 3.

12. The process according to claim 11, wherein the base is sodium acetate (AcONa) and/or the oxidant is mercury acetate $Hg(OAc)_2$.

13. A method for treating free oxygen radicals-related diseases in a subject in need thereof, comprising administering to said subject an inhibitor of production of reactive oxygen species (ROS), wherein said inhibitor is a compound of formula (I'):

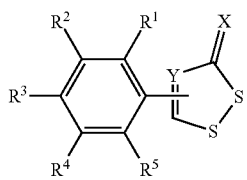
(I)

or a pharmaceutically acceptable tautomer, salt or solvate thereof wherein:

X represents S, O, or NHOH;
Y represents CH, C, or N;
$R^1$, $R^4$, and $R^5$ each independently represent hydrogen, hydroxy, halo, amino, alkylsulfonyl, aminosulfonyl, cyano, nitro, carboxy, aryl, alkoxy, haloalkyl, alkylamino, am inoalkyl, nitrooxyalkyl or carboxyalkyl;
$R^{2'}$ and $R^{3'}$ together with the carbon atoms to which they are attached form a 5-membered heteroaryl moiety wherein —$R^{3'}$—$R^{2'}$— represents -A-$CR^6$=B— or —B=$CR^6$-A—; wherein:
A represents O, S, or $NR^{7'}$; wherein $R^7$ represents hydrogen, C1-C8 alkyl or alkyloxycarbonyl;
B represents CH or N; and
$R^6$ represents hydrogen, hydroxy, halo, amino, alkylsulfonyl, aminosulfonyl, cyano, nitro, carboxy, aryl, alkoxy, haloalkyl, alkylamino, aminoalkyl, nitrooxyalkyl or carboxyalkyl;
wherein said free oxygen radicals-related diseases are selected from the group consisting of cardiovascular diseases, aging diseases, auto-immune diseases, progeroid syndromes, Parkinsonian syndromes, neurological diseases, ischemic and reperfusion injuries, infectious diseases, muscles diseases and lung, kidney and liver diseases.

14. The method according to claim 13, wherein said compound is selected from:
5-(2-hydroxybenzo[d]oxazol-5-yl)-3H-1,2-dithiole-3-thione;
5-(2-hydroxybenzo[d]thiazol-6-yl)-3H-1,2-dithiole-3-thione;
5-(benzofuran-5-yl)-3H-1,2-dithiole-3-thione; and
methyl 5-(3-thioxo-3H-1,2-dithiol-5-yl)-1H-indole-1-carboxylate.

15. The method according to claim 13, wherein said compound is of formula (II) or (III):

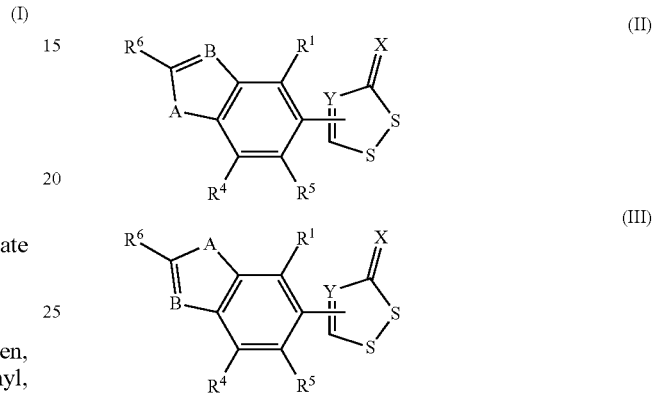

or a pharmaceutically acceptable tautomer, salt or solvate thereof, wherein X, Y, $R^1$, $R^4$, $R^5$, $R^6$, A and B are as defined in claim 13.

16. The method according to claim 13, wherein said compound inhibits mitochondrial production of ROS.

17. The method according to claim 16, wherein the compound inhibits mitochondrial production of ROS at site $I_Q$ of complex I of mitochondria.

18. The method according to claim 13, wherein said cardiovascular diseases are selected from the group comprising myocardial infarction, ischemia-reperfusion injury, heart failure, thrombosis and embolism, cardiopulmonary diseases, cardiac toxicity of anthracyclines, cardiac toxicity of anti-cancer drugs, cardiac toxicity of antiviral drugs, cardiac toxicity of quinolones, ischemia, stroke, cardiac fibrillation, pulmonary arterial hypertension, heart attack, hypertension and cardiomyopathies.

* * * * *